(12) United States Patent
Goodman et al.

(10) Patent No.: US 11,497,780 B2
(45) Date of Patent: *Nov. 15, 2022

(54) PREBIOTIC FORMULATIONS

(71) Applicants: RESEARCH INSTITUTE AT NATIONWIDE CHILDREN'S HOSPITAL, Columbus, OH (US); OHIO STATE INNOVATION FOUNDATION, Columbus, OH (US)

(72) Inventors: Steven D. Goodman, Hilliard, OH (US); Lauren O. Bakaletz, Hilliard, OH (US); Michael Bailey, Columbus, OH (US); Gail Besner, Columbus, OH (US)

(73) Assignees: Research Institute at Nationwide Children's Hospital, Columbus, OH (US); Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/820,463

(22) Filed: Mar. 16, 2020

(65) Prior Publication Data

US 2021/0100854 A1  Apr. 8, 2021

Related U.S. Application Data

(63) Continuation of application No. 15/649,352, filed on Jul. 13, 2017, now Pat. No. 10,624,934, which is a continuation-in-part of application No. 15/257,673, filed on Sep. 6, 2016, now Pat. No. 10,369,176, which is a continuation of application No. PCT/US2015/019059, filed on Mar. 5, 2015.

(60) Provisional application No. 62/477,382, filed on Mar. 27, 2017, provisional application No. 61/949,058, filed on Mar. 6, 2014.

(51) Int. Cl.
| | |
|---|---|
| *A61K 35/747* | (2015.01) |
| *A61K 9/50* | (2006.01) |
| *A61K 35/741* | (2015.01) |
| *A61K 9/00* | (2006.01) |
| *A61K 47/22* | (2006.01) |
| *A61K 47/10* | (2017.01) |
| *A23L 33/195* | (2016.01) |
| *A61K 9/16* | (2006.01) |
| *A23L 33/135* | (2016.01) |
| *A01N 63/20* | (2020.01) |
| *A01N 63/22* | (2020.01) |
| *A01N 63/23* | (2020.01) |
| *A01N 63/27* | (2020.01) |

(52) U.S. Cl.
CPC .......... *A61K 35/747* (2013.01); *A01N 63/20* (2020.01); *A01N 63/22* (2020.01); *A01N 63/23* (2020.01); *A01N 63/27* (2020.01); *A23L 33/135* (2016.08); *A23L 33/195* (2016.08); *A61K 9/0031* (2013.01); *A61K 9/1647* (2013.01); *A61K 9/1652* (2013.01); *A61K 9/1658* (2013.01); *A61K 9/50* (2013.01); *A61K 35/741* (2013.01); *A61K 47/10* (2013.01); *A61K 47/22* (2013.01); *A23V 2002/00* (2013.01); *A23V 2200/3202* (2013.01); *A23V 2200/3204* (2013.01)

(58) Field of Classification Search
None
See application file for complete search history.

(56) References Cited

U.S. PATENT DOCUMENTS

| | | | |
|---|---|---|---|
| 5,549,908 | A  | 8/1996  | Smith et al. |
| 6,486,314 | B1 | 11/2002 | Van Geel-Schutten et al. |
| 6,551,795 | B1 | 4/2003  | Rubenfield et al. |
| 7,241,867 | B2 | 7/2007  | Bakaletz et al. |
| 7,435,595 | B2 | 10/2008 | Boehm et al. |
| 7,638,282 | B2 | 12/2009 | Bakaletz et al. |
| 7,816,086 | B2 | 10/2010 | Bakaletz et al. |
| 7,981,676 | B2 | 7/2011  | Boehm et al. |
| 7,998,490 | B2 | 8/2011  | Bakaletz et al. |
| 8,236,494 | B2 | 8/2012  | Bakaletz et al. |
| 8,283,114 | B2 | 10/2012 | Bakaletz et al. |
| 8,628,917 | B2 | 1/2014  | Bakaletz et al. |
| 8,652,773 | B2 | 2/2014  | Bakaletz et al. |
| 8,758,764 | B2 | 6/2014  | Masignani et al. |
| 8,999,291 | B2 | 4/2015  | Goodman et al. |
| 9,005,682 | B2 | 4/2015  | Sprenger et al. |
| 9,034,642 | B2 | 5/2015  | Bakaletz et al. |
| 9,278,069 | B2 | 3/2016  | Berkland et al. |
| 9,504,739 | B2 | 11/2016 | Berkes et al. |

(Continued)

FOREIGN PATENT DOCUMENTS

| | | |
|---|---|---|
| DE | 20 2013 103 204 U1 | 9/2013 |
| EP | 3 113 630 A2 | 1/2017 |

(Continued)

OTHER PUBLICATIONS

Fei Wu, et al., "Development of dextran nanoparticles for stabilizing delicate proteins" Nanoscale Hesecrch Letters, 2013, pp. 1-8.

(Continued)

*Primary Examiner* — Nita M. Minnifield
(74) *Attorney, Agent, or Firm* — Foley & Lardner LLP

(57) ABSTRACT

Provided herein are compositions comprising a biocompatible microsphere, a biofilm-generating probiotic bacterium, a prebiotic, and/or a prebiofilmic. Methods for preparing and formulating the compositions and methods for treating or preventing a disease using the compositions are also provided.

11 Claims, 26 Drawing Sheets

Specification includes a Sequence Listing.

(56) References Cited

U.S. PATENT DOCUMENTS

| | | | |
|---|---|---|---|
| 9,554,590 B2 | 1/2017 | Quintens et al. | |
| 9,603,878 B2 | 3/2017 | Berry et al. | |
| 9,610,307 B2 | 4/2017 | Berry et al. | |
| 9,622,956 B2 | 4/2017 | Schaeffer-Korbylo et al. | |
| 9,687,449 B2 | 6/2017 | Harel | |
| 9,713,631 B2 | 7/2017 | Berkes et al. | |
| 9,717,765 B2 | 8/2017 | Berkes et al. | |
| 10,369,176 B2 * | 8/2019 | Goodman | A23L 33/135 |
| 10,624,934 B2 * | 4/2020 | Goodman | A01N 63/20 |
| 2005/0059633 A1 | 3/2005 | Van Geel-Schuten | |
| 2005/0112235 A1 | 5/2005 | Shefer et al. | |
| 2005/0170504 A1 | 8/2005 | Boehm et al. | |
| 2005/0266069 A1 | 12/2005 | Simmons et al. | |
| 2007/0207210 A1 | 9/2007 | Brown et al. | |
| 2009/0155912 A1 | 6/2009 | Boehm et al. | |
| 2011/0008493 A1 | 1/2011 | Zorea | |
| 2011/0236306 A1 | 9/2011 | Goodman et al. | |
| 2012/0128701 A1 | 5/2012 | Goodman et al. | |
| 2012/0247993 A1 | 10/2012 | Palazzi et al. | |
| 2014/0005649 A1 | 1/2014 | Burnett et al. | |
| 2014/0010918 A1 | 1/2014 | Quintens et al. | |
| 2014/0120107 A1 | 5/2014 | Bakaletz et al. | |
| 2014/0170126 A1 | 6/2014 | Duncker et al. | |
| 2014/0356389 A1 | 12/2014 | Masignani et al. | |
| 2014/0363410 A1 | 12/2014 | Bergonzelli Degonda et al. | |
| 2014/0377192 A1 | 12/2014 | Schaeffer-Korbylo et al. | |
| 2015/0086542 A1 | 3/2015 | Goodman et al. | |
| 2015/0086561 A1 | 3/2015 | Kauvar et al. | |
| 2015/0110838 A1 | 4/2015 | Agrawal | |
| 2015/0166641 A1 | 6/2015 | Goodman et al. | |
| 2015/0173374 A1 | 6/2015 | Majeed et al. | |
| 2015/0197558 A1 | 7/2015 | Kauvar et al. | |
| 2015/0218231 A1 | 8/2015 | Bakaletz et al. | |
| 2015/0247993 A1 | 9/2015 | Ishizaka | |
| 2015/0290140 A1 | 10/2015 | Singh et al. | |
| 2016/0089363 A1 | 3/2016 | Borody | |
| 2016/0095316 A1 | 4/2016 | Goodman et al. | |
| 2016/0120915 A1 | 5/2016 | Blaser et al. | |
| 2016/0143961 A1 | 5/2016 | Berry et al. | |
| 2016/0175440 A1 | 6/2016 | Goodman et al. | |
| 2016/0193258 A1 | 7/2016 | Berry et al. | |
| 2016/0194384 A1 | 7/2016 | Goodman et al. | |
| 2016/0199424 A1 | 7/2016 | Berry et al. | |
| 2016/0223553 A1 | 8/2016 | Sears et al. | |
| 2016/0228476 A1 | 8/2016 | Cutcliffe et al. | |
| 2016/0235792 A1 | 8/2016 | Berry et al. | |
| 2016/0237145 A1 | 8/2016 | Kauvar et al. | |
| 2016/0244489 A1 | 8/2016 | Masignani et al. | |
| 2016/0271188 A1 | 9/2016 | Berry et al. | |
| 2016/0289278 A1 | 10/2016 | Bakaletz et al. | |
| 2017/0056454 A1 | 3/2017 | Berkes et al. | |
| 2017/0056455 A1 | 3/2017 | Berkes et al. | |
| 2017/0128502 A1 | 5/2017 | Berkes et al. | |
| 2017/0196914 A1 | 7/2017 | Mckenzie et al. | |
| 2017/0196915 A1 | 7/2017 | Czarnecki-Maulden et al. | |
| 2017/0206504 A1 | 7/2017 | Taylor et al. | |
| 2017/0209504 A1 | 7/2017 | Goodman et al. | |
| 2017/0216377 A1 | 8/2017 | Berkes et al. | |
| 2017/0281699 A1 | 10/2017 | Berkes et al. | |
| 2017/0296600 A1 | 10/2017 | Rangavajla | |
| 2017/0312321 A1 | 11/2017 | Rubio Nistal et al. | |
| 2018/0000878 A1 * | 1/2018 | Goodman | A61K 35/747 |
| 2018/0071344 A1 | 3/2018 | Berry et al. | |
| 2018/0221422 A1 | 8/2018 | Keshtmand et al. | |
| 2020/0155620 A1 * | 5/2020 | Goodman | A61K 9/1658 |
| 2021/0100854 A1 * | 4/2021 | Goodman | A23L 33/195 |
| 2021/0290701 A1 * | 9/2021 | Besner | A61K 47/10 |

FOREIGN PATENT DOCUMENTS

| | | | | |
|---|---|---|---|---|
| JP | 2005-528324 A | 9/2005 | | |
| JP | 2006-512059 A | 4/2006 | | |
| JP | 2010-195786 A | 9/2010 | | |
| JP | 2010-535731 A | 11/2010 | | |
| JP | 2011-102250 A | 5/2011 | | |
| JP | 2011-201840 A | 10/2011 | | |
| JP | 2012-527898 A | 11/2012 | | |
| JP | 2013-510560 A | 3/2013 | | |
| JP | 2013-529893 A | 7/2013 | | |
| JP | 2017-508754 A | 3/2017 | | |
| WO | WO-02/077183 A2 | 10/2002 | | |
| WO | WO-03/083045 A2 | 10/2003 | | |
| WO | WO-2010/138522 A2 | 12/2010 | | |
| WO | WO-2011/000123 A1 | 1/2011 | | |
| WO | WO-2013/007742 A1 | 1/2013 | | |
| WO | WO-2013/088045 A1 | 6/2013 | | |
| WO | WO-2014/067976 A1 | 5/2014 | | |
| WO | WO-2015/134808 A2 | 9/2015 | | |
| WO | WO-2016/066763 A1 | 5/2016 | | |
| WO | WO-2016066763 A1 * | 5/2016 | | A61P 1/14 |
| WO | WO-2020028871 A1 * | 2/2020 | | A61K 35/742 |

OTHER PUBLICATIONS

Final Office Action dated Oct. 19, 2020, from U.S. Appl. No. 16/437,921.

Jacob K. Olson, et al., "An Enhanced Lactobacillus Reuteri Biofilm Formulation That Increases Protection Against Experimental Necrotizing Enterocolitis", Am. J: Physiol. Gastrointest. Liver Physiol. 315, May 31, 2018, pp. G408-G419.

Non-Final Office Action on U.S. Appl. No. 16/437,921 dated Mar. 12, 2020, 12 pages.

Smith et al., "Cystic Fibrosis Airway Epithelia Fail to Kill Bacteria Because of Abnormal Airway Surface Fluid," Cell, vol. 85, Apr. 19, 1996, pp. 229-236.

U.S. Notice of Allowance dated Jul. 23, 2021, from U.S. Appl. No. 16/437,921.

U.S. Office Action dated Feb. 19, 2021, from U.S. Appl. No. 16/449,320.

Wu et al. Development of dextran nanoparticles for stabilizing delicate proteins. Nanoscale Res Lett. Apr. 27, 2013;8(1):197.

Allaker et al., "Non-conventional therapeutics for oral infections," Virulence, vol. 6, No. 3, Apr. 2015, pp. 196-207.

Beer et al., "Poly (lactic-glycolic) acid copolymer encapsulation of recombinant adenovirus reduces immunogenicity in vivo," Gene Therapy, vol. 5, Jan. 5, 1998, pp. 740-746.

Ben et al., "Low level of galacto-oligosaccharide in infant formula stimulates growth of intestinal Bifidobacteria and Lactobacilli," World Journal of Gastroenterology, vol. 14, No. 42, Nov. 14, 2008, pp. 6564-6568.

Boyle et al., "Probiotics for the treatment of eczema: a systematic review", Clinical and Experimental Allergy, vol. 39, Apr. 27, 2009, pp. 1117-1127.

Braegger et al., "Supplementation of Infant Formula With Probiotics and/or Prebiotics: A systematic Review and Comment by the ESPGHAN Committee on Nutrition", JPGN, vol. 52, No. 2, Feb. 2011, pp. 239-250.

Chavarri et al., "Microencapsulation of a probiotic and prebiotic in alginate-chitosan capsules improves survival in simulated gastrointestinal conditions," International Journal of Food Microbiology, vol. 142, Jun. 22, 2010, pp. 185-189.

Chen et al., "Probiotics and the mechanism of necrotizing enterocolitis," Seminars in Pediatric Surgery, vol. 22, 2013, pp. 94-100.

Chen et al., "The effect of immobilization of probiotic Lactobacillus reuteri DPC16 in sub-100 μm microcapsule on food-borne pathogens", World J. Microbial. Biotechnol., vol. 28, No. 6, Mar. 30, 2012, pp. 2447-2452.

Cook et al., "Microencapsulation of a synbiotic into PLGA/alginate multiparticulate gels," International Jounral of Pharmaceutics, vol. 466, Mar. 20, 2014, pp. 400-408.

Cook et al., "Microencapsulation of probiotics for gastrointestinal delivery," Journal of Controlled Release, vol. 162, Jun. 11, 2012, pp. 56-67.

Cornaz Gudet et al., "Simple method of in vitro diffusion of nicotine across procine palatine mucosa", European Journal of Pharmaceutics and Biopharmaceutics, vol. 43, No. 3, Jan. 16, 1997, pp. 259-264.

(56) References Cited

OTHER PUBLICATIONS

Crittenden et al., "Synbiotic Microcapsules That Enhance Microbial Viability during Nonrefrigerated Storage and Gastrointestinal Transit", Applied and Environmental Microbiology, vol. 72, No. 3, Mar. 2006, 2280-2282.
Ex Part Quayle Action on U.S. Appl. No. 15/257,673 dated Sep. 5, 2018, 7 pages.
Extended European Search Report issued in EP 16825137.9 dated Feb. 14, 2019, 9 pages.
Extended European Search Report on EP Application No. 19154908.8 dated Sep. 18, 2019, 12 pages.
Final Office Action on U.S. Appl. No. 15/649,352 dated Apr. 5, 2019, 6 pages.
Final Office Action on U.S. Appl. No. 15/744,725 dated Dec. 17, 2018, 16 pages.
First Examination Report on AU Application No. 2019201644 dated May 21, 2020, 6 pages.
Francavilla et al., "Indications and Recommendations by Societies and Institutions for the Use of Probiotics and Prebiotics in Paediatric Functional Intestinal Disorders", JPGN, vol. 63, Supplemental 1, Jul. 2016, pp. S36-S37.
Goodman et al., "Biofilms can be dispersed by focusing the immune system on a common family of bacterial nucleoid-associated proteins," Mucosal Immunology, vol. 4, No. 6, Nov. 2011, pp. 625-637.
Gustave et al., "Targeting bacterial integration host factor to disrupt biofilms associated with cystic fibrosis," Journal of Cystic Fibrosis, vol. 12, No. 4, Nov. 17, 2012, pp. 384-389.
International Preliminary Report on Patentability on PCT Application No. PCT/US2015/019059 dated Sep. 15, 2016, 12 pages.
International Preliminary Report on Patentability on PCT Application No. PCT/US2018/024604 dated Oct. 10, 2019, 9 pages.
International Search Report and Written Opinion (ISA/EP) on PCT Application No. PCT/US2015/019059, dated Nov. 20, 2015, 18 pages.
International Search Report and Written Opinion (ISA/US) on PCT Application No. PCT/US2016/042153 dated Sep. 27, 2016, 9 pages.
International Search Report and Written Opinion (ISA/US) on PCT Application No. PCT/US2018/024604 dated Aug. 29, 2018, 13 pages.
International Search Report and Written Opinion for PCT Application No. PCT/US2019/057279 dated Jan. 15, 2020, 16 pages.
Justice et al., "Aberrant Community Architecture and Attenuated Persistence of Uropathogenic *Escherichia coli* in the Absence of Individual IHF Subunits," PLoS ONE, vol. 7, No. 10, Oct. 2012, pp. 1-11.
Kadajji et al., "Water Soluble Polymers for Pharmaceutical Applications," Polymers, vol. 3, Nov. 11, 2011, pp. 1972-2009.
Kumari et al., "Biodegradable polymeric nanoparticles based drug delivery systems," Colloids and Surfaces B: Biointerfaces, vol. 75, Sep. 8, 2009, pp. 1-18.
Lewis et al., "Dietary supplementation with Bifidobacterium lactis NCC2818 from weaning reduces local immunoglobin production in lymphoid-associated tissues but increases systemic antibodies in healthy neonates", British Journal of Nutrition, vol. 110, Mar. 11, 2013, pp. 1243-1252.
Liao et al., "Using probiotics to improve swine gut health and nutrient utilization", Animal Nutrition, vol. 3, Jul. 8, 2017, pp. 331-343.
Mackos et al., "Probiotic Lactobacillus reuteri Attenuates the Stressor-Enhanced Severity of Citrobacter rodentium Infection," Infection and Immunity, vol. 81, Sep. 2013, pp. 3253-3263.
Martin et al., "Probiotics: Role in Pathophysiology and Prevention in Necrotizing Enterocolitis," Seminars in Perinatology, vol. 32, 2008, pp. 127-137.
Mashburn-Warren et al., "Novel method for the depletion of cariogenic bacteria using dextranomer microspheres", Mol. Oral Microbial., May 9, 2017, pp. 475-489.
Navarro et al., "Enhanced Probiotic Potential of Lactobacillus reuteri When Delivered as a Biofilm on Dextranomer Microspheres That Contain Beneficial Cargo," Frontiers in Microbiology, vol. 8, No. 489, Mar. 27, 2017, pp. 1-15.
Non-Final Office Action on U.S. Appl. No. 15/257,673 dated Dec. 22, 2017, 23 pages.
Non-Final Office Action on U.S. Appl. No. 15/649,352 dated Oct. 15, 2018, 21 pages.
Non-Final Office Action on U.S. Appl. No. 15/744,725 dated May 17, 2018, 20 pages.
Notice of Allowance on U.S. Appl. No. 15/257,673 dated Mar. 22, 2019, 8 pages.
Notice of Allowance on U.S. Appl. No. 15/649,352 dated Dec. 23, 2019, 15 pages.
Office Action on JP 2016-555766 dated Feb. 10, 2020, 4 pages (English Translation).
Office Action on JP Application No. 2018-038713 dated Oct. 18, 2018, 4 pages (English Translation).
Official Action issued in JP Patent No. 2016-555766 dated Apr. 2, 2019, 10 pages (English Translation).
Official Action on JP Application No. 2016-555766 dated Oct. 18, 2018, 16 pages (English Translation).
Olson et al., "An enhanced Lactobacillus reuteri biofilm formulation that increases protection against experimental necrotizing enterocolitis", Am. J. Physiol. Gastrointest. Liver Physiol., vol. 315, Mar. 31, 2018, pp. G408-G419.
Olson et al., "Harvesting the benefits of biofilms: A novel probiotic delivery system for the prevention of necrotizing enterocolitis," Journal of Pediatric Surgery, vol. 51, Feb. 26, 2016, pp. 936-941.
Ornelas-Megiatto et al., "Aerosolized Antimicrobial Agents Based on Degradable Dextran Nanoparticles Loaded with Silver Carbene Complexes", Molecular Pharmaceutics, vol. 9, No. 11, Oct. 1, 2012, pp. 3012-3022.
Partial European Search Report issued in European Application No. 19154908.8 dated May 31, 2019, 13 pages.
Petreska Ivanovska et al., "Comparative evaluation of viability of encapsulated Lactobacillus easel using two different methods of microencapsulation," International Journal of Pharmaceutical and Phytopharmacological Research, vol. 4, No. 1, pp. 20-24 (Abstract only).
Pliszczak et al., "Improvement of an encapsulation process for the preparation of pro- and prebiotics-loaded bioadhesive microparticles by using experimental design," European Journal of Pharmaceutical Sciences, vol. 44, Jun. 25, 2011, pp. 83-92.
Reid et al., "How do probiotics and prebiotics function at distant sites?", Beneficial Microbes, vol. 8, No. 4, Apr. 16, 2017, pp. 521-533.
Restriction Requirement on U.S. Appl. No. 15/257,673 dated Jun. 26, 2017, 7 pages.
Rezaee et al., "Prebiotics Decrease the Antibacterial Effect of Nano Silver nd Nano TiO2 Particles Against Probiotic Bacteria of Food", Current Nutrition and Food Science, vol. 10, No. 2, Jul. 15, 2013, pp. 88-93.
Rocco et al., "Targeting the HUβ protein prevents porphyromonas gingivalis from entering into preexisting biofilms" Journal of Bacteriology, vol. 200, No. 11, Jun. 2018, pp. 1-11.
Roselli et al., "Immunomodulating effects of probiotics for microbiota modulation, gut heath and disease resistance in pigs," Animal Feed Science and Technology, vol. 233, Jul. 19, 2017, pp. 104-119.
Salas-Jara et al., "Biofilm forming Lactobacillus: New challenges for the development of Probiotics". Microorganisms, vol. 4, No. 35, Sep. 20, 2016, 14 pages.
Salmeron, "Fermented cereal beverages: from probiotic, prebiotic and synbiotic towards Nanoscience designed healthy drinks", Letters in Applied Microbiology, vol. 65, Mar. 31, 2017, pp. 114-124.
Sarmiento-Rubiano et al., "Dietary supplementation with sorbitol results in selective enrichment of lactobacilli in rat intestine," Research in Microbiology, vol. 158, Aug. 2, 2007, pp. 694-701.
Sathyabama et al., "Co-encapsulation of probiotics with prebiotics on alginate matrix and its effect on viability in simulated gastric environment," LWT—Food Science and Technology, vol. 57, Dec. 16, 2013, pp. 419-425.
Second Examination Report on AU Application No. 2015227075 dated Mar. 6, 2019, 7 pages.

(56) References Cited

OTHER PUBLICATIONS

Sultana et al., "Encapsulation of probiotic bacteria with alginate-starch and evaluation of survival in simulated gastrointestinal conditions and in yoghurt," International Journal of Food Microbiology, vol. 62, May 26, 2000, pp. 47-55.

Third Examination Report on AU Application No. 2015227075 dated Mar. 13, 2019, 6 pages.

Thurnheer et al., "Colonisation of gingival epithelia by subgingival biofilms in vitro: role of 'red complex' bacteria," Archives in Oral Biology, vol. 59, No. 9, Sep. 2014, pp. 1-24.

UniProtKB: TrEMBL A0A0E4BIL9. Putative DNA-binding protein HU, 2015, retrieved from www.uniprot.org/uniprot/A0A0E4BIL9.txt?version=3, 1 page.

Varshosaz, "The promise of chitosan microspheres in drug delivery systems", Expert Opinion on Drug Delivery, vol. 4, No. 3, May 9, 2007, pp. 263-273.

Woischnig et al., "High Affinity Native Human Monoclonal Antibody with Broad Cross-Species Biofilm Disrupting Activity" poster presented at ICAAC Meeting on Sep. 20, 2015, available at www.trellisbio.com/assets/docs/ICAAC%20Biofilm%20Poster%2020150920.pdf., 1 page.

Wu et al., "Preparation of sodium fluoride-loaded gelatin microspheres, characterization and cariostatic studies," J Microencapsul., vol. 21, No. 8, Dec. 2004, pp. 889-903, Abstract Only.

Desiderio, et al. "Intraphagocytic Killing of *Salmonella typhimurium* by Liposome-Encapsulated Cephalothin", The Journal of Infectious Diseases, vol. 148, No. 3, Sep. 1983, pp. 563-570.

U.S. Non-Final Office Action dated Feb. 3, 2022, from U.S. Appl. No. 16/437,921.

U.S. Final Office Action dated Sep. 20, 2021, from U.S. Appl. No. 16/449,320.

U.S. Notice of Allowance dated Oct. 15, 2021, from U.S. Appl. No. 16/437,921.

Ex Parte Quayle Action dated Apr. 28, 2022, from U.S. Appl. No. 16/449,320.

U.S. Notice of Allowance dated Jun. 1, 2022, from U.S. Appl. No. 16/437,921.

U.S. Notice of Allowance dated May 11, 2022, from U.S. Appl. No. 16/449,320.

\* cited by examiner

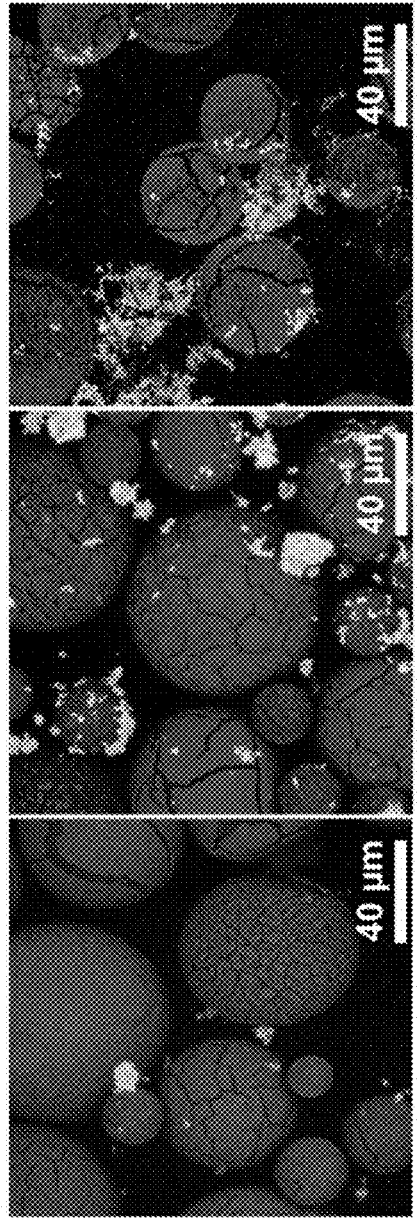
FIG. 6A
FIG. 6B
FIG. 6C
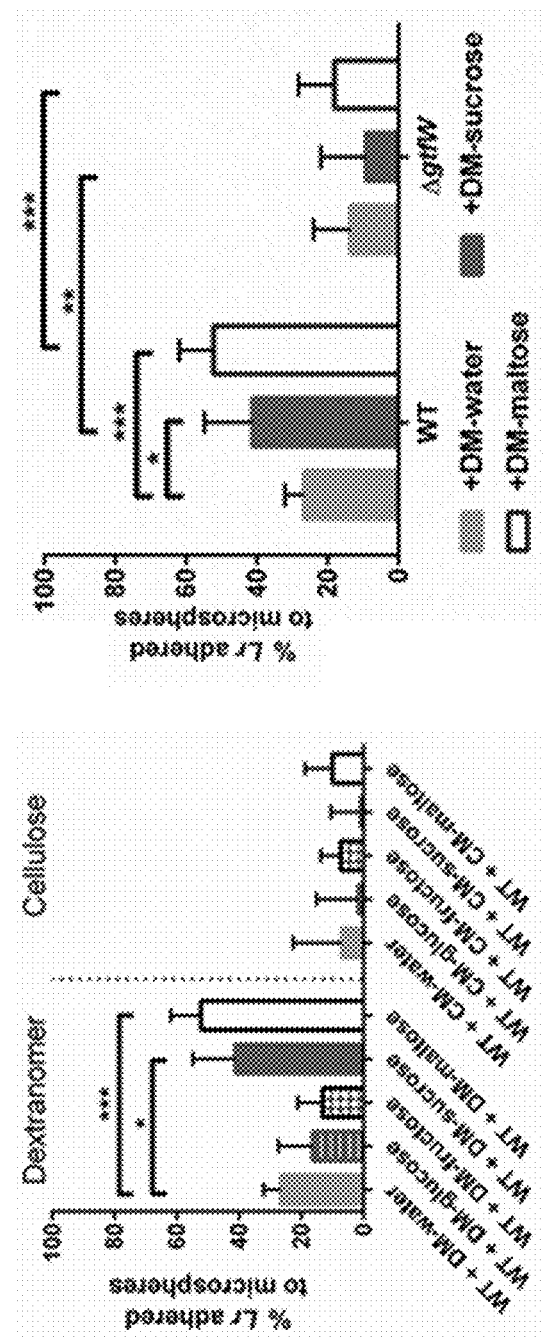
FIG. 7A
FIG. 7B ical response. It has been shown that probiotic biofilms can be grown on surfaces as a means to introduce bacteria into the site of wounds, where a formulation comprising a plaster or dressing based on a hydrocolloid that is a natural gelatin to treat wounds (i.e., EP2450062). However, there is an unmet need for fewer probiotic doses and greater efficacy of probiotic bacteria and its appropriate formulation. The compositions and methods as disclosed herein are provided to address this unmet need and, to the best of Applicants' knowledge, have not yet heretofore been disclosed.

SEQUENCE LISTING

<160> NUMBER OF SEQ ID NOS: 22

<210> SEQ ID NO 1
<211> LENGTH: 96
<212> TYPE: PRT
<213> ORGANISM: Haemophilus influenzae

<400> SEQUENCE: 1

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
            20                  25                  30

Glu Glu Ile Arg Leu Ser Leu Glu Ser Gly Gln Asp Val Lys Leu Ser
        35                  40                  45

Gly Phe Gly Asn Phe Glu Leu Arg Asp Lys Ser Ser Arg Pro Gly Arg
    50                  55                  60

Asn Pro Lys Thr Gly Asp Val Val Pro Val Ser Ala Arg Arg Val Val
65                  70                  75                  80

Thr Phe Lys Pro Gly Gln Lys Leu Arg Ala Arg Val Glu Lys Thr Lys
                85                  90                  95

<210> SEQ ID NO 2
<211> LENGTH: 136
<212> TYPE: PRT
<213> ORGANISM: Haemophilus influenzae

<400> SEQUENCE: 2

Met Arg Phe Val Thr Ile Phe Ile Asn His Ala Phe Asn Ser Ser Gln
1               5                   10                  15

Val Arg Leu Ser Phe Ala Gln Phe Leu Arg Gln Ile Arg Lys Asp Thr
            20                  25                  30

Phe Lys Glu Ser Asn Phe Leu Phe Asn Arg Arg Tyr Lys Phe Met Asn
        35                  40                  45

Lys Thr Asp Leu Ile Asp Ala Ile Ala Asn Ala Glu Leu Asn Lys
    50                  55                  60

Lys Gln Ala Lys Ala Ala Leu Glu Ala Thr Leu Asp Ala Ile Thr Ala
65                  70                  75                  80

Ser Leu Lys Glu Gly Glu Pro Val Gln Leu Ile Gly Phe Gly Thr Phe
                85                  90                  95

Lys Val Asn Glu Arg Ala Ala Arg Thr Gly Arg Asn Pro Gln Thr Gly
                100                 105                 110

Ala Glu Ile Gln Ile Ala Ala Ser Lys Val Pro Ala Phe Val Ser Gly
            115                 120                 125

Lys Ala Leu Lys Asp Ala Ile Lys
        130                 135

<210> SEQ ID NO 3
<211> LENGTH: 96
<212> TYPE: PRT
<213> ORGANISM: Haemophilus influenzae

<400> SEQUENCE: 3

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
            20                  25                  30

Glu Glu Ile Arg Leu Ser Leu Glu Ser Gly Gln Asp Val Lys Leu Ser
        35                  40                  45

```
Gly Phe Gly Asn Phe Glu Leu Arg Asp Lys Ser Ser Arg Pro Gly Arg
        50                  55                  60

Asn Pro Lys Thr Gly Asp Val Val Pro Val Ser Ala Arg Arg Val Val
 65                  70                  75                  80

Thr Phe Lys Pro Gly Gln Lys Leu Arg Ala Arg Val Glu Lys Thr Lys
                     85                  90                  95

<210> SEQ ID NO 4
<211> LENGTH: 99
<212> TYPE: PRT
<213> ORGANISM: Escherichia coli

<400> SEQUENCE: 4

Met Ala Leu Thr Lys Ala Glu Met Ser Glu Tyr Leu Phe Asp Lys Leu
 1               5                  10                  15

Gly Leu Ser Lys Arg Asp Ala Lys Glu Leu Val Glu Leu Phe Phe Glu
                20                  25                  30

Glu Ile Arg Arg Ala Leu Glu Asn Gly Glu Gln Val Lys Leu Ser Gly
            35                  40                  45

Phe Gly Asn Phe Asp Leu Arg Asp Lys Asn Gln Arg Pro Gly Arg Asn
        50                  55                  60

Pro Lys Thr Gly Glu Asp Ile Pro Ile Thr Ala Arg Arg Val Val Thr
 65                  70                  75                  80

Phe Arg Pro Gly Gln Lys Leu Lys Ser Arg Val Glu Asn Ala Ser Pro
                 85                 90                  95

Lys Asp Glu

<210> SEQ ID NO 5
<211> LENGTH: 100
<212> TYPE: PRT
<213> ORGANISM: Pseudomonas aeruginosa

<400> SEQUENCE: 5

Met Gly Ala Leu Thr Lys Ala Glu Ile Ala Glu Arg Leu Tyr Glu Glu
 1               5                  10                  15

Leu Gly Leu Asn Lys Arg Glu Ala Lys Glu Leu Val Glu Leu Phe Phe
                20                  25                  30

Glu Glu Ile Arg Gln Ala Leu Glu His Asn Glu Gln Val Lys Leu Ser
            35                  40                  45

Gly Phe Gly Asn Phe Asp Leu Arg Asp Lys Arg Gln Arg Pro Gly Arg
        50                  55                  60

Asn Pro Lys Thr Gly Glu Ile Pro Ile Thr Ala Arg Arg Val Val
 65                  70                  75                  80

Thr Phe Arg Pro Gly Gln Lys Leu Lys Ala Arg Val Glu Ala Tyr Ala
                85                  90                  95

Gly Thr Lys Ser
            100

<210> SEQ ID NO 6
<211> LENGTH: 96
<212> TYPE: PRT
<213> ORGANISM: Haemophilus influenzae

<400> SEQUENCE: 6

Met Ala Thr Ile Thr Lys Leu Asp Ile Ile Glu Tyr Leu Ser Asp Lys
 1               5                  10                  15

Tyr His Leu Ser Lys Gln Asp Thr Lys Asn Val Val Glu Asn Phe Leu
```

```
                    20                  25                  30

Glu Glu Ile Arg Leu Ser Leu Glu Ser Gly Gln Asp Val Lys Leu Ser
                35                  40                  45

Gly Phe Gly Asn Phe Glu Leu Arg Asp Lys Ser Ser Arg Pro Gly Arg
            50                  55                  60

Asn Pro Lys Thr Gly Asp Val Val Pro Val Ser Ala Arg Arg Val Val
65                  70                  75                  80

Thr Phe Lys Pro Gly Gln Lys Leu Arg Ala Arg Val Glu Lys Thr Lys
                85                  90                  95

<210> SEQ ID NO 7
<211> LENGTH: 90
<212> TYPE: PRT
<213> ORGANISM: Escherichia coli

<400> SEQUENCE: 7

Met Asn Lys Thr Gln Leu Ile Asp Val Ile Ala Glu Lys Ala Glu Leu
1               5                   10                  15

Ser Lys Thr Gln Ala Lys Ala Ala Leu Glu Ser Thr Leu Ala Ala Ile
                20                  25                  30

Thr Glu Ser Leu Lys Glu Gly Asp Ala Val Gln Leu Val Gly Phe Gly
                35                  40                  45

Thr Phe Lys Val Asn His Arg Ala Glu Arg Thr Gly Arg Asn Pro Gln
            50                  55                  60

Thr Gly Lys Glu Ile Lys Ile Ala Ala Ala Asn Val Pro Ala Phe Val
65                  70                  75                  80

Ser Gly Lys Ala Leu Lys Asp Ala Val Lys
                85                  90

<210> SEQ ID NO 8
<211> LENGTH: 90
<212> TYPE: PRT
<213> ORGANISM: Escherichia coli

<400> SEQUENCE: 8

Met Asn Lys Ser Gln Leu Ile Asp Lys Ile Ala Ala Gly Ala Asp Ile
1               5                   10                  15

Ser Lys Ala Ala Ala Gly Arg Ala Leu Asp Ala Ile Ile Ala Ser Val
                20                  25                  30

Thr Glu Ser Leu Lys Glu Gly Asp Asp Val Ala Leu Val Gly Phe Gly
                35                  40                  45

Thr Phe Ala Val Lys Glu Arg Ala Ala Arg Thr Gly Arg Asn Pro Gln
            50                  55                  60

Thr Gly Lys Glu Ile Thr Ile Ala Ala Ala Lys Val Pro Ser Phe Arg
65                  70                  75                  80

Ala Gly Lys Ala Leu Lys Asp Ala Val Asn
                85                  90

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcgtggcggc cgccattatt ttcatgtagt gtattt                              36
```

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcgtggtcga ccttttttat gtccataatc tatt                                 34

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcgtggtcga cgaaaatatt taatatgaaa atga                                 34

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcgtgctcga gccaagcact atttcacgag aat                                  33

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcgtggtcga cgatgaaaat ttgtttgatt t                                    31

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcgtggtcga cttataaaag ccagtcatta g                                    31

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gcgtgctcga gcaacaagag tatcagggta aagc                                 34

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 16
gcgtggtcga ctccttccca atagatgatt gatt                                  34

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 17
gcgtggtcga catggtaaaa cgtgaaaaaa atgt                                  34

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 18
gcggccgctc cgccagcttt ttctaataac t                                     31

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 19
gcgtggctag catgaacctg ccaacaattc ctaa                                  34

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 20
gcgtggctct tccgcattaa atattttctt ggttt                                 35

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 21
gcgtgctcga gcgcaacaaa tacagtttct aata                                  34

<210> SEQ ID NO 22

```
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gcgtggtcga caaacctcct gataatttac aagt                                   34
```

PREBIOTIC FORMULATIONS

CROSS-REFERENCE TO RELATED APPLICATIONS

This application is a continuation of U.S. application Ser. No. 15/649,352, filed Jul. 13, 2017, issued as U.S. Pat. No. 10,624,934 on Apr. 21, 2020, which is a continuation-in-part of U.S. application Ser. No. 15/257,673, filed Sep. 6, 2016, issued as U.S. Pat. No. 10,369,176 on Aug. 6, 2019, which is a continuation of International Application No. PCT/US2015/019059, filed Mar. 5, 2015, which in turn claims priority under 35 U.S.C. § 119(e) to U.S. Provisional Application No. 61/949,058, filed Mar. 6, 2014. U.S. application Ser. No. 15/649,352 also claims priority under 35 U.S.C. § 119(e) to U.S. Provisional Application No. 62/477,382, filed Mar. 27, 2017. The contents of each of these applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Dec. 21, 2020, is named 106887-0180_SL.txt and is 11,118 bytes in size.

TECHNICAL FIELD

This disclosure relates to novel probiotic formulations and methods for using same for treating or preventing disease.

BACKGROUND

Probiotics, are live microbes that when ingested in high enough quantities confer a health benefit for the host (Food and Agriculture Organization of the United Nations and World Health Organization, "Health and Nutritional Properties of Probiotics in Food Including Powdered Milk with Live Bacteria" (2001)), are gaining traction as a viable option for treating enteric diseases (Hemarajata and Versalovic, (2013) Effects of Probiotics on Gut Microbiota: Mechanisms of Intestinal Immunomodulation and Neuromodulation, Therap Adv Gastroenterol, 6:39-51).

Under the right conditions, many probiotics can effectively prevent pathogen colonization due to either direct (e.g., production of antimicrobial defenses) or indirect (e.g., stimulation of host defenses) mechanisms. Few probiotic species are able to both prevent pathogen colonization and limit excessive inflammatory responses. This is important, however, because excessive colonic inflammation in response to colonic infection can lead to the development of protracted illness, such as post-infectious irritable bowel syndrome. Thus, the development of probiotics that are able to prevent excessive immune responses to colonic pathogens, while still maintaining anti-bacterial immunity would have the ability to prevent both short-term and longer-term health effects of enteric infection. This disclosure provides formulations that address this unmet need and provides related advantages as well.

SUMMARY

Aspects and embodiments of this technology combine the health benefits of probiotic bacteria with prebiotic substances to help stimulate the exclusive growth of the probiotic species and, in one aspect, provide the bacteria in the form of a biofilm on a biocompatible microsphere. Applicants have discovered that the use of a biofilm on the microsphere provides enhanced efficacy and duration of the therapeutic response. It has been shown that probiotic biofilms can be grown on surfaces as a means to introduce bacteria into the site of wounds, where a formulation comprising a plaster or dressing based on a hydrocolloid that is a natural gelatin to treat wounds (i.e., EP2450062). However, there is an unmet need for fewer probiotic doses and greater efficacy of probiotic bacteria and its appropriate formulation. The compositions and methods as disclosed herein are provided to address this unmet need and, to the best of Applicants' knowledge, have not yet heretofore been disclosed.

This technology also provides methods of formulation, which enhance the efficiency and durability of introducing probiotic strains at a site of action. It specifically bypasses the rate limiting step of biofilm formation. This technology is useful for gastrointestinal gut health and any aspect where probiotic bacteria need to establish, e.g., the gastrointestinal tract, wound healing, skin, vaginal, oral, agriculture, and water purification.

In the context of gastrointestinal health specifically and the environment in general, probiotics are a natural way to protect and restore gut microbiota to a healthy state. Unfortunately, even under optimal conditions, probiotic bacteria (as typically delivered) fail to establish, or sufficiently persist, minimizing the magnitude and duration of their healthful effects. One of the rate limiting steps is the capacity of introduced bacteria to form a lasting biofilm. When bacteria are already in the form of a biofilm (a surface adhered community) as opposed to planktonic (free-living), they more readily establish and persist. The positive effects of probiotic bacteria can be enhanced by providing them in a biofilm state; this can readily be accomplished by growing the bacteria on the surface of a biocompatible and non-toxic microsphere and associated with a biofilm. Biocompatible microspheres can be biodegradable polymers, non-biodegradable polymers, a metal, or a combination thereof. When this surface is in the form of a microsphere, prebiotic and/or prebiofilmic substances can be added as cargo to facilitate establishment and maintenance of the probiotic bacterial biofilm.

The biofilm-generating probiotic bacterium adheres to the surface of the biocompatible microsphere and generates a biofilm. The biocompatible microsphere is semi-permeable or porous, and has either a solid or hollow core. When the biocompatible microsphere has a hollow core, it can carry a prebiotic and any nutritional supplementation for the probiotic bacterium as a cargo whereby the bacterium gains access via diffusion from the lumen. The microsphere can also carry a drug, or a compound, or an agent, which is selective against a pathogen, that in one aspect, may compete with the health-inducing bacterium in the composition. In a further aspect, the microsphere can carry chemical reductants and/or molecules and or surfaces that promote adsorption (in the core or on the surface of the microsphere) and/or molecules and/or surfaces that promote absorption (in the core or on the surface of the microsphere). In addition to a biocompatible microsphere, biofilm-generating probiotic and prebiotic, a novel probiotic formulation can also contain a prebiofilmic, which is a substance that supports biofilm formation and/or durability, and in one aspect, the prebiofilmic is a DNA binding polypeptide or protein and/or a DNABII polypeptide or protein or a fragment thereof that supports biofilm formation and/or durability. The prebiotic is released from the hollow core and to adhere to the bacterium. This occurs because the surface of the microsphere is porous or semi-permeable, and the prebiotic releases by diffusion or the microsphere slowly degrades causing leaks and again diffusion from the microsphere. Release of the prebiotic from the hollow core can be regulated by varying microsphere size (smaller microspheres release faster), and/or by altering the viscosity of the prebiotic (i.e., the higher the viscosity the slower the release).

Microspheres have added value in ideally providing diffusible prebiotic (nutritional supplementation specific/exclusive to probiotic bacteria) cargo that can help promote probiotic bacterial establishment and survival while limiting pathogenic bacterial challenge. At least for the probiotic bacterium *Lactobacillus reuteri*, the biofilm state is advantageous in establishing in the gut over the same bacteria in planktonic form. Furthermore, *L. reuteri* introduced into mice as biofilms are shown to have a more robust and durable prophylactic effect on the pathogenesis of the enteropathogenic bacterium, *Citrobacter rodentium*, than *L. reuteri* in its planktonic form. Based on these results, highly integrated examples are provided that yield novel formulations of probiotics that provide greater and more lasting effects against dysbiosis preventing or even treating gut pathogenesis with a far reduced need for patient compliance.

In view of the above advantages, provided herein is a composition comprising, or alternatively consisting essentially of, or yet further consisting of, a biocompatible microsphere, a biofilm-generating probiotic bacterium and a prebiotic, wherein the prebiotic comprises, or alternatively consisting essentially of, or yet consisting of, a nutritional supplementation for the probiotic bacterium. In one aspect, the composition further comprises, or alternatively consists essentially of, or yet further consisting of, a carrier, such as a pharmaceutically acceptable carrier or a biocompatible scaffold.

The compositions are formulated for in vivo or ex vivo use. For use in vivo, the compositions are formulated for administration orally, vaginally, nasally (inhalation), intravenously or intramuscularly (injectable), topically, as a suppository, as a spray (aerosol administration), dry application by admixing in the soil, as a solute (for admixing with an aqueous environment). In one aspect, they are formulated in a dosage form. Suitable dosage forms include, but are not limited to a suppository, a powder, a liquid, a capsule, a chewable tablet, a swallowable tablet, a buccal tablet, a troche, a lozenge, a soft chew, a solution, a suspension, a spray, a tincture, a decoction, an infusion, and combinations thereof.

This disclosure also provides a method for preparing the above-noted composition, the method comprising, or alternatively consisting essentially of, or yet further consisting of, admixing a biocompatible microsphere with a biofilm-generating probiotic bacterium, a prebiotic, and in one aspect, further admixing a prebiofilmic. In a further aspect, the method further comprises, or alternatively consists essentially of, or yet further consists of, admixing an effective amount of one or more of: a nutritional supplement for the probiotic bacterium, a drug active against a pathogen or invertebrate, or a chemical reductant and/or molecule that promote adsorption (in the core or on the surface of the microsphere) and/or molecules that promote absorption (in the core or on the surface of the microsphere).

This disclosure also provides therapeutic, industrially and agricultural use of the compositions as disclosed herein.

In some embodiments, a kit is provided comprising, or alternatively consisting essentially of, or yet consisting of, a composition as described herein and instructions for use diagnostically, industrially, in agriculture or therapeutically.

BRIEF DESCRIPTION OF THE FIGURES

FIGS. 6A-6C show that *L. reuteri* binds to dextranomer microspheres. Confocal laser scanning microscopy (CLSM) of *L. reuteri* adhered to DMs. (FIG. 6A) Water-filled DMs, (FIG. 6B) sucrose-filled DMs, (FIG. 6C) maltose-filled DMs after incubation with *L. reuteri* for 30 minutes showed that *L. reuteri* adherence to DMs can be enhanced to incorporate biofilm-promoting cargo within the DM lumen (green: bacteria stained with SYTO 9, red: DMs stained with Congo Red).

FIGS. 7A-7C show that microsphere composition and lumen cargo affected *L. reuteri* adherence, *L. reuteri* adhered to DMs in GTFW-dependent manner, and bacteria lacking GTF did not bind to DMs. A spin column assay was performed to assess relative bacterial adherence to microspheres. Bacteria were incubated for 5 minutes with 5 mg of microspheres, centrifuged at 100×g to separate bound and unbound bacteria, then CFU of non-adhered bacteria was quantified in the flow-through of the spin column. (FIG. 7A) Microspheres composed of either cross-linked dextran (DM) or cross-linked cellulose (CM) were filled with water, growth medium, or various sugars at a concentration of 1M to determine which microsphere type supported greatest adherence of L. reuteri. (FIG. 7B) Relative WT and ΔgtfW L. reuteri adherence to DM showed that L. reuteri adhered to DMs in a GTF-dependent manner. (FIG. 7C) Non-GTF expressing bacteria were similarly tested for microsphere adherence with water-loaded and sucrose-loaded DMs. Error bars represent standard error of the mean. Statistical significance is indicated by the following: *$P<0.05$, $P<0.01$, *$P<0.0005$.

(FIG. 11A) L. reuteri WT and ΔgtfW adhered as a biofilm on DMs that contained either water, sucrose (1M), or maltose (1M), or the equivalent volume of sugar alone (without DMs), were examined for relative adherence to human colonic DLD-1 cells after incubation for 60 minutes. Significantly more WT adhered to DLD-1 cells when delivered as a biofilm on the surface of DMs that contained sucrose or maltose, compared to water-filled DMs or the equivalent volume of sugar alone. Significantly fewer ΔgtfW mutant cells adhered to DLD-1 cells, regardless of cargo, which indicated that the GTFW protein contributes to L. reuteri adherence. (FIG. 11B) Adherence of WT to fetal small intestinal FHs 74 cells after 60 minute incubation showed that providing L. reuteri adherent on the DM surface as a biofilm with either sucrose or maltose as cargo resulted in greater adherence to intestinal cells. Error bars represent standard error of the mean. Statistical significance is indicated by the following: *$P<0.05$, $P<0.01$, *$P<0.001$, ****$P<0.0001$.

(FIG. 12A) In vitro CLSM of DLD-1 epithelial cells (blue, DAPI), L. reuteri (green, CF SE), and DMs (red, Congo Red). WT L. reuteri (top four rows) compared to ΔgtfW L. reuteri (middle four rows) and no L. reuteri (bottom row). Bacteria and DMs were pre-stained, incubated for 1 hour on pre-stained DLD-1 epithelial cells, washed three times, and fixed for CLSM analysis. (FIG. 12B) Comparison of bacterial biomass quantified via COMSTAT analysis of the green channel of CLSM images of WT and ΔgtfW L. reuteri. WT without DMs (n=10) resulted in less total bacterial signal compared to either WT+DM-sucrose (n=10) or WT+DM-maltose (n=10). ΔgtfW showed no difference in relative number of bacteria adhered to DLD-1 cells, regardless of the presence of DMs. Error bars represent standard error of the mean. Statistical significance is indicated by the following: *$P<0.05$, **$P<0.01$.

(FIG. 15A) A gtfW transcriptional reporter was constructed by fusing the click beetle luciferase downstream of the gtfW promoter on a plasmid, followed by introduction into L. reuteri (strain LMW 501). Expression of gtfW was monitored throughout growth in MRS, with or without the indicated additions by removing a 100 µl aliquot every hour, and measuring the $OD_{600\ nm}$. An additional 80 µl aliquot was removed and added to 20 µl of 2 mM D-luciferin and allowed to incubate at RT for 5 min, followed by luminescence detection. (FIG. 15B) GTFW enzymatic activity. Proteins extracted from *S. mutans*, *L. reuteri* WT, *L. reuteri* ΔgtfW (strain LMW 500), and *E. coli* harboring gtfW on an inducible plasmid (Ec) (strain LMW 502), were subjected to SDS-PAGE followed by PAS staining to examine GTFW enzymatic activity. 5% sucrose or 5% maltose were used as substrates. The arrows indicate GTFW activity.

(FIG. 16A) CLSM of *L. reuteri* biofilms at 1, 3, and 6 hours showed significantly more bacteria present and increased aggregation of WT bacteria in conditions with either sucrose or maltose at 1 hour compared to the gtfW mutant (left column), which was confirmed by quantification of the green fluorescent signal (FIG. 16B). The GTF-dependent increase in biofilm with sucrose or maltose present was increased after 3 hours (FIG. 16A—middle column, & FIG. 16C) and further increased after 6 hours (FIG. 16A—right column, & FIG. 16D). The gtfW mutant, being unable to utilize either maltose for biofilm formation, still benefited from sucrose in the growth medium after 1 hour, likely due to increased growth rate (data not shown). Error bars represent standard error of the mean. Statistical significance is indicated by the following: *P<0.05, **P<0.01.

FIG. 22A is H&E stained intestinal tissue sections demonstrating the following grades of histologic injury: Grade 0, no visible histological villus damage; Grade 1, distal villus enterocyte detachment; Grade 2, sloughing of enterocytes to the mid villus level; Grade 3, loss of the entire villus with preservation of the crypts; and Grade 4, transmural necrosis. Grade 2 injury and above is consistent with histologic NEC. All images are 20× magnification. FIG. 22B shows that rat pups were delivered prematurely, subjected to the experimental NEC protocol, and sacrificed when signs of clinical NEC developed or after 96 h. Each dot represents a single rat pup with their histologic injury score depicted. NEC incidence for each experimental group of pups is indicated. *p<0.05.

DETAILED DESCRIPTION

Figure 1A:
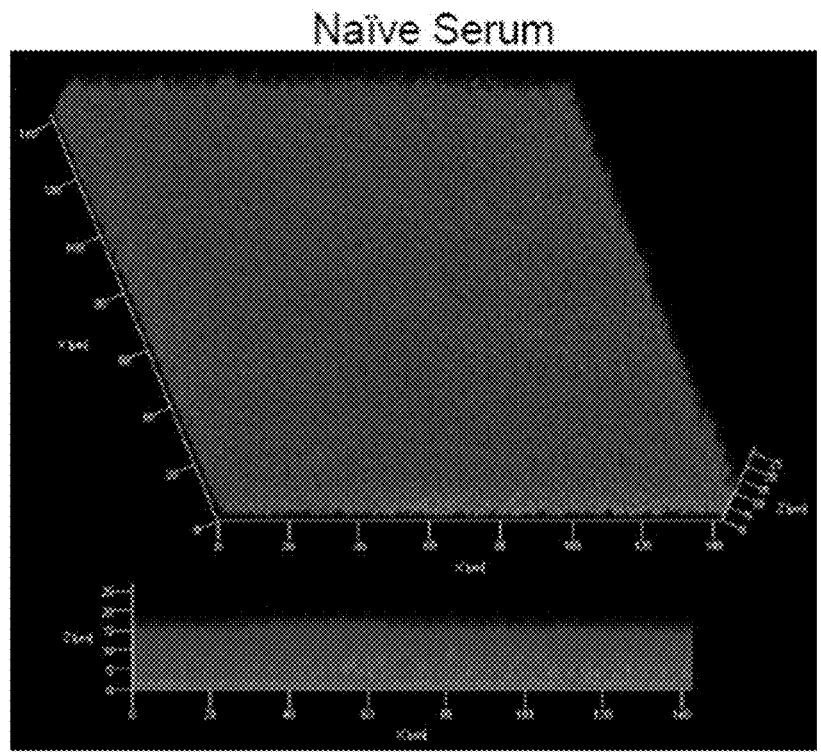
FIGS. 1A and 1B illustrate that *L. reuteri* biofilm structural integrity relies on the presence of DNABII family proteins. Confocal microscopy images of in vitro *L. reuteri* biofilms stained with LIVE/DEAD BacLight Bacterial Viability Kit (Molecular Probes). *L. reuteri* biofilms were grown for 24 hours at 37° C. and 5% CO2, at which time they were treated with a 1:50 dilution of either (FIG. 1A) rabbit naïve serum, (FIG. 1B) rabbit anti-integration host factor polypeptide ("IHF"), or media with nothing added (data not shown) for 16 hours. Anti-IHF treatments resulted in a 20% decrease in maximum height, 35% decrease in average thickness, and 41% decrease in biomass (data not shown).
Figure 1B:
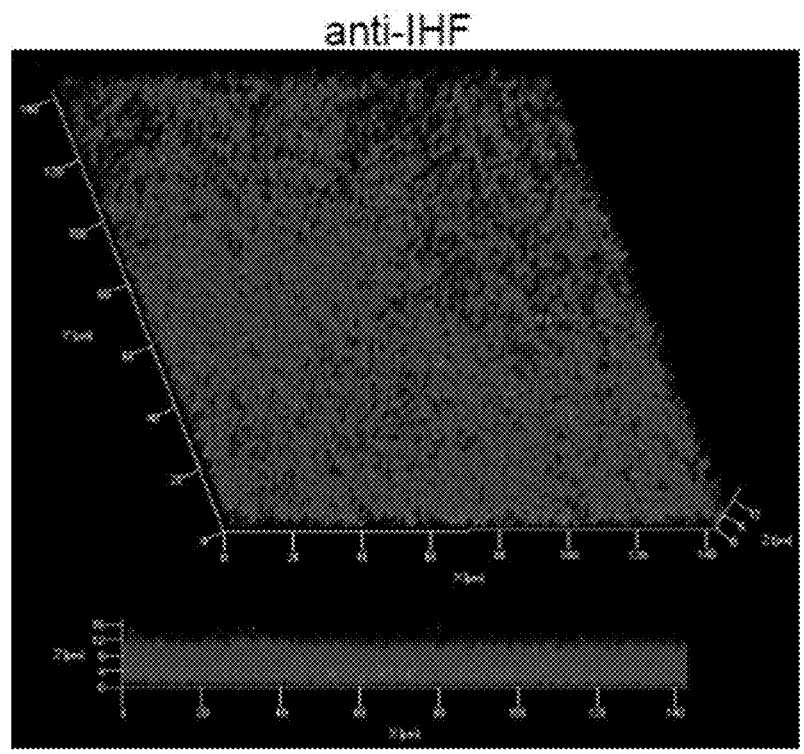
Figure 2:
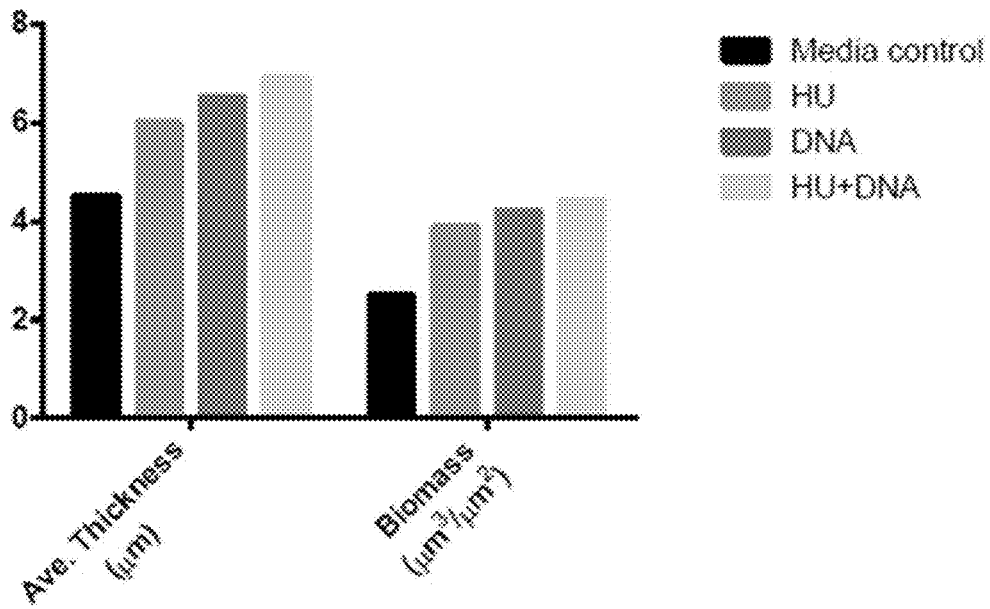
FIG. 2 illustrates that prebiotic compounds increase probiotic biofilms in average thickness and biomass. Addition of 10 µg/ml *S. mutans* HU to *L. reuteri* biofilm at time of seeding increased average thickness and biomass 33%, and 55%, respectively. Addition of 10 µg/ml calf thymus DNA increased average thickness 44% and biomass 68%. Adding 10 µg/ml of HU and DNA together led to an increased effect compared to either alone, with average thickness increasing 53% and biomass increasing 78%.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All technical and patent publications cited herein are incorporated herein by reference in their entirety. Nothing herein is to be construed as an admission that the invention is not entitled to antedate such disclosure by virtue of prior invention.

The practice of the present technology will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration and molecular weight, including ranges, are approximations which are varied (+) or (−) by increments of 1.0 or 0.1, as appropriate, or alternatively by a variation of +/−15%, or alternatively 10%, or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a bacterium" includes a plurality of bacteria, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention. Embodiments defined by each of these transition terms are within the scope of this invention.

A "biofilm" intends a thin layer or an organized community of microorganisms that at times can adhere to the surface of a structure, that may be organic or inorganic, together with the polymers, such as DNA, that they secrete and/or release. The biofilms are very resistant to microbiotics and antimicrobial agents. They live on gingival tissues, teeth, and restorations, causing caries and periodontal disease, also known as periodontal plaque disease. They also cause chronic middle ear infections. Biofilms can also form on the surface of dental implants, stents, catheter lines and contact lenses. They grow on pacemakers, heart valve replacements, artificial joints and other surgical implants. The Centers for Disease Control estimate that over 65% of nosocomial (hospital-acquired) infections are caused by biofilms. Fungal biofilms also frequently contaminate medical devices. They cause chronic vaginal infections and lead to life-threatening systemic infections in people with hobbled immune systems. Biofilms also are involved in numerous diseases. For instance, cystic fibrosis patients have *Pseudomonas* infections that often result in antibiotic resistant biofilms.

A "prebiotic" intends a nutritional supplement for the probiotic bacterium. Prebiotics are food ingredients, for example, oligosaccharides, that are non-digestible by a subject (e.g., by a mammal such as a human), and that stimulates the growth or activity of one or more beneficial bacteria and/or inhibit the growth or activity of one or more pathogenic bacteria. A prebiotic may selectively stimulate the growth and/or activity of one or a limited number of bacteria in the subject.

A "prebiofilmic" intends a substance that supports biofilm formation and durability, for example the prebiofilmic can be a substance that supports the extracellular matrix of the biofilm like an eDNA binding polypeptide or protein or alternatively a substrate that can be converted into a substance that facilitate adhesion, e.g., sucrose.

A "DNABII polypeptide or protein" intends a DNA binding protein or polypeptide that is composed of DNA-binding domains and thus have a specific or general affinity for DNA. In one aspect, they bind DNA in the minor grove. Non-limiting examples of DNABII proteins are an integration host factor (IHF) protein and a histone-like protein from *E. coli* strain U93 (HU), examples of which are provided in the attached sequence listing and additional strains and polypeptides are provided in Table 4. Also intended are polypeptide fragments and equivalent polypeptides that have amino acid modifications that do not substantially change the biological activity of the protein or polypeptides, or active fragment thereof. Active fragments can include, for example, the c-terminal half or c-terminal third of the protein or polypeptide. Other DNA binding proteins that can be associated with the biofilm include DPS (Genbank Accession No.: CAA49169), H-NS (Genbank Accession No.: CAA47740), Hfq (Genbank Accession No.: ACE63256), CbpA (Genbank Accession No.: BAA03950) and CbpB (Genbank Accession No.: NP 418813), as well as equivalent polpyeptides and active fragments thereof.

A "microsphere" intends a porous and/or semi-permeable biofilm-carrying and/or compound-carrying (e.g., drug-carrying) particulate or granular material within the particular size range recited. As used herein, a microsphere consisting of particles 50 millimeters or less in diameter, and about 1 micron or more (e.g., about 1 to about 100 or alternatively, or alternatively, about 1 to about 75 microns, or alternatively about 1 to about 50, or alternatively about 1 to about 25, or alternatively about 1 to about 10 microns, or alternatively about 0.5 to about 200 microns, or alternatively about 0.5 to about 700 microns, or alternatively about 1 to about 600 microns, or alternatively less than about 700 microns, or alternatively less than about 600 microns, or alternatively less than 500 microns, or alternatively less than about 400 microns, or alternatively less than about 300 microns, or alternatively less than about 200 microns, or alternatively less than about 100 microns) in diameter. Non-limiting examples of such include hollow microspheres that are porous and/or semi-permeable, and can, in some aspects, contain a pharmaceutical or a drug, microcapsules, (in which the excipient forms a skin or shell that surrounds and contains a cargo, such as a drug, a chemical reductant, or absorptive or adsorptive molecules), and microparticles, which are used as a generic term for any particles in the recited size range, whether spherical or not, as those terms are typically used in the art. Table 6 provides non-limiting examples of microspheres that are commercially available and their characteristics.

A "biodegradable polymer" intends polymers that are biocompatible and can degrade in vivo by bodily processes to products that are readily disposable by the body and should not accumulate in the body.

By "biocompatible", it is meant that the components of the delivery system will not cause tissue injury or injury to the human biological system. To impart biocompatibility, polymers and excipients that have had history of safe use in humans or with GRAS (Generally Accepted As Safe) status, are preferentially used. By biocompatibility, it is meant that the ingredients and excipients used in the composition will ultimately be "bioabsorbed" or cleared by the body with no adverse effects to the body. For a composition to be biocompatible, and be regarded as non-toxic, it must not cause toxicity to cells. Similarly, the term "bioabsorbable" refers to microspheres made from materials which undergo bioabsorption in vivo over a period of time such that long term accumulation of the material in the patient is avoided. The biocompatible nanoparticle is bioabsorbed over a period of less than 2 years, preferably less than 1 year and even more preferably less than 6 months. The rate of bioabsorption is related to the size of the particle, the material used, and other factors well recognized by the skilled artisan. A mixture of bioabsorbable, biocompatible materials can be used to form the microspheres used in this invention.

An "integration host factor" or "IHF" protein is a bacterial protein that is used by bacteriophages to incorporate their DNA into the host bacteria. These are DNA binding proteins that function in genetic recombination as well as in transcription and translational regulation. They also bind extracellular microbial DNA. The genes that encode the IHF protein subunits in E. coli are himA (Genbank accession No.: POA6X7.1) and himD (POA6Y1.1) genes. Non-limiting examples of such are provided in the attached sequence listing and noted in Table 4.

"HU" or "histone-like protein from E. coli strain U93" refers to a class of heterodimeric proteins typically associated with E. coli. HU proteins are known to bind DNA junctions. Related proteins have been isolated from other microorganisms. The complete amino acid sequence of E. coli HU was reported by Laine et al. (1980) Eur. J. Biochem. 103(3):447-481. Antibodies to the HU protein are commercially available from Abcam. Non-limiting examples of such are provided in the attached sequence listing.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

A "c-terminal polypeptide" intends the c-terminal half or c-terminal third of a polypeptide. As an example, for polypeptides containing 90 amino acids, the c-terminal polypeptide would comprise amino acids 46 through 90 or amino acids 60 through 90. In another aspect, the term intends the c-terminal 20 amino acids from the carboxy terminus.

A "n-terminal polypeptide" intends the n-terminal half of a polypeptide. As an example, for polypeptides containing 90 amino acids, the c-terminal polypeptide would comprise amino acids 1 through 45. In another aspect, the term intends the c-terminal 20 amino acids from the amino terminus.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides, antibodies and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

Glucotransferases are enzymes that establish glycosidic linkages. A non-limiting example of a sequence of the GTF protein is available at DSM 20016. gtfW ABQ83597.1 is provided at DSM 17938 gtfA WP_003671465. See also, Walter et al. (2008) Microbiology 154(Pt 1):72-80.

It is to be inferred without explicit recitation and unless otherwise intended, that when the present invention relates to a polypeptide, protein, polynucleotide or antibody, an equivalent or a biologically equivalent of such is intended within the scope of this invention. As used herein, the term "biological equivalent thereof" is intended to be synonymous with "equivalent thereof" when referring to a reference protein, antibody, polypeptide, polynucleotide or nucleic acid, intends those having minimal homology while still maintaining desired structure or functionality. Unless specifically recited herein, it is contemplated that any nucleic acid, polynucleotide, polypeptide or protein mentioned herein also includes equivalents thereof. For example, an equivalent intends at least about 70%, or alternatively 80% homology or identity and alternatively, at least about 85%, or alternatively at least about 90%, or alternatively at least about 95%, or alternatively 98% percent homology or identity across the protein or a particular fragment thereof, and exhibits substantially equivalent biological activity to the reference protein, polypeptide or nucleic acid.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; =10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

A "subject" or "patient" of diagnosis or treatment is a cell or an animal such as a mammal or a human. Non-human animals subject to diagnosis or treatment and are those subject to infections or animal models, for example, simians, murines, such as, rats, mice, chinchilla, canine, such as dogs, leporids, such as rabbits, livestock, sport animals and pets.

As used herein, the terms "treating," "treatment" and the like are used herein to mean obtaining a desired pharmacologic and/or physiologic effect. The effect may be prophylactic in terms of completely or partially preventing a disorder or sign or symptom thereof and/or may be therapeutic in terms of a partial or complete cure for a disorder and/or adverse effect attributable to the disorder.

To "prevent" intends to prevent a disorder or effect in vitro or in vivo in a system or subject that is predisposed to the disorder or effect. Examples of such is preventing the formation of a biofilm in a system that is infected with a microorganism known to produce one or alternatively, prevent a gastrointestinal disorder by supporting a healthy state of the patient's gut.

The term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

"Pharmaceutically acceptable carriers" refers to any diluents, excipients or carriers that may be used in the compositions of the invention. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like and consistent with conventional pharmaceutical practices.

A "biocompatible scaffold" refers to a scaffold or matrix for with the ability to support biofilm proliferation upon administration to a subject. In other embodiments, a biocompatible scaffold is a precursor to an implantable device which has the ability to perform its intended function, with the desired degree of incorporation in the host, without eliciting an undesirable local or systemic effects in the host. Biocompatible scaffolds are described in U.S. Pat. Nos. 6,638,369 and 8,815,276. In one aspect, the microsphere as described herein is a biocompatible scaffold.

"Administration" intends the delivery of a substance to a subject such as an animal or human. Administration can be effected in one dose, continuously or intermittently throughout the course of treatment. Methods of determining the most effective means and dosage of administration are known to those of skill in the art and will vary with the composition used for therapy, the purpose of the therapy, as well as the age, health or gender of the subject being treated. Single or multiple administrations can be carried out with the dose level and pattern being selected by the treating physician or in the case of pets and animals, treating vetrenarian. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and the target cell or tissue. Non-limiting examples of route of administration include oral administration, vaginal, nasal administration (inhalation), injection, topical application and by suppository.

The term "effective amount" refers to a quantity sufficient to achieve a beneficial or desired result or effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of a therapeutic composition, in some embodiments the effective amount is the amount sufficient to result in a protective response against a pathogen or alternatively to support a healthy state of being. In some embodiments, the amount is sufficient to accomplish one or more of 1) clear pathogen; 2) restore healthy microbiota; 3) modulate the immune system; 4) maintain metabolism and metabolic pathways; 5) reduce toxic compounds in the environment (toxic compounds in water, soil, air, and compounds such as heavy metals (e.g., chromium, arsenic, mercury, radioactive actinides, uranium, plutonium, thorium, polycyclic aromatic hydrocarbons (PAH), petroleum hydrocarbon, crude oil, refined oil, herbicide contamination or pesticide contamination); and 6) remediate a biofilm).

In the case of an in vitro or ex vivo applications, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The agents and compositions can be used in the manufacture of medicaments and for the treatment of humans and other animals by administration in accordance with conventional procedures, such as an active ingredient in pharmaceutical compositions.

An agent or composition of the present invention can be administered for therapy by any suitable route of administration. It will also be appreciated that the preferred route will vary with the condition and age of the recipient and the disease being treated.

Necrotizing enterocolitis ("NEC") is a medical condition primarily seen in premature infants where portions of the bowel undergo necrosis (tissue death). It occurs postnatally (i.e., is not seen in stillborn infants) and is the second most common cause of mortality. 7% of all neonatal intensive care unit admissions are NEC related. The mortality rate is 12%.

MODES FOR CARRYING OUT THE DISCLOSURE

Microsphere Compositions

This disclosure provides a composition comprising a microsphere, a biofilm-generating probiotic bacterium and a prebiotic, wherein the prebiotic comprises a nutritional supplementation for the probiotic bacterium. In one aspect, the composition further comprises one or more of: a biofilm, a prebiofilmic, coating on the surface of the microsphere a therapeutic drug or agent, a chemical reductant, a molecule that promotes adsorption, a molecule that supports absorption. The microsphere comprises a solid core, a hollow core, wherein in one aspect, the microsphere encapsulates the prebiotic within the hollow core. The microsphere can be biocompatible and/or semi-permeable. In one aspect, the microsphere comprise a biofilm layer or coating on the external surface of the microsphere.

Microsphere Components

In one aspect, the biocompatible microsphere comprises a material selected from the group of: a biodegradable polymer, a non-degradable polymer, a metal, and wherein the diameter of the microsphere is from about 0.5 microns to about 1000 microns. Additional preferred ranges are described herein and incorporated herein by reference. The microspheres can be porous and/or semi-permeable.

Non-limiting examples of biodegradable polymers are selected from one or more of: dextran; dextranomer; poly (lactic-co-glycolic acid) or PLGA; polycaprolactone or PLC; Chitosan; Gelatin; DNA hydrogen; acetalated dextran; poly(lactide); poly(glycolide); poly(lactide-co-glycolide); poly(lactic acid); poly(glycolic acid); poly(lactic acid-co-glycolic acid); poly(lactide)/poly(ethylene glycol) copolymers; poly(glycolide)/poly(ethylene glycol) copolymer; poly(lactide-co-glycolide)/poly(ethylene glycol) copolymers; poly(lactic acid)/poly(ethylene glycol) copolymer; poly(glycolic acid)/poly(ethylene glycol) copolymer; poly (lactic acid-co-glycolic acid)/poly(ethylene glycol) copolymer; poly(caprolactone); poly(caprolactone)/poly(ethylene glycol) copolymer; poly(orthoester); poly(phosphazene); poly(hydroxybutyrate); poly(hydroxybutyrate); poly(lactide-co-caprolactone); polycarbonate; polyesteramide; polyanhidride; poly(dioxanone); poly(alkylene alkylate); polyethylene glycol/polyorthoester copolymer; polyurethane; poly(amino acid); polyetherester; polyacetal; polycyanoacrylate; poly(oxyethylene)/poly(oxypropylene) copolymer; Sephadex® copolymers and/or a combination thereof.

Non-limiting examples of non-biodegradable polymers are selected from one or more poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof.

Non-limiting examples of polymers comprising the microsphere are selected from one or more of: Sephadex, Sephadex G-25, poly(lactic-co-glycolic acid)("PLGA"), polycaprolactone ("PLC"), chitosan; gelatin, DNA hydrogen; acetalated dextran, poly(lactide), poly(glycolide), poly (lactide-co-glycolide), poly(lactic acid), poly(glycolic acid), poly(lactic acid-co-glycolic acid), poly(lactide)/poly(ethylene glycol) copolymers, poly(glycolide)/poly(ethylene glycol) copolymer, poly(lactide-co-glycolide)/poly(ethylene glycol) copolymers, poly(lactic acid)/poly(ethylene glycol) copolymer, poly(glycolic acid)/poly(ethylene glycol) copolymer, poly(lactic acid-co-glycolic acid)/poly(ethylene glycol) copolymer, poly(caprolactone), poly(caprolactone)/poly(ethylene glycol) copolymer, poly(orthoester), poly (phosphazene), poly(hydroxybutyrate), poly (hydroxybutyrate), poly(lactide-co-caprolactone); polycarbonate; polyesteramide; polyanhidride, poly(dioxanone), poly(alkylene alkylate), polyethylene glycol/polyorthoester copolymer, polyurethane, poly(amino acid), polyetherester; polyacetal, polycyanoacrylate, poly(oxyethylene)/poly(oxypropylene) copolymer; and a combination thereof.

Non-limiting examples of metals include cobalt, chromium, gold, nickel, platinum, stainless steel, titanium, tantalum, nickel-titanium, an alloy, and combinations thereof.

Prebiotic

Non-limiting examples of the prebiotic of the composition comprise one or more of: a water-soluble carbohydrate, inulin, oligosaccharides, oligofructose, fructo-oligosaccharide, galacto-oligosaccharide, glucose, starch, maltose, maltodextrins, polydextrose, amylose, sucrose, fructose, lactose, isomaltulose, polyols, glycerol, carbonate, thiamine, choline, histidine, trehalos, nitrogen, sodium nitrate, ammonium nitrate, phosphorus, phosphate salts, hydroxyapatite, potassium, potash, sulfur, homopolysaccharide, heteropolysaccharide, cellulose, chitin, vitamins, and combination thereof.

In another aspect, the prebiotic is selected from one or more of trehalose; nitrogen such as in sodium nitrate, ammonium nitrate, phosphorus such in phosphate salts like hydroxyapatite, potassium such as in potash, sulfur, oligosaccharide, homopolysaccharide, heteropolysaccharide, cellulose, chitin; glucose, fructose, sucrose, maltose, starch, polydextrose, amylose, glycerol, carbonate, and combinations thereof.

In a yet further aspect, the prebiotic of the composition comprises one or more of vitamin mixtures to stimulate microbial growth, nitrogen such as in sodium nitrate, ammonium nitrate, phosphorus such in phosphate salts like hydroxyapatite, potassium such as in potash, sulfur, oligosaccharide, homopolysaccharide, heteropolysaccharide cellulose, chitin; glucose, fructose, sucrose, maltose, starch, polydextrose, amylose, glycerol, carbonate, and combinations thereof.

Probiotic Bacterium

In one aspect, the probiotic bacterium is selected to provide one or more of supporting anti-bacterial immunity, enhancing or supporting a healthy state in the subject, t enhancing or supporting the gastrointestinal barrier, or antagonizing disease-related bacterial infections. In another aspect, the probiotic bacterium is selected to prevent pathogen colonization and/or limit and/or clear the pathogen, and /or limit excessive inflammatory responses by down-regulating cytokine and chemokine production.

Non-limiting examples of the probiotic bacterium is one or more of *L. acidophilus, L. crispatus, L. gasseri, group L. delbrueckii, L. salivarius, L. casei, L. paracasei, L. plantarum, L. rhamnosus, L. reuteri, L. brevis, L. buchneri, L. fermentum, L. rhamnosus, B. adolescentis, B. angulation, B. bifidum, B. breve, B. catenulatum, B. infantis, B. lactis, B. longum, B. pseudocatenulatum, S. thermophiles, Pseudomonas fluorescens, P. protegens, P. brassicacearum, P. aeruginosa; Azospirillum. brabrasilense, A. lipferum, A. halopraeferens, A. irakense; Acetobacter diazotrophicus; Herbaspirillum seropedicae; Bacillus subtilis, Pseudomonas stutzeri, fluorescens, P. putida, P. cepacian, P. vesicularis, P. paucimobilis; Bacillus cereus, B. thuringiensis, B. sphaericus; Shewanella oneidensis; Geobacter bemidjiensis, G. metallireducens, G. sulfurreducens, G. uraniireducens, G. lovleyi; Serratia marcescens, Desulfovibrio vulgaris, D. desulfuricans, Dechloromonas aromatic, Deinococcus radiodurans, Methylibium petroleiphilum, Alcanivorax borkumensis, Archaeglobus fulgidus, Haloferax sp., Halobacterium sp.*, and combinations thereof.

In another aspect, the probiotic is *L. reuteri* that produces GTF protein or containing the GTFW gene (ATCC 23272).

Prebiofilmic

In other aspect, the prebiofilmic comprises an agent that supports biofilm formation and durability, non-limiting examples of such include a DNA binding polypeptide or protein and/or a DNABII polypeptide or protein or an equivalent of each thereof, optionally, a polypeptide comprising one or more of the attached sequence listing, or a biologically active fragment or equivalent of each thereof, alone or in combination.

Complimentary Agents

The microspheres and compositions containing the microspheres can further an agent, wherein the agent is selective against a pathogen that may compete with the probiotic organism. The complimentary agents can be in the core, on the surface of the microsphere in in the composition containing the microspheres. Non-limiting examples of such include chemical reductants; molecules and/or surfaces that promote adsorption (in core or on surface of microsphere); molecules and/or surfaces that promote absorption (in core or on surface of microsphere). In one aspect, the chemical reductants and molecules and/or surfaces that promote absorption are coated on the surface of the microsphere.

Biofilm Layer

In one aspect, the microsphere compositions further comprise a biofilm layer on the external surface of the microparticle. The layer can be from about about 0.5 micron to about 1 millimiter in depth, and ranges in between, e.g., about 1 micron to about 500 microns, about 1 micron to about 250 microns, about 1 micron to about 200 microns, about 1 micron to about 100 microns, about 1 micron to about 50 microns, about 1 micron to about 40 microns, about 1 micron to about 30 microns, about 2 micron to about 100 microns, about 2 microns to about 50 microns, about 2 microns to about 40 microns, about 2 microns to about 30 microns, about 3 microns to about 100 microns, about 3 microns to about 50 microns, about 3 microns to about 40 microns, about 3 microns to about 30 microns, about 5 microns to about 100 microns, about 5 microns to about 50 microns, about 5 microns to about 40 microns, and about 5 microns to about 30 microns.

Compositions

This disclosure also provides one or a plurality of microsphere compositions as described herein in combination with a carrier, e.g., a pharmaceutically acceptable carrier or a biocompatible scaffold. Non-limiting examples pharmaceutically acceptable carriers include diluents, excipients or carriers that may be used in the compositions of the disclosure. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Non-limiting examples of biocompatible scaffolds, include a scaffold or matrix for with the ability to support biofilm proliferation upon administration to a subject or an environment to be treated.

In one aspect, the compositions comprise a plurality of microspheres that are the same or different from each other, e.g, the same or different diameters, the same or different microsphere components, the same or different probiotics, the same or different complimentary agents, the same or different prebiofilmic, and hollow and/or solid cores.

The compositions can be formulated into dosage forms of the biofilm-generative probiotic bacterium, e.g., or provide from an effective amount of the microsphere composition for the end use, e.g., from about $1\times10^5$ to $1\times10^{11}$ CFU/ml, or alternatively from about $1\times10^5$ to about $1\times10^{10}$ CFU/ml, or about $1\times10^5$ to about $1\times10^9$ CFU/ml, or about $1\times10^6$ to about $1\times10^{11}$ CFU/ml, or about $1\times10^6$ to about $1\times10^9$ CFU/ml, or about $1\times10^7$ to about $1\times10^{11}$ CFU/ml, or about $1\times10^7$ to about $1\times10^{10}$ CFU/ml, or about $1\times10^7$ to about $1\times10^9$ CFU/ml, or about $1\times10^8$ CFU/ml.

The compositions can be formulated or processed for ease of administration, storage and application, e.g., frozen, lyophilized, suspended (suspension formulation) or powdered; and processed as a suppository, tablet, solution, suspensions, pills, capsules, sustained release formulation.

Applications and Uses

In general, the compositions of this disclosure find use in therapeutic, agricultural and industrial microbial support, biofilm support, and/or or biofilm remediation, and the components of the compositions and the carriers and additional agents are selected for the specified use.

In one aspect, the compositions provide one or more of supporting anti-bacterial immunity, enhancing or supporting the gastrointestinal barrier, or antagonizing disease-related bacterial infections. In another aspect, the compositions prevents pathogen colonization and/or limits excessive inflammatory responses by down-regulating cytokine and chemokine production.

In one aspect, the compositions are useful for the treatment of a mammal such as a human; simians, murines, such as, rats, mice, chinchilla, canine, such as dogs, leporids, such as rabbits, livestock, sport animals and pets. In another aspect, they are useful to treat agricultural crops such as corn, wheat, soybeans, and potatoes; domestic garden plants such as tomatoes, peppers, spinach, and beans. In a yet further aspect, they are useful for the treatment of contaminated water or soil, machinery and manmade structures.

The indications and uses vary with the environment. The compositions can be used in the treatment or prevention of disease, e.g., psychological disorders, such as depression or anxiety, enteric infectious disease, infection-induced colitis, traveler's diarrhea, inflammatory bowel disease (IBD), colitis, diarrheal illness, vaginosis, wound, burns, psoriasis, dermatitis, tooth decay, periodontitis, sinusitis, or any of chronic and/or recurrent disease that is caused by pathogenic bacteria displacing healthy bacteria or nectrotizing enterocolitis (NEC), to support anti-bacterial immunity, enhancing or supporting the gastrointestinal barrier, correcting or supporting dysbiotic gut flora (and even in the absence of diseases), disease or disorders involving intestinal dysmobility, enhancing or supporting the gastrointestinal mobility, or antagonizing disease-related bacterial infection; vaginosis; colitis or traveler's diarrhea, peritonitis, post-operative ileus, irritable bowel syndrome (IBS), intestinal pseudo-obstruction, and/or constipation.

Thus, in one aspect, this disclosure provides method for treating or preventing a disease or disorder suitably treated by a biofilm in a subject in need thereof is provided herein. The method comprises administering to the subject an effective amount of the composition as disclosed herein, having the components selected for the particular therapy. Non-limiting examples of diseases include psychological disorders, such as depression or anxiety, enteric infectious disease, infection-induced colitis, traveler's diarrhea, inflammatory bowel disease (IBD), colitis, diarrheal illness, vaginosis, wound, burns, psoriasis, dermatitis, tooth decay, periodontitis, sinusitis, or any of chronic and/or recurrent disease that is caused by pathogenic bacteria displacing healthy bacteria or nectrotizing enterocolitis (NEC), and to support anti-bacterial immunity, enhancing or supporting the gastrointestinal barrier, correcting or supporting dysbiotic gut flora (and even in the absence of diseases), disease or disorders involving intestinal dysmobility, enhancing or supporting the gastrointestinal mobility, or antagonizing disease-related bacterial infection; vaginosis; colitis or traveler's diarrhea, peritonitis, post-operative ileus, irritable bowel syndrome (IBS), intestinal pseudo-obstruction, and/or constipation. Additionally, the compositions are useful to promote health and/or to maintain gut homeostasis.

This disclosure also provides a method for delivering a probiotic to a subject comprising administering a dose of a composition as disclosed herein to the subject, thereby administering the probiotic.

The dosage and components of the composition will vary with the subject and purpose of the therapy. In one aspect, the composition is administered to provide from about $1\times10^7$ to about $1\times10^9$ CFU/ml of the biofilm-generating probiotic bacterium. The compositions can be formulated into dosage forms, e.g., or provide from an effective amount of the microsphere composition for the end use, e.g., from about $1\times10^5$ to $1\times10^{11}$ CFU/ml, or alternatively from about $1\times10^5$ to about $1\times10^{10}$ CFU/ml, or about $1\times10^5$ to about $1\times10^9$ CFU/ml, or about $1\times10^6$ to about $1\times10^{11}$ CFU/ml, or about $1\times10^6$ to about $1\times10^9$ CFU/ml, or about $1\times10^7$ to about $1\times10^{11}$ CFU/ml, or about $1\times10^7$ to about $1\times10^{10}$ CFU/ml, or about $1\times10^7$ to about $1\times10^9$ CFU/ml, or about $1\times10^8$ CFU/ml.

The compositions can be administered at about 6, 12, 18, 24, 36, 48, and 72 hours, or can be administered in a single dose.

The compositions can be administered orally, vaginally, topically, by inhalation, intravenously, intramuscularly, or by suppository. They can be administered in any suitable formulation.

For the treatment or prevention of plant disease or in agricultural settings, the composition are useful for the treatment of desiccation, nutrient starvation, nutrient depletion, bacterial pathogen infection, invertebrate antagonism, pollution; severe weather, physical stress, hypoxia, soil acidification. Thus, this disclosure also provides methods for treating a plant, by administering to the plant directly or in its environment, a composition as disclosed herein. The dosage and components of the composition will vary with the plant and purpose of the treatment. In one aspect, the composition is administered to provide from about $1\times10^7$ to about $1\times10^9$ CFU/ml of the biofilm-generating probiotic bacterium. The compositions can be formulated into dosage forms, e.g., or provide from an effective amount of the microsphere composition for the end use, e.g., from about $1\times10^5$ to $1\times10^{11}$ CFU/ml, or alternatively from about $1\times10^5$ to about $1\times10^{10}$ CFU/ml, or about $1\times10^5$ to about $1\times10^9$ CFU/ml, or about $1\times10^6$ to about $1\times10^{11}$ CFU/ml, or about $1\times10^6$ to about $1\times10^9$ CFU/ml, or about $1\times10^7$ to about $1\times10^{11}$ CFU/ml, or about $1\times10^7$ to about $1\times10^{10}$ CFU/ml, or about $1\times10^7$ to about $1\times10^9$ CFU/ml, or about $1\times10^8$ CFU/ml.

The compositions can be administered at about 6, 12, 18, 24, 36, 48, and 72 hours, or can be administered in a single dose. In one aspect, the composition is administered by spraying the plant or by irrigating the plant or admixing the composition with water applying to the plant or its environment. It can by sprayed onto the plant or the soil surrounding the plant, applied dry into the soil surface surrounding the plant, adding the compositions to the irrigation or watering system, or mixing the composition with the soil prior to seeding.

Thus, this disclosure also provides methods to deliver a composition and/or treat or prevent a disease or condition, and/or treat an environment (soil, plant, water, or surface) by contacting the surface or delivering an effective amount of the composition as disclosed herein.

They also are useful in industry, e.g., to treat toxic compounds in water, soil, or air, to treat contamination by heavy metals, such as cadmium, lead, chromium, arsenic, mercury, radioactive actinides, such as uranium, plutonium, thorium; polycyclic aromatic hydrocarbons (PAH), petroleum hydrocarbon, such as crude and refined oil, herbicide or pesticide contamination. The compositions can be formulated or processed for ease of administration, storage and application, e.g., frozen, lyophilized, suspended (suspension formulation) or powdered, and processed for use in industrial applications, e.g., for the treatment of contaminated water or soil, machinery, and manmade structures, e.g., bioreactor, biopile, bio-venting, land-farming, filter surface, permeable reactive barrier, in situ administration via wet or dry application to water or soil.

The amount and components of the composition will vary with the purpose of the treatment. In one aspect, the composition is administered to provide from about $1\times10^7$ to about $1\times10^9$ CFU/ml of the biofilm-generating probiotic bacterium. The compositions can be formulated into dosage forms, e.g., or provide from an effective amount of the microsphere composition for the end use, e.g., from about $1\times10^5$ to $1\times10^{11}$ CFU/ml, or alternatively from about $1\times10^5$ to about $1\times10^{10}$ CFU/ml, or about $1\times10^5$ to about $1\times10^9$ CFU/ml, or about $1\times10^6$ to about $1\times10^{11}$ CFU/ml, or about $1\times10^6$ to about $1\times10^9$ CFU/ml, or about $1\times10^7$ to about $1\times10^{11}$ CFU/ml, or about $1\times10^7$ to about $1\times10^{10}$ CFU/ml, or about $1\times10^7$ to about $1\times10^9$ CFU/ml, or about $1\times10^8$ CFU/ml. The compositions can be delivered in multiple doses, e.g., every 6, 12, 18, 24, 36, 48, and 72 hours, or can be administered in a single dose.

They can be used to treat a bioreactor, biopile, bioventing, landfarming, filter surface, permeable reactive barrier, in situ administration via wet or dry application to water or soil. Thus, this disclosure also provides methods to remediate a biofilm by contacting the surface or machine by contacting the surface, or delivering to the environment an effective amount of the composition. One can determine if the method was successful by assaying for the biofilm.

Agricultural Uses

This disclosure also provides compositions for agricultural use. The microspheres comprise a biofilm-generating probiotic bacterium and a prebiotic, wherein the prebiotic comprises a nutritional supplementation for the probiotic bacterium. In one aspect, the composition further comprises one or more of: a prebiofilmic, a therapeutic drug or agent, a chemical reductant, a molecule that promotes adsorption, a molecule that supports absorption, density-driving cargo, such as ethanol, sunflower oil, or olive oil, or an equivalent of each thereof, or pre-frozen components that are low density upon admininistration or use, but after use or thaw of the pre-frozen components, might be transported or moved from the initial site of administraion. The microsphere comprises a solid core, a hollow core, wherein in one aspect, the microsphere encapsulates the prebiotic within the hollow core.

In one aspect, the biocompatible microsphere comprises a material selected from the group of: a biodegradable polymer, a non-degradable polymer, a metal, and wherein the diameter of the microsphere is from about 0.5 microns to about 1000 microns. Additional preferred ranges are described above and incorporated herein by reference.

Non-limiting examples of biodegradable polymers for agriculture use are selected from one or more of: dextran, dextranomer, poly(lactic-co-glycolic acid) or PLGA; polycaprolactone or PLC; chitosan; gelatin; DNA hydrogen; acetalated dextran, poly(lactide), poly(glycolide), poly(lactide-co-glycolide), poly(lactic acid), poly(glycolic acid), poly(lactic acid-co-glycolic acid), poly(lactide)/poly(ethylene glycol) copolymers, poly(glycolide)/poly(ethylene glycol) copolymer, poly(lactide-co-glycolide)/poly(ethylene glycol) copolymers, poly(lactic acid)/poly(ethylene glycol) copolymer, poly(glycolic acid)/poly(ethylene glycol) copolymer, poly(lactic acid-co-glycolic acid)/poly(ethylene glycol) copolymer, poly(caprolactone), poly(caprolactone)/poly(ethylene glycol) copolymer, poly(orthoester), poly (phosphazene), poly(hydroxybutyrate), poly (hydroxybutyrate), poly(lactide-co-caprolactone), polycarbonate, polyesteramide, polyanhidride, poly(dioxanone), poly(alkylene alkylate), polyethylene glycol/polyorthoester copolymer, polyurethane, poly(amino acid), polyetherester, polyacetal, polycyanoacrylate, poly(oxyethylene)/poly(oxypropylene) copolymer, Sephadex® copolymers and/or a combination thereof.

Non-limiting examples of non-biodegradable polymers are selected from one or more of poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof.

Non-limiting examples of metals include one or more of: cobalt, chromium, gold, nickel, platinum, stainless steel, titanium, tantalum, nickel-titanium, an alloy, and combinations thereof.

Non-limiting examples of the prebiotic include one or more of trehalose; nitrogen such as in sodium nitrate, ammonium nitrate, phosphorus such in phosphate salts like hydroxyapatite, potassium such as in potash, sulfur, oligosaccharide, homopolysaccharide, heteropolysaccharide, cellulose, chitin, glucose, fructose, sucrose, maltose, starch, polydextrose, amylose, glycerol, carbonate, and combinations thereof.

Non-limiting examples of the probiotic bacterium *L. reuteri, Pseudomonas fluorescens, P. protegens, P. brassicacearum, P. aeruginosa; Azospirillum. brabrasilense, A. lipferum, A. halopraeferens, A. irakense; Acetobacter diazotrophicus; Herbaspirillum seropedicae; Bacillus subtilis*, and combinations thereof.

In other aspect, the prebiofilmic comprises an agent that supports biofilm formation and durability, non-limiting examples of such include a DNA binding polypeptide or protein and/or a DNABII polypeptide or protein or an equivalent of each thereof, optionally, a polypeptide comprising one or more of the attached sequence listing, or a biologically active fragment or equivalent of each thereof, alone or in combination.

The microspheres and compositions containing the microspheres can further an agent, wherein the agent is selective against a pathogen that may compete with the probiotic organism. The complimentary agents can be in the core, on the surface of the microsphere or in in the composition containing the microspheres. Non-limiting examples of such include drugs against a pathogen or invertebrate, that are optionally contained in the core of the microsphere.

This disclosure also provides one or a plurality of microsphere compositions as described herein in combination with a carrier, e.g., a pharmaceutically acceptable carrier or a biocompatible scaffold. Non-limiting examples pharmaceutically acceptable carriers include diluents, excipients or carriers that may be used in the compositions of the disclosure.

Non-limiting examples of biocompatible scaffolds, include a scaffold or matrix for with the ability to support biofilm proliferation upon administration to a plant, soil or water.

In a further aspect, the microsphere further comprises a biofilm layer that partially or fully surrounds the microsphere.

In one aspect, the compositions comprise a plurality of microspheres that are the same or different from each other, e.g., the same or different diameters, the same or different microsphere components, the same or different probiotics, the same or different complimentary agents, the same or different prebiofilmic, the same or different biofilm layers, and hollow and/or solid cores.

The compositions can be formulated into dosage forms of the biofilm-generative probiotic bacterium, e.g., or provide from an effective amount of the microsphere composition for the end use, e.g., from about $1\times10^5$ to $1\times10^{11}$ CFU/ml, or alternatively from about $1\times10^5$ to about $1\times10^{10}$ CFU/ml, or about $1\times10^5$ to about $1\times10^9$ CFU/ml, or about $1\times10^6$ to about $1\times10^{11}$ CFU/ml, or about $1\times10^6$ to about $1\times10^9$ CFU/ml, or about $1\times10^7$ to about $1\times10^{11}$ CFU/ml, or about $1\times10^7$ to about $1\times10^{10}$ CFU/ml, or about $1\times10^7$ to about $1\times10^9$ CFU/ml, or about $1\times10^8$ CFU/ml.

The compositions can be formulated or processed for ease of delivery, by spray application onto plant surface and/or soil, dry application onto soil surface, addition to watering system, or mixing with soil prior to seeding. They can be used to treat agricultural crops such as corn, wheat, soybeans, and potatoes; domestic garden plants such as tomatoes, peppers, spinach, and beans. In a yet further aspect, they are useful for the treatment of contaminated water or soil, machinery and manmade structures.

The composition are useful for the treatment of desiccation, nutrient starvation, nutrient depletion, bacterial pathogen infection, invertebrate antagonism, pollution, severe weather, physical stress, hypoxia; soil acidification. Thus, this disclosure also provides methods for treating a plant, by administering to the plant directly or in its environment, a composition as disclosed herein. The dosage and components of the composition will vary with the plant and purpose of the treatment. In one aspect, the composition is administered to provide from about $1\times10^7$ to about $1\times10^9$ CFU/ml of the biofilm-generating probiotic bacterium. The compositions can be formulated into dosage forms, e.g., or provide from an effective amount of the microsphere composition for the end use, e.g., from about $1\times10^5$ to $1\times10^{11}$ CFU/ml, or alternatively from about $1\times10^5$ to about $1\times10^{10}$ CFU/ml, or about $1\times10^5$ to about $1\times10^9$ CFU/ml, or about $1\times10^6$ to about $1\times10^{11}$ CFU/ml, or about $1\times10^6$ to about $1\times10^9$ CFU/ml, or about $1\times10^7$ to about $1\times10^{11}$ CFU/ml, or about $1\times10^7$ to about $1\times10^{10}$ CFU/ml, or about $1\times10^7$ to about $1\times10^9$ CFU/ml, or about $1\times10^8$ CFU/ml.

The compositions can be administered at about 6, 12, 18, 24, 36, 48, and 72 hours, or can be administered in a single dose. In one aspect, the composition is administered by spraying the plant or by irrigating the plant or admixing the composition with water applying to the plant or its environment. It can by sprayed onto the plant or the soil surrounding the plant, applied dry into the soil surface surrounding the plant, adding the compositions to the irrigation or watering system, or mixing the composition with the soil prior to seeding.

Thus, this disclosure also provides methods to deliver a composition and/or treat or prevent a disease or condition, and/or treat an environment (soil, plant, water, or surface) by contacting the surface or delivering an effective amount of the composition as disclosed herein.

One can determine if the treatment has been successful by monitoring for a reduction in diseases and by assaying or assaying for the presence of a probiotic culture in the subject.

Industrial Biofilm Remediation

Also provided herein are biocompatible microspheres, that can be porous and/or semi-permeable, for industrial biofilm remediation, wherein the microspheres comprise a material selected from the group of: a biodegradable polymer, a non-degradable polymer, a metal, and wherein the diameter of the microsphere is from about 0.5 microns to about 1000 microns. Additional preferred ranges are described above and incorporated herein by reference.

For this application, non-limiting examples of biodegradable polymers are selected from one or more of: dextan, dextranomer, poly(lactic-co-glycolic acid) or PLGA, polycaprolactone or PLC, chitosan, gelatin, DNA hydrogen, acetalated dextran, poly(lactide), poly(glycolide), poly(lactide-co-glycolide), poly(lactic acid), poly(glycolic acid), poly(lactic acid-co-glycolic acid), poly(lactide)/poly(ethylene glycol) copolymers, poly(glycolide)/poly(ethylene glycol) copolymer, poly(lactide-co-glycolide)/poly(ethylene glycol) copolymers, poly(lactic acid)/poly(ethylene glycol) copolymer, poly(glycolic acid)/poly(ethylene glycol) copolymer, poly(lactic acid-co-glycolic acid)/poly(ethylene glycol) copolymer, poly(caprolactone), poly(caprolactone)/poly(ethylene glycol) copolymer, poly(orthoester), poly(phosphazene), poly(hydroxybutyrate), poly(hydroxybutyrate), poly(lactide-co-caprolactone), polycarbonate, polyesteramide; polyanhidride, poly(dioxanone), poly(alkylene alkylate), polyethylene glycol/polyorthoester copolymer, polyurethane, poly(amino acid), polyetherester, polyacetal, polycyanoacrylate, poly(oxyethylene)/poly(oxypropylene) copolymer, Sephadex® copolymers and/or a combination thereof.

Non-limiting examples of non-biodegradable polymers are selected from one or more of poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof.

Non-limiting examples of metals include cobalt, chromium, gold, nickel, platinum, stainless steel, titanium, tantalum, nickel-titanium, an alloy, and combinations thereof.

Non-limiting examples of the prebiotic of the composition for industrial use, comprise one or more of vitamin mixtures to stimulate microbial growth, nitrogen such as in sodium nitrate, ammonium nitrate, phosphorus such in phosphate salts like hydroxyapatite, potassium such as in potash, sulfur, oligosaccharide, homopolysaccharide, heteropolysaccharide cellulose, chitin; glucose, fructose, sucrose, maltose, starch, polydextrose, amylose, glycerol, carbonate, and combinations thereof.

For industrial use, the probiotic bacterium is selected to provide one or more of supporting biofilm remediation in an industrial process or surface, and non-limiting examples of the probiotic bacterium is one or more of *Pseudomonas stutzeri, fluorescens, P. putida, P. cepacian, P. vesicularis, P. paucimobilis; Bacillus cereus, B. thuringiensis, B. sphaericus; Shewanella oneidensis; Geobacter bemidjiensis, G. metallireducens, G. sulfurreducens, G. uraniireducens, G. lovleyi; Serratia marcescens, Desulfovibrio vulgaris, D. desulfuricans, Dechloromonas aromatic, Deinococcus radiodurans, Methylibium petroleiphilum, Alcanivorax borkumensis, Archaeglobus fulgidus, Haloferax sp., Halobacterium sp.*, and combinations thereof.

The prebiofilmic of the composition can optionally comprise an agent that supports biofilm formation and durability, non-limiting examples of such include a DNA binding polypeptide or protein and/or a DNABII polypeptide or protein or an equivalent of each thereof, optionally, a polypeptide comprising one or more of the attached sequence listing, or a biologically active fragment or equivalent of each thereof, alone or in combination.

The microspheres and compositions containing the microspheres can further an agent, wherein the agent is selective against a pathogen that may compete with the probiotic organism. The complimentary agents can be in the core, on the surface of the microsphere, or in the composition containing the microspheres. Non-limiting examples of such include chemical reductants, molecules and/or surfaces that promote adsorption (in core or on surface of microsphere), molecules and/or surfaces that promote absorption (in core or on surface of microsphere). In one aspect, the chemical reductants and molecules and/or surfaces that promote absorption are coated on the surface of the microsphere.

In one aspect, the microparticle composition might be modified to be density-driven, in that the density or buoyancy of the cargo allows the microparticle to float during initial application, e.g., oil spills. So the cargo would be selected to be low density and as the cargo is utilized, but after the oil slick is degraded, the microspheres sink to the bottom of the water. Alchohols such as ethanol-sunflower oil, or olive oil, or an equivalent of each thereof and the like or by providing the cargo in a pre-frozen state.

This disclosure also provides one or a plurality of microsphere compositions as described herein in combination with a carrier, e.g., a pharmaceutically acceptable carrier, or a biocompatible scaffold. Non-limiting examples of pharmaceutically acceptable carriers include diluents, excipients or carriers that may be used in the compositions of the disclosure. Non-limiting examples of biocompatible scaffolds, include a scaffold or matrix for with the ability to support biofilm proliferation upon administration to an environment to be treated.

In a further aspect, the microsphere further comprises a biofilm layer that partially or fully surrounds the microsphere.

In one aspect, the compositions comprise a plurality of microspheres that are the same or different from each other, e.g., the same or different diameters, the same or different microsphere components, the same or different probiotics, the same or different complimentary agents, the same or different biofilm layers, the same or different prebiofilmic, and hollow and/or solid cores.

The compositions can be formulated into dosage forms of the biofilm-generative probiotic bacterium, e.g., or provide from an effective amount of the microsphere composition for the end use, e.g., from about $1\times10^5$ to $1\times10^{11}$ CFU/ml, or alternatively from about $1\times10^5$ to about $1\times10^{10}$ CFU/ml, or about $1\times10^5$ to about $1\times10^9$ CFU/ml, or about $1\times10^6$ to about $1\times10^{11}$ CFU/ml, or about $1\times10^6$ to about $1\times10^9$ CFU/ml, or about $1\times10^7$ to about $1\times10^{11}$ CFU/ml, or about $1\times10^7$ to about $1\times10^{10}$ CFU/ml, or about $1\times10^7$ to about $1\times10^9$ CFU/ml, or about $1\times10^8$ CFU/ml.

They also are useful in industry, e.g., to treat toxic compounds in water, soil, or air, to treat contamination by heavy metals, such as cadmium, lead, chromium, arsenic, mercury, radioactive actinides, such as uranium, plutonium, thorium; polycyclic aromatic hydrocarbons (PAH), petroleum hydrocarbon, such as crude and refined oil, herbicide or pesticide contamination.

The compositions can be formulated or processed for ease of administration, storage and application, e.g., frozen, lyophilized, suspended (suspension formulation) or powdered; and processed for use in industrial applications, e.g., for the treatment of contaminated water or soil, machinery, and manmade structures, e.g., bioreactor, biopile, bio-venting, land-farming, filter surface, permeable reactive barrier, in situ administration via wet or dry application to water or soil.

One of skill in the art can determine if the method was successful by assaying for the presence of a biofilm.

Medicinal, Nutritional or Therapeutic Uses

This disclosure provides a composition for nutritional or medicinal use, wherein the composition comprises a microsphere, a biofilm-generating probiotic bacterium and a prebiotic, wherein the prebiotic comprises a nutritional supplementation for the probiotic bacterium. In one aspect, the composition further comprises one or more of: a prebiofilmic, a biofilm layer, a therapeutic drug or agent. The microsphere comprises a solid core, a hollow core, wherein in one aspect, the microsphere encapsulates the prebiotic within the hollow core.

In one aspect, the microsphere comprises a material selected from the group of: a biodegradable polymer, a non-degradable polymer, or a metal, and wherein the diameter of the microsphere is from about 0.5 microns to about 1000 microns, or alternatively rom about 0.5 microns to about 100 microns, or alternatively less than 100 microns.

Non-limiting examples of biodegradable polymers for medicinal use are selected from one or more of dextran, dextranomer, poly(lactic-co-glycolic acid) or PLGA, polycaprolactone or PLC, chitosan, gelatin, DNA hydrogen, acetalated dextran, poly(lactide), poly(glycolide), poly(lactide-co-glycolide), poly(lactic acid), poly(glycolic acid), poly(lactic acid-co-glycolic acid), poly(lactide)/poly(ethylene glycol) copolymers, poly(glycolide)/poly(ethylene glycol) copolymer, poly(lactide-co-glycolide)/poly(ethylene glycol) copolymers, poly(lactic acid)/poly(ethylene glycol) copolymer, poly(glycolic acid)/poly(ethylene glycol) copolymer, poly(lactic acid-co-glycolic acid)/poly(ethylene glycol) copolymer, poly(caprolactone), poly(caprolactone)/poly(ethylene glycol) copolymer, poly(orthoester), poly(phosphazene), poly(hydroxybutyrate), poly(hydroxybutyrate), poly(lactide-co-caprolactone), polycarbonate, polyesteramide; polyanhidride, poly(dioxanone), poly(alkylene alkylate), polyethylene glycol/polyorthoester copolymer, polyurethane, poly(amino acid), polyetherester, polyacetal, polycyanoacrylate, poly(oxyethylene)/poly(oxypropylene) copolymer, Sephadex® copolymers and/or a combination thereof.

Non-limiting examples of non-biodegradable polymers for medicinal use are selected from one or more of poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof.

Non-limiting examples of metals include cobalt, chromium, gold, nickel, platinum, stainless steel, titanium, tantalum, nickel-titanium, an alloy, and combinations thereof.

Non-limiting examples of the prebiotic of the composition for medicinal use comprises one or more of a water-soluble carbohydrate, inulin, oligofructose, fructo-oligosaccharide, galacto-oligosaccharide, glucose, maltose, maltodextrins, polydextrose, sucrose, fructose, lactose, isomaltulose, polyols, glycerol, thiamine, choline, histidine, and combination thereof.

Non-limiting examples of the probiotic bacterium is one or more of *L. acidophilus, L. crispatus, L. gasseri, group L. delbrueckii, L. sahvarius, L. casei, L. paracasei, L. plantarum, L. rhamnosus, L. reuteri, L. brevis, L. buchneri, L. fermentum, L. rhamnosus, B. adolescentis, B. angulation, B. bifidum, B. breve, B. catenulatum, B. infantis, B. lactis, B. longum, B. pseudocatenulatum, S. thermophiles*, and combinations thereof.

Non-limiting examples of the prebiofilmic comprises an agent that supports biofilm formation and durability, non-limiting examples of such include a DNA binding polypeptide or protein and/or a DNABII polypeptide or protein or an equivalent of each thereof, optionally, a polypeptide comprising one or more of the attached sequence listing, or a biologically active fragment or equivalent of each thereof, alone or in combination.

The microspheres and compositions containing the microspheres can further an agent, wherein the agent is selective against a pathogen that may compete with the probiotic organism. The complimentary agents can be in the core, on the surface of the microsphere in in the composition containing the microspheres.

In a further aspect, the microsphere further comprises a biofilm layer that partially or fully surrounds the microsphere.

This compositions for medicinal use can be provide as a composition, comprising one or a plurality of microsphere compositions as described herein in combination with a carrier, e.g., a pharmaceutically acceptable carrier or a biocompatible scaffold.

In one aspect, the compositions comprise a plurality of microspheres that are the same or different from each other, e.g., the same or different diameters, the same or different microsphere components, the same or different biofilm layer, the same or different probiotics, the same or different complimentary agents, the same or different prebiofilmic, and hollow and/or solid cores.

The compositions can be formulated into dosage forms of the biofilm-generative probiotic bacterium, e.g., or provide from an effective amount of the microsphere composition for the end use, e.g., from about $1\times10^5$ to $1\times10^{11}$ CFU/ml, or alternatively from about $1\times10^5$ to about $1\times10^{10}$ CFU/ml, or about $1\times10^5$ to about $1\times10^9$ CFU/ml, or about $1\times10^6$ to about $1\times10^{11}$ CFU/ml, or about $1\times10^6$ to about $1\times10^9$ CFU/ml, or about $1\times10^7$ to about $1\times10^{11}$ CFU/ml, or about $1\times10^7$ to about $1\times10^{10}$ CFU/ml, or about $1\times10^7$ to about $1\times10^9$ CFU/ml, or about $1\times10^8$ CFU/ml.

The compositions can be formulated or processed for ease of administration, storage and application, e.g., frozen, lyophilized, suspended (suspension formulation) or powdered; and processed as a suppository, tablet, solution, suspensions, pills, capsules, sustained release formulation.

The compositions are useful for the treatment of a mammal such as a human, simians, murines, such as, rats, mice, chinchilla, canine, such as dogs, leporids, such as rabbits, livestock, sport animals and pets.

The compositions can be used in the treatment or prevention of disease, e.g., psychological disorders, such as depression or anxiety, enteric infectious disease, infection-induced colitis, traveler's diarrhea, inflammatory bowel disease (IBD), colitis, diarrheal illness, vaginosis, wound, burns, psoriasis, dermatitis, tooth decay, periodontitis, sinusitis, or any of chronic and/or recurrent disease that is caused by pathogenic bacteria displacing healthy bacteria or nectrotizing enterocolitis (NEC), to support anti-bacterial immunity, enhancing or supporting the gastrointestinal barrier, correcting or supporting dysbiotic gut flora (and even in the absence of diseases), disease or disorders involving intestinal dysmobility, enhancing or supporting the gastrointestinal mobility, or antagonizing disease-related bacterial infection; vaginosis; colitis or traveler's diarrhea, peritonitis, post-operative ileus, irritable bowel syndrome (IBS), intestinal pseudo-obstruction, and/or constipation.

Thus, in one aspect, this disclosure provides method for treating or preventing a disease suitably treated by a healthy bacteria and/or a biofilm in a subject in need thereof. The method comprises administering to the subject an effective amount of the composition as disclosed herein, having the components selected for the particular therapy. Non-limiting examples of diseases include those identified above (and incorporated herein by reference) and include one or more of psychological disorders, such as depression or anxiety, enteric infectious disease, infection-induced colitis, traveler's diarrhea, inflammatory bowel disease (IBD), colitis, diarrheal illness, vaginosis, wound, burns, psoriasis, dermatitis, tooth decay, periodontitis, sinusitis, or any of chronic and/or recurrent disease that is caused by pathogenic bacteria displacing healthy bacteria or nectrotizing enterocolitis (NEC), to support anti-bacterial immunity, enhancing or supporting the gastrointestinal barrier, or antagonizing disease-related bacterial infection; vaginosis; colitis or traveler's diarrhea, peritonitis, post-operative ileus, irritable bowel syndrome, intestinal pseudo-obstruction, constipation.

Thus, this disclosure provides methods for delivering a probiotic formulation to a subject in need thereof, e.g., a subject suffering from a disease or condition disclosed herein, by administering to the subject an effective amount of an appropriate or disease-relevant or health-promoting composition as disclosed herein. The compositions are administered by any suitable method of administration, e.g., orally, vaginally, by inhalation, by injection, topically or by suppository.

One can determine if the treatment has been successful by monitoring for a reduction in disease symptoms and by assaying or assaying for the presence of a probiotic culture in the subject.

Nutritional Supplements

The disclosed compositions also are useful as nutritional supplements to promote general health and well-being and maintain gut health and/or homeostasis. Thus, in one aspect, this disclosure also provides a method for promoting health and/or maintaining gut homeostasis in a subject in need thereof, the method comprising, or alternatively consisting essentially of, or yet further consisting of, administering to the subject an effective amount of a composition as described herein, and optionally wherein the suface of the microsphere is porous and/or semi-permeable and the prebiotic is released by diffusion or the microsphere slowly degrades causing leaks and diffusion from the microsphere. One of skill in the art can determine if better general health has been achieved, as well as gut homeostatis, by determining if gut discomfort has been reduced or alleviated.

Diarrheal Illness and GI-Related Disorders

Diarrheal illness occurs in approximately four billion individuals per year and causes more than two million deaths worldwide. Among the most important bacterial causes of diarrheal illness in infants and young children are the attaching and effacing (A/E) pathogens, which upon colonization induce diarrheal disease that is associated with an increase in inflammatory cytokines and structural changes to colonic tissue. This acute infection can have a lasting effect on gut health, and infection with A/E pathogens and excessive inflammatory responses are known risk factors for the development of post-infectious irritable bowel syndrome.

Probiotics are a natural way to protect and restore gut microbiota to a healthy state and have been shown to promote health distal to the site of colonization. See Mackos et al. (2013) Infection and Immunity 81, No. 9 (3253-3263). Unfortunately, even under optimal conditions, probiotic bacteria fail to establish, or sufficiently persist, minimizing the magnitude and duration of their healthful effects. One of the rate limiting steps is the capacity of introduced bacteria to form a lasting biofilm. When bacteria are already in the form of a biofilm (a surface adhered community) as opposed to planktonic (free-living), they more readily establish and persist. The positive effects of probiotic bacteria can be enhanced by providing them in a biofilm state; this can readily be accomplished by growing the bacteria on the surface of a biocompatible and non-toxic microsphere. Biocompatible microspheres can be biodegradable polymers, non-biodegradable polymers, a metal, or a combination thereof. When this surface is in the form of a microsphere, prebiotic and/or prebiofilmic substances can be added as cargo to facilitate establishment and maintenance of the probiotic bacterial biofilm.

Microspheres have added value in ideally providing diffusible prebiotic (nutritional supplementation specific/exclusive to probiotic bacteria) cargo that can help promote probiotic bacterial establishment and survival while limiting pathogenic bacterial challenge. At least for the probiotic bacterium *Lactobacillus reuteri*, the biofilm state is advantageous in establishing in the murine gut over the same bacteria in planktonic form.

Furthermore, *L. reuteri* introduced into mice as biofilms have a more robust and durable prophylactic effect on the pathogenesis of the enteropathogenic bacterium, *Citrobacter rodentium*, than *L. reuteri* in its planktonic form. Based on these results, three highly integrated examples are developed that yield novel formulations of probiotics that provide greater and more lasting effects against dysbiosis preventing or even treating gut pathogenesis with a far reduced need for patient compliance.

The biofilm-generating probiotic bacterium adheres to the surface of the biocompatible microsphere and generates a biofilm. The biocompatible microsphere has either a solid or hollow core. When the biocompatible microsphere has a hollow core, it can carry a prebiotic and any nutritional supplementation for the probiotic bacterium as a cargo. It one aspect, for a microsphere with a hollow core, the sphere surface can be semi-permeable to allow cargo to diffuse to the bound bacteria at high localized concentrations or it can be impermeable but slowly degrade to allow the contents to be released. The prebiotic can be encapsulated within the hollow core. The microsphere can also carry a drug, or a compound, or an agent, which is selective against the growth or proliferation of a pathogen. In addition to a biocompatible microsphere, biofilm-generating probiotic and prebiotic, a novel probiotic formulation may also contain a prebiofilmic, which a substance that supports biofilm formation and durability, specifically, the prebiofilmic is a DNA binding polypeptide or protein and/or a DNABII polypeptide or protein, a fragment and/or an equivalent of each thereof. Non-limiting examples of such are provided in the attached sequence listing. One or more drug, compound or agent as well as one or more prebiofilmic can be within a single microsphere.

The prebiotic can support the growth of any probiotic bacteria, including biofilm-generating bacteria. The prebiotic is usually one or more of a water-soluble carbohydrate, such as inulin, oligofructose, fructo-oligosaccharide, galacto-oligosaccharide, glucose, maltose, maltodextrins, polydextrose, sucrose, fructose, lactose, isomaltulose, polyols, and glycerol. The combination of various prebiotics can be used to support the growth of probiotics.

Probiotics are any type of micro-organisms that have health benefits. Probiotics are also commonly consumed as part of fermented foods with specially added active live cultures, such as in yogurt, soy yogurt, or as dietary supplements. Probiotics can also be taken as a suppository. Some limiting examples of probiotics are *L. acidophilus, L. crispatus, L. gasseri*, group *L. delbrueckii, L. sahvarius, L. casei, L. paracasei, L. plantarum, L. rhamnosus, L. reuteri, L. brevis, L. buchneri, L. fermentum, L. rhamnosus, B. adolescentis, B. angulation, B. bifidum, B. breve, B. catenulatum, B. infantis, B. lactis, B. longum, B. pseudocatenulatum*, and *S. thermophiles*. In one aspect, the probiotic is an *L. reuteri* that expresses GTF protein. All strains of *L. reuteri* possess at least one GTF protein, although they can vary between strains, e.g., in DSM20016, the GTF is GTFW and uses maltose as its sole substrate while in DSM 17938 the GTF is GTFA, and it uses sucrose as its sole substate.

Probiotics support anti-bacterial immunity by preventing pathogen colonization and/or limiting excessive inflammatory responses. Without being bound by theory, the probiotics down-regulate cytokine and chemokine production.

The biocompatible microsphere can be one or more of a biodegradable polymer, a non-biodegradable polymer, a metal, or a mixture thereof. The biodegradable polymer can be selected from, but not limited to: dextran; dextranomoer; poly(lactic-co-glycolic acid) or PLGA; polycaprolactone or PLC; Chitosan; Gelatin; DNA hydrogen; acetalated dextran; poly(lactide); poly(glycolide); poly(lactide-co-glycolide); poly(lactic acid); poly(glycolic acid); poly(lactic acid-co-glycolic acid); poly(lactide)/poly(ethylene glycol) copolymers; poly(glycolide)/poly(ethylene glycol) copolymer; poly(lactide-co-glycolide)/poly(ethylene glycol) copolymers; poly(lactic acid)/poly(ethylene glycol) copolymer; poly(glycolic acid)/poly(ethylene glycol) copolymer; poly (lactic acid-co-glycolic acid)/poly(ethylene glycol) copolymer; poly(caprolactone); poly(caprolactone)/poly(ethylene glycol) copolymer; poly(orthoester); poly(phosphazene); poly(hydroxybutyrate); poly(hydroxybutyrate); poly(lactide-co-caprolactone); polycarbonate; polyesteramide; polyanhidride; poly(dioxanone); poly(alkylene alkylate); polyethylene glycol/polyorthoester copolymer; polyurethane; poly(amino acid); polyetherester; polyacetal; polycyanoacrylate; poly(oxyethylene)/poly(oxypropylene) copolymer; Sephadex® copolymers (made from dextran cross-linked with epicholorhydine, commercially available from Sigma-Aldrich and noted in Koo and Wankat (1988) Korean Biochem. J. 21(1)) and/or a combination thereof. The non-biodegradable polymer can be selected from, but not limited to, poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof. The metal can be selected from, but not limited to, cobalt, chromium, gold, nickel, platinum, stainless steel, titanium, tantalum, nickel-titanium, and alloys and combinations thereof.

The microspheres are selected to facilitate the endurance and robustness of the probiotic biofilms are identified and characterized. It has been shown that probiotic biofilms formed on the biodegradable (and FDA approved) surface, poly (lactic-co-glycolic acid) (PLGA) yields biofilms that are superior at preventing pathogen translocation through the epithelial barrier. Other FDA approved or generally regarded as safe (GRAS) materials that can be used to create surfaces to grow biofilms are also examined. The results using biological effectiveness and durability in animal models and shelf life as the base criteria are prioritized. Finally, to further improve the effectiveness of the introduction and maintenance of the probiotic biofilm, prebiotic substances to the probiotic biofilm surface by way of diffusible cargo within the microspheres are provided.

In a further aspect, the microspheres are partially or fully coated by a biofilm layer. The layer can be from about about 0.5 micron to about 1 millimiter in depth, and ranges in between, e.g., about 1 micron to about 500 microns, about 1 micron to about 250 microns, about 1 micron to about 200 microns, about 1 micron to about 100 microns, about 1 micron to about 50 microns, about 1 micron to about 40 microns, about 1 micron to about 30 microns, about 2 micron to about 100 microns, about 2 microns to about 50 microns, about 2 microns to about 40 microns, about 2 microns to about 30 microns, about 3 microns to about 100 microns, about 3 microns to about 50 microns, about 3 microns to about 40 microns, about 3 microns to about 30 microns, about 5 microns to about 100 microns, about 5 microns to about 50 microns, about 5 microns to about 40 microns, and about 5 microns to about 30 microns.

Composition for Treatment of Diarrheal and Other GI-Related Disorders

This disclosure provides a composition comprising, or alternatively consisting essentially of, or yet further consisting of, a biocompatible microsphere, a biofilm-generating probiotic bacterium and a prebiotic, wherein the prebiotic comprises, or alternatively consists essentially of, or yet further consists of a nutritional food source or supplement for the culturing and/or growth of the probiotic bacterium. The composition can further comprise a prebiofilmic. The prebiofilmic comprises a substance that supports biofilm formation and durability, specifically; the prebiofilmic can be a DNA binding polypeptide or protein and/or a DNABII polypeptide or protein. In one aspect, the composition is frozen, for example flash frozen. In another aspect, the composition is lyophilized or dried in powder form. In a further aspect, it is formulated for administration as a suppository or in ingestible form (e.g., tablet). The composition can further comprise a mixture of the above-noted microspheres, e.g., a mixture containing two or more probiotic bacterium and/or two or prebiofilmics and/or two or more nutritional and/or supplement to support the culturing and/or growth of the probiotic bacterium.

In some embodiments, the prebiotic comprises a water-soluble carbohydrate selected from, but not limited to, one or more of inulin, oligofructose, fructo-oligosaccharide, galacto-oligosaccharide, glucose, maltose, maltodextrins, polydextrose, sucrose, fructose, lactose, isomaltulose, polyols, glycerol, and combinations thereof. In one aspect, the composition further comprises a solid or a liquid carrier, such as a pharmaceutically acceptable carrier.

As is apparent to those of skill in the art, the prebiotic and prebiofilmic are selected in each composition to specifically support the growth of the probiotic bacterium. By way of example only, when the probiotic bacterium comprises *L. reuteri*, the composition comprises an effective amount of sucrose, glycerol and optionally HU polypeptide or protein, to support the growth and maintenance of the probiotic when administered to the subject or patient. Non-limiting examples of prebioflimic compositions include, without limitation, one or more of the polypeptides provided in the attached sequence listing, a c-terminal fragment thereof, or a n-terminal fragment thereof, or the additional strains and polypeptides and fragments thereof, such as the full length or the c-terminal fragment or the n-terminal fragment of those provided in Table 4, and equivalents of each thereof. Additional nutritional supplements for the support of other probiotic bacterium are disclosed in Bergey's Manual of Determinative Bacteriology, $9^{th}$ Ed, Ed. Holt et al., WilliamsWilkins (1994), Non-limiting examples of a probiotic bacterium for use in the composition includes, without limitation, one or more of *L. acidophilus, L. crispatus, L. gasseri,* group *L. delbrueckii, L. salivarius, L. casei, L. paracasei, L. plantarum, L. rhamnosus, L. reuteri, L. brevis, L. buchneri, L. fermentum, L. rhamnosus, B. adolescentis, B. angulation, B. bifidum, B. breve, B. catenulatum, B. infantis, B. lactis, B. longum, B. pseudocatenulatum, S. thermophiles,* or a combination thereof. As is apparent to those of skill in the art, one or more bacterium can be combined in a single composition. In some embodiments, the probiotic bacterium is *Lactobacillus reuteri* that in a further aspect, expresses GTF protein. In other aspect it express GTFA protein. The bacteria are available from commercial sources, such as the American Type Culture Collection (ATCC). In one aspect, the one or more probiotic bacterium in the composition supports anti-bacterial immunity. In other aspects, the one or more probiotic bacterium in the composition prevents pathogen colonization and/or limits excessive inflammatory responses by down-regulating cytokine and chemokine production. In some embodiments, the composition further comprises an agent, and the agent is selective against a pathogen, such as a competing pathogen.

The biocompatible microsphere comprises one or more of a biodegradable polymer, a non-biodegradable polymer, a metal, or a combination thereof. In some embodiments, the microsphere comprises a solid core. In some embodiments, the microsphere comprises a hollow core. In some embodiments, the prebiotic is encapsulated within the hollow core of the microsphere and can be released at high concentrations to just the adhered probiotic either due to the semipermeable nature of the microsphere surface or via the gradual degradation of the microsphere.

In one aspect, the disclosure provides a composition comprising, or alternatively consisting essentially of, or yet further consisting of, a PGLA-biocompatible microsphere, one or more biofilm-generating probiotic bacterium, and a nutritional supplementation comprising one or more of sucrose or glycerol in an amount to support the growth of the probiotic bacterium. The biofilm-generating probiotic bacterium may comprise *Lactobacillus reuteri* ("*L. reuteri*"), that can optionally express GTF protein. The composition may further comprise, or alternatively consist essentially of, or yet further consist of, an effective amount of IHF or HU polypeptide or protein. The composition can further comprise a pharmaceutically acceptable carrier or a biocompatible scaffold and is optionally formulated as a suppository.

The size of the microsphere can range from about 0.5 microns to about 100 microns. In certain embodiments, the microsphere is less than about 100 microns in diameter. In other embodiments, the microsphere is less than about 50 microns, or less than about 40 microns, or less than about 30 microns, less than about 20 microns, less than about 10 microns, or less than about 5 microns, or less than 3 microns to 0.5 microns in diameter. In further embodiments, the microsphere is from about 0.5 microns to about 90 microns, or to about 80 microns, or to about 70 microns, or to about 60 microns, or to about 50 microns, or to about 40 microns, or to about 30 microns, or to about 20 microns, or about 10 microns, or about 5 microns, or about 3 microns, or about 2 microns, or about 1 micron, in diameter. Alternatively, the diameter is from about 1 to about 100, or alternatively from about 1 to about 75, or alternatively from about 1 to about 50, or alternatively from about 1 to about 25, or alternatively from about 1 to about 15, or alternatively from about 1 to about 10, microns in diameter.

In some embodiments, the microsphere is a biodegradable polymer, non-limiting examples of such include: dextran, dextranomer; poly(lactic-co-glycolic acid)("PLGA"); poly-caprolactone ("PLC"); chitosan; gelatin; DNA hydrogen; acetalated dextran; poly(lactide); poly(glycolide); poly(lactide-co-glycolide); poly(lactic acid); poly(glycolic acid); poly(lactic acid-co-glycolic acid); poly(lactide)/poly(ethylene glycol) copolymers; poly(glycolide)/poly(ethylene glycol) copolymer; poly(lactide-co-glycolide)/poly(ethylene glycol) copolymers; poly(lactic acid)/poly(ethylene glycol) copolymer; poly(glycolic acid)/poly(ethylene glycol) copolymer; poly(lactic acid-co-glycolic acid)/poly(ethylene glycol) copolymer; poly(caprolactone); poly(caprolactone)/poly(ethylene glycol) copolymer; poly(orthoester); poly (phosphazene); poly(hydroxybutyrate); poly (hydroxybutyrate); poly(lactide-co-caprolactone); polycarbonate; polyesteramide; polyanhidride; poly(dioxanone); poly(alkylene alkylate); polyethylene glycol/polyorthoester copolymer; polyurethane; poly(amino acid); polyetherester; polyacetal; polycyanoacrylate; poly(oxyethylene)/poly(oxypropylene) copolymer; and combinations thereof. In some embodiments, the biodegradable polymer is poly(lactic-co-glycolic acid) or PLGA.

In some embodiments, the microsphere comprises a non-biodegradable polymer. Non-limiting examples of non-biodegradable polymers, include without limitation, of one or more of poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly (vinyl imidazole), chorosulphonated polyolefins, polyethylene oxide, and copolymers and blends thereof.

In some embodiments, the microsphere comprises a metal. The metal can be selected from, but not limited to, one or more of cobalt, chromium, gold, nickel, platinum, stainless steel, titanium, tantalum, nickel-titanium, and alloys and combinations thereof.

Pharmaceutical Compositions

The composition can be formulated as a frozen composition, e.g., flash frozen, dried or lyophilized for storage and/or transport. In addition, the composition can administered alone or in combination with a carrier, such as a pharmaceutically acceptable carrier or a biocompatible scaffold. Compositions of the invention may be conventionally administered rectally as a suppository, parenterally, by injection, for example, intravenously, subcutaneously, or intramuscularly. Additional formulations which are suitable for other modes of administration include oral formulations. Oral formulations include such normally employed excipients such as, for example, pharmaceutical grades of mannitol, lactose, starch, magnesium stearate, sodium saccharine, cellulose, magnesium carbonate and the like. These compositions take the form of solutions, suppositories, suspensions, tablets, pills, capsules, sustained release formulations or powders and contain about 10% to about 95% of active ingredient, preferably about 25% to about 70%.

Typically, compositions are administered in a manner compatible with the dosage formulation, and in such amount as will be therapeutically effective for the disease or condition by treated. The quantity to be administered depends on the subject to be treated. Precise amounts of the composition to be administered depend on the judgment of the practitioner. Suitable regimes for initial administration and boosters are also variable, but are typified by an initial administration followed by subsequent administrations.

In many instances, it will be desirable to have multiple administrations of the compositions about, at most about or at least about 3, 4, 5, 6, 7, 8, 9, 10 days or more. The administrations will normally range from 2 day to twelve week intervals, more usually from one to two week intervals. Periodic boosters at intervals of 0.5-5 years, usually two years, may be desirable to maintain the condition of the immune system In some embodiments, additional pharmaceutical compositions are administered to a subject to support or augment the compositions as described herein. Different aspects of the present invention involve administering an effective amount of the composition to a subject. Additionally, such compositions can be administered in combination with modifiers of the immune system. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The carrier may be a solvent or dispersion medium containing, for example, water, ethanol, polyol (for example, glycerol, propylene glycol, and liquid poly(ethylene glycol), and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of undesirable microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

An effective amount of therapeutic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

Processes for Preparing Compositions

This disclosure also provides a method for preparing a composition as described herein, comprising, or alternatively consisting essentially of, or yet further consists of, the steps of admixing, contacting or culturing a biocompatible microsphere with a biofilm-generating probiotic bacterium and a prebiotic. In one aspect, the method further comprises adding or admixing a prebiofilmic that supports the formation and growth of a biofilm by the bacterium. Non-limiting examples of such include, one or more of a DNA binding polypeptide or protein and/or a DNABII polypeptide or protein. In a further aspect, the microspheres are contacted with a biofilm or placed into a culture that supports the growth of a biofilm on the surface of the microsphere. Additional components, as disclosed herein, can be further admixed with the microspheres, etc.

Therapeutic Methods for Colonic and GI Health

Diarrheal illness is a major worldwide cause of morbidity and mortality, and accounts for approximately 15% of deaths in children. Enterohemorrhagic *Escherichia coli* (EHEC) and enteropathogenic *E. coli* (EPEC) are two primary bacterial causes of pediatric diarrhea. The mechanisms by which these pathogens cause diarrheal disease is not yet completely understood, but is initiated when the pathogens colonize the intestinal epithelium (Nataro and Kaper (1998) Diarrheagenic *Escherichia Coli*, Clin Microbiol Rev. 11:142-201).

A closely related pathogen, namely *Citrobacter rodentium* is a murine pathogen that is widely used to model human EPEC and EHEC infection, because mice are relatively resistant to both EPEC and EHEC. In mice, *C. rodentium* results in colonic pathology that is nearly indistinguishable from that produced by EPEC and EHEC in humans (Borenshtein, M. et al. (2008) Utility of the *Citrobacter rodentium* Infection Model in Laboratory Mice, Curr Opin Gastroenterol, 24:32-7; Luperchio and Schauer (2001) Molecular Pathogenesis of *Citrobacter rodentium* and Transmissible Murine Colonic Hyperplasia, Microbes Infect, 3:333-40; Mundy, T. T. et al. (2005) *Citrobacter rodentium* of Mice and Man, Cell Microbiol 7:1697-706). This may not be surprising, since *C. rodentium* possesses a homologue of the locus of enterocyte effacement (LEE) pathogenicity island carried by EPEC and EHEC that encodes for the effector proteins necessary for the development of attaching and effacing (A/E) lesions. These lesions are accompanied by the development of colonic hyperplasia, and pathological colitis marked by epithelial defects and leukocyte infiltration (Luperchio and Schauer (2001) Molecular Pathogenesis of *Citrobacter rodentium* and Transmissible Murine Colonic Hyperplasia, Microbes Infect. 3:333-40).

The intestinal epithelium provides a formidable barrier to enteric pathogens. In order to cause disease, enteric pathogens must either adhere to or penetrate/invade host epithelial cells. Thus, interaction with epithelial cells is the first step in pathogenicity for all enteric pathogens, and this step can be studied through the use of A/E pathogens by assessing colonic colonization and resultant pathology.

Colonization of A/E pathogens in the colon is dependent upon the composition of the intestinal microbiota. Inducing dysbiosis (the disruption of the native populations of beneficial bacteria) within the colonic microbiota by administering antibiotics (Wlodarska, B. et al. (2011) Antibiotic Treatment Alters the Colonic Mucus Layer and Predisposes the Host to Exacerbated *Citrobacter rodentium*-Induced Colitis, Infect Immun, 79:1536-45) or by inducing an inflammatory response (Lupp, M. L. et al. (2007) Host-Mediated Inflammation Disrupts the Intestinal Microbiota and Promotes the Overgrowth of *Enterobacteriaceae*, Cell Host Microbe, 2:119-29) has been shown to greatly enhance pathogen colonization.

Colonic dysbiosis can further exacerbate the inflammatory response to the colonic pathogen (Wlodarska, B. et al. (2011) Antibiotic Treatment Alters the Colonic Mucus Layer and Predisposes the Host to Exacerbated *Citrobacter rodentium*-Induced Colitis, Infect Immun. 79:1536-45), but even in the absence of pathogen challenge, dysbiosis can propagate inflammatory responses in genetically susceptible individuals, as evidenced by the findings of dysbiosis in patients with inflammatory bowel disease (Machiels et al. (2013) A Decrease of the Butyrate-Producing Species *Roseburia hominis* and *Faecalibacterium prausnitzii* Defines Dysbiosis in Patients with Ulcerative Colitis, Gut, published online first Sep. 10, 2013; Morgan et al. (2012) Dysfunction of the Intestinal Microbiome in Inflammatory Bowel Disease and Treatment, Genome Biol., 13:R79) or irritable bowel syndrome (Carroll et al. (2012) Alterations in Composition and Diversity of the Intestinal Microbiota in Patients with Diarrhea-Predominant Irritable Bowel Syndrome, Neurogastroenterol Motil. 24:521-30, e248; Chassard, M. et al. (2012) Functional Dysbiosis within the Gut Microbiota of Patients with Constipated-Irritable Bowel Syndrome, Aliment Pharmacol Ther. 35:828-38).

In some embodiments, a method for treating or preventing a disease in a subject is provided, comprising administering to a subject an effective amount of a composition as described above, to a subject in need of such treatment. As used herein, a "subject" intends an animal (e.g., murine, bovine, canine, feline, equine, simian) or a human. Non-limiting diseases to be treated include, but not limited to the diseases and disorders listed above (and incorporated herein by reference), such as psychological disorders, such as depression or anxiety, enteric infectious disease, infection-induced colitis, traveler's diarrhea, inflammatory bowel disease (IBD), colitis, diarrheal illness, vaginosis, wound, burns, psoriasis, dermatitis, tooth decay, periodontitis, sinusitis, or any of chronic and/or recurrent disease that is caused by pathogenic bacteria displacing healthy bacteria or nectrotizing enterocolitis (NEC). In addition, the compositions can be administered to support anti-bacterial immunity, enhancing or supporting the gastrointestinal barrier, or antagonizing disease-related bacterial infection. In some embodiments, the disease is vaginosis. In some embodiments, the disease is colitis or traveler's diarrhea. As is apparent to the skilled artisan, the composition is specifically selected for the disease to be treated. In some embodiments, the composition further comprises a prebiofilmic. In some embodiments, the prebiofilmic comprises a DNA binding polypeptide or protein and/or a DNABII polypeptide or protein, e.g., an IHF or an HU, a fragment thereof and/or an equivalent of each thereof. In some embodiments, the composition is administered as a suppository.

In some embodiments, the composition of the method is administered to provide from about $1\times10^7$ to about $1\times10^9$ CFU/ml of the biofilm-generating probiotic bacterium. In some embodiments, the composition is administered at about 6, 12, 18, 24, 36, 48, and 72 hours. In some embodiments, the composition is administered in a single dose.

In some embodiments, a method of administering a probiotic is provided, comprising administering a dose of a composition as described above, comprising, or alternatively consisting essentially of, or yet consisting of, a biocompatible microsphere, a biofilm-generating probiotic bacterium, a prebiotic, and a prebiofilmic to a subject in need of such treatment. In some embodiments, the composition of the method is administered to provide from about $1\times10^7$ to about $1\times10^9$ CFU/ml of the biofilm-generating probiotic bacterium. In some embodiments, the composition is administered at about 6, 12, 18, 24, 36, 48, and 72 hours. In some embodiments, the composition is administered in a single dose.

Kits

In some embodiments, a kit containing one or more compositions as described herein is provided. The kit comprises, or alternatively consists essentially of, or yet further consists of, a composition as described above, and instructions for use. Alternatively, the kit comprises a microsphere and instructions to make the composition as described above. In one aspect, the bacteria and prebiotic are also provided in the kit.

EXPERIMENTAL EXAMPLES

Example 1

To determine if *L. reuteri* in a biofilm state are superior to planktonic bacteria for establishment in the murine gut, *L. reuteri* was introduced via oral gavage, but instead of repeating the gavage daily, which is typically needed for retention of planktonic bacteria and for beneficial effects 15, 41, a single administration of *L. reuteri* was provided. The *L. reuteri* were grown in biofilm cultures or biofilm grown on poly(lactic-co-glycolic acid) microspheres, such as PLGA, or other FDA approved and biodegradable microspheres (hydrolyzed into lactic acid and glycolic acid) with diameters ranging from 20-300 μm (Beer, et al., (1998) Poly (Lactic-Glycolic) Acid Copolymer Encapsulation of Recombinant Adenovirus Reduces Immunogenicity in Vivo, Gene Ther, 5: 740-6; Kumari, et al., (2010) Biodegradable Polymeric Nanoparticles Based Drug Delivery Systems, Colloids Surf B Biointerfaces, 75:1-18).

Figure 3:
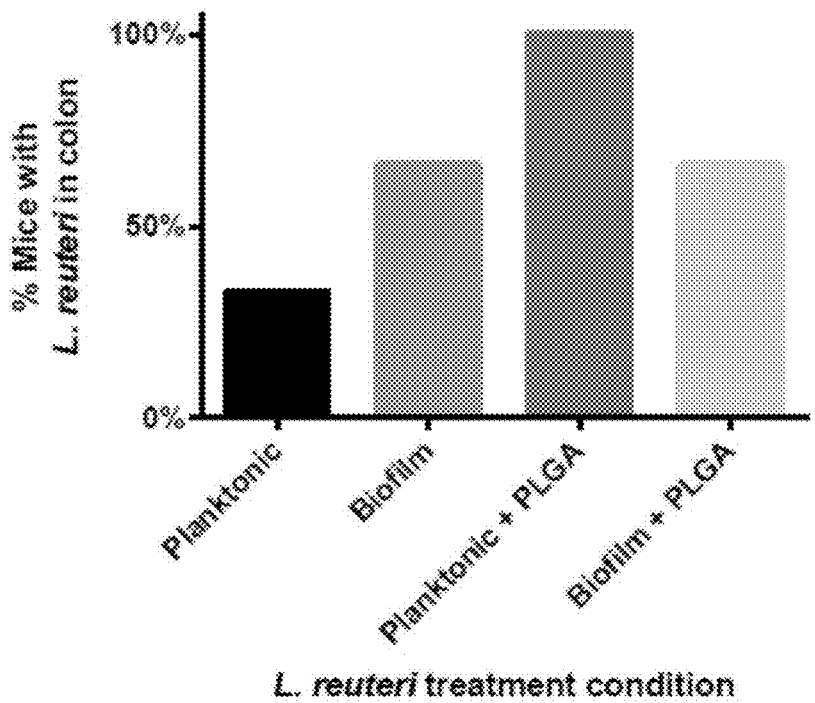
FIG. 3 illustrates that *L. reuteri* in vivo colonization and retention with a single oral administration. Mice (n=3/condition) were administered *L. reuteri* as planktonic, planktonic+PLGA, biofilm, and biofilm+PLGA cultures via oral gavage. After seven days, mice were sacrificed and *L. reuteri* 16S rRNA genes were PCR amplified from the mouse colon. The probiotic was found in a higher percentage of mice that were treated with biofilm cultures or cultures with PLGA present than in planktonic treatments.

Similar preparations of planktonic bacteria were prepared but PLGA microspheres and prebiofilmics were added just prior to gavage. As shown in FIG. 3, the number of mice in which *L. reuteri* was detected in the murine colon after 7 days increased when introduced as a biofilm versus planktonic-grown cells. The presence of PLGA also enhanced the number of mice that were positive for *L. reuteri* compared to conditions where PLGA was not present regardless of whether the bacteria were planktonic or in a biofilm state; this could indicate that *L. reuteri* can initiate attachment to the PLGA, a prelude to biofilm formation, even during this brief interaction (<30 minutes). In the stomach, the only conditions where all mice retained *L. reuteri* was biofilm-grown cells with the addition of PLGA. Thus, it is evident that growing *L. reuteri* in a biofilm in the presence of PLGA enhances colonization and persistence within the stomach and colon compared to planktonic-grown cells.

Example 2: *L. Reuteri* vs *C. Rodentium* In Vitro

To determine if *L. reuteri* has the capacity to better compete with *C. rodentium* as either a biofilm or in planktonic state in vitro, a competition assay was developed. Here *C. rodentium* biofilms in glass chamber slides (LB medium, 24 hours, 37° C., 5% $CO_2$) were performed. *L. reuteri* (108 colony forming units (CFUs)) was then added as a treatment either as planktonic or in one of three biofilm forms (biofilm, PLGA biofilm, PLGA+HU biofilm; preparation as in FIG. 3)

in a medium compatible with both organisms. After 16 hours, the biofilm contents of the chamber slides was removed and aliquots were plated on media selective for *L. reuteri* (MRS) and *C. rodentium* (LB). *C. rodentium* treated with *L. reuteri* biofilm showed a >2 fold decrease in CFU/ml compared to untreated (Table 1), regardless of the state of the introduced *L. reuteri*. More interesting, while all the *L. reuteri* proliferated during the 16 hour challenge, the *L. reuteri* introduced in the form of a biofilm yielded >10-fold more CFUs than when added in planktonic form.

TABLE 1

*L. reuteri* vs. *C. rodentium* in vitro competition assays

| Condition[a] | *C. rodentium* Biofilm (CFU/ml) | *L. reuteri* Biofilm (CFU/ml) |
|---|---|---|
| *C. rodentium* biofilm | | |
| Untreated | $1.71 \times 10^9$ | n/a |
| +L.r planktonic | $6.00 \times 10^8$ | $9.00 \times 10^7$ |
| +L.r biofilm | $4.65 \times 10^8$ | $1.12 \times 10^9$ |
| +L.r PLGA biofilm | $5.30 \times 10^8$ | $1.17 \times 10^9$ |
| +L.r PLGA HU biofilm | $4.30 \times 10^8$ | $1.08 \times 10^9$ |
| *L. reuteri* biofilm | | |
| Untreated | n/a | $2.00 \times 10^9$ |
| +C.r planktonic | $9.20 \times 10^6$ | $1.40 \times 10^9$ |
| +C.r biofilm | $7.90 \times 10^7$ | $2.60 \times 10^9$ |
| PLGA + C.r biofilm | $5.00 \times 10^7$ | $2.50 \times 10^9$ |
| PLGA HU + C.r biofilm | $7.25 \times 10^7$ | $3.45 \times 10^9$ |

[a]Biofilms were treated with $10^8$ CFU of challenge condition

In the converse experiment, the *L. reuteri* biofilm was introduced first and then treated with *C. rodentium* ($10^8$ CFUs) in planktonic and biofilm forms. In contrast to the previous experiment, *L. reuteri* was still able to proliferate increasing in CFUs by >10-fold regardless of the presence of *C. rodentium* (<2-fold difference between conditions) but *C. rodentium* did not proliferate during the 16 hour challenge and was actually reduced in CFUs when introduced planktonically. These in vitro results show that *C. rodentium* biofilms can be effectively challenged with *L. reuteri* and when introduced in the biofilm state, *L. reuteri* persist better than planktonic cells. Moreover, preformed *L. reuteri* biofilms create a poor environment for challenge by planktonic *C. rodentium* to establish.

Example 3: *L. Reuteri* vs *C. Rodentium* In Vivo

Figure 4:
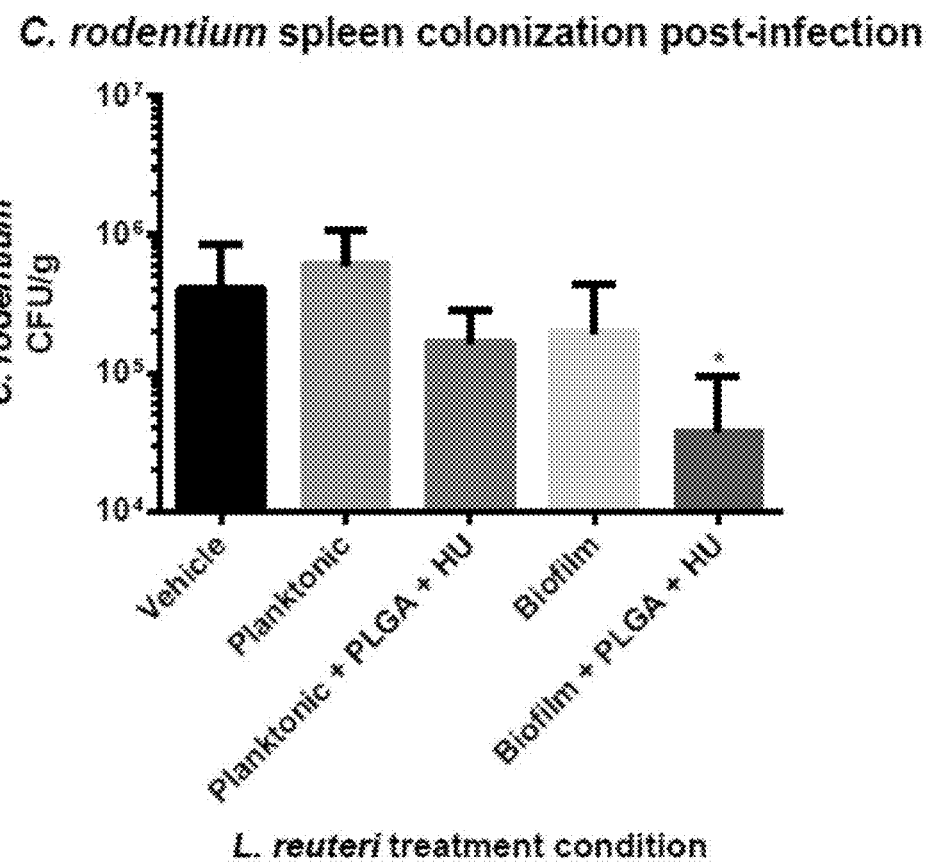
FIG. 4 illustrates that *L. reuteri* biofilm grown with PLGA microspheres and HU reduces *C. rodentium* spleen colonization more effectively than biofilm and planktonic *L. reuteri*. Mice (n=6/condition) were treated with a single oral gavage of *L. reuteri* in one of the following forms: planktonic, planktonic+PLGA+HU, biofilm, and biofilm+PLGA+HU (0.115 µg/ml PLGA, 10 µg/ml HU). After 12 hours the mice were gavaged with *C. rodentium*, and sacrificed 12 days post-infection for necropsy. Only *L. reuteri* biofilm+PLGA+HU showed a statistically significant decrease in *C. rodentium* CFU/g(P=0.0343).

To determine if *L. reuteri* has the capacity to better compete with *C. rodentium* as either a biofilm or in planktonic state in vivo, a version of the published competition assay was utilized Mackos, et al., (2013) Probiotic *Lactobacillus reuteri* Attenuates the Stressor-Enhanced Severity of Citrobacter Rodentium Infection, Infect Immun, 81:3253-63). Briefly, *L. reuteri* were introduced by oral gavage to mice as described above (*L. reuteri* planktonic vs biofilm in vivo). After 12 hours, an equal number of planktonic *C. rodentium* were also added by gavage. After 12 days, all mice were sacrificed for necropsy. Unlike the published work that shows that *C. rodentium* penetration of brush border epithelia and propagation to the spleen can be thwarted by daily doses of planktonic *L. reuteri* (Mackos, et al., (2013) Probiotic *Lactobacillus reuteri* Attenuates the Stressor-Enhanced Severity of *Citrobacter rodentium* Infection, Infect Immun, 81:3253-63), there was a statistically significant 10-fold drop in *C. rodentium* penetration to the spleen in the prebiofilmic treated *L. reuteri* biofilm with a single dose (FIG. 4). This result is consistent with the magnitude and robustness of prebiofilmic treated probiotic biofilms of having a more durable phenotype in vivo.

Example 4: Characterization of Probiotic Therapeutic Biofilms for Endurance and Robustness This example has provided strong evidence that the probiotics in the biofilm state provides a superior formulation to bacteria grown planktonically. It also provides one example of how to prepare these biofilms including the frequency of dosing. In addition, the example examines the nature of the biofilm itself to begin to determine why this state out performs planktonic bacteria. Finally, it examines the shelf life of the preparations as a prelude to reduction to practice in human hosts. Combined, this example identifies and characterizes the conditions and constituents for probiotic biofilm preparations.

Example 4.1: Effects of Growth Phase

*L. reuteri* forms a robust biofilm in vitro and that *L. reuteri* in a 24-hour biofilm establishes well in the mouse gut were shown. This Example varies the age of the biofilm to determine the optimal age for biofilm establishment.

In vivo *L. reuteri* biofilms. *L. reuteri* begins to attach almost immediately when exposed to a surface. After 6 hours sufficient biomass has been produced to be both visible and to start forming the classic biofilm structures (e.g., mushroom, Abee and Kuipers, (2011) Understanding Microbial Behavior within and Outside the Host to Improve Food Functionality and Safety, Curr Opin Biotechnol, 22:133-5). *L. reuteri* biofilms are isolated at about 6, 12, 18, 24, 36, 48 and 72 hours, that have been grown on PGLA microspheres with HU and calf thymus DNA (as described above) normalizing to CFUs (108) and introducing them by gavage into mice (9 per time point from triplicate experiments). Each mouse is assessed by counting total lactobacilli levels in fecal samples daily for 12 days (cultured on MRS agar).

In addition, this Example uses a real-time PCR method to assess 16S rRNA gene sequence copy numbers for the *Lactobacillus* genus (including some species of *Weisella*, *Pediococcus*, and *Leuconostoc* due to difficulties with primer specificity) and specifically for *L. reuteri*. The 16S rRNA gene copy numbers is determined in the feces daily for 12 days, as well as in the colon, cecum, small intestine (including ileum, jejunum, and duodenum), and stomach (including the forestomach) using real-time PCR on Days 1, 3, 6, and 12 post-oral inoculation. Sham mice with and without planktonic cells serve as controls. A significant increase in *L. reuteri* levels in mice treated with biofilm-grown *L. reuteri* in comparison to sham or planktonic-treated mice is an indicator of durability and robustness.

Example 4.2: Effects of Growth Conditions

One set of growth conditions has been used to date, standing cultures in MRS media (Jones, and Versalovic, (2009) Probiotic *Lactobacillus reuteri* Biofilms Produce Antimicrobial and Anti-Inflammatory Factors, BMC Microbiol, 9:35), at 37° C. While not an exhaustive list, here this Example varies the media, the prebiofilmics as well as pH and aerobicity.

Varying growth conditions in vitro. In this Example, other media to grow the biofilms instead of MRS including LB, THYE (THB with yeast extract), mTSB (modified tryptic soy broth) are used as *L. reuteri* grows in each to varying degrees. In addition, the Example also varies the starting pH to about 5.5, 6, 6.5 or 7 as *L. reuteri* growth is favored under more acidic conditions. While *L. reuteri* can be grown microaerophilically under 5% CO2, stressful conditions of times favor biofilm growth (Flemming, and Wingender, (2010) The Biofilm Matrix, Nat Rev Microbiol, 8:623-33); here *L. reuteri* biofilms are also grown in air or in the absence of oxygen (anaerobic chamber). Finally, the Example varies the prebiofilmics of HU (about 0.1, 1, 10, 100 µg/ml) and calf thymus DNA (about 0.1, 1, 10, 100 µg/ml). All the aforementioned biofilms are assessed by CSLM with LIVE/DEAD® staining in triplicate for height, average thickness and biomass as indicators of robust growth.

Varying growth conditions in vivo. Conditions optimal for biofilm growth are compared against both the initial standard conditions as well as the conditions that create the poorest biofilm (control). Biofilms are introduced by oral gavage into 9 mice (from triplicate experiments) for each trial under the conditions optimized in Example 4.1. Sham mice with and without planktonic cells serve as controls. *L. reuteri* levels are assessed as in Example 4.1, on Days 1, 3, 6, and 12 post-challenge.

Example 4.3: Effects of Bacterial Dosing

Dosing of *L. reuteri*; frequency and size. Rhe frequency and or size of dosing improves the durability and robustness of the introduction of *L. reuteri* are determined. *L. reuteri* biofilms are grown on PLGA microspheres with added HU and calf thymus DNA for 24 hours (or an age condition as determined in Example 4.1 and 4.2). *L. reuteri* biofilms are introduced to mice by oral gavage creating a matrix of varying the dose ($10^7$, $10^8$ and $10^9$ CFUs) as well as the frequency (single dose, or daily dose up to 3 days) yielding 9 different conditions. *L. reuteri* levels are assessed in vivo on Days 1, 3, 6, and 12 post gavage as outlined in Example 4.1. Nine mice (from triplicate experiments) for each condition at each time point are used. Sham mice with and without planktonic cells serve as controls.

Example 4.4: Testing Dispersed Biofilm Bacteria

Testing dispersed *L. reuteri* from biofilms. Dispersed bacteria for their endurance and robustness in the mouse gut are examined. *L. reuteri* biofilms can be dispersed by antisera to a DNABII family member (e.g., *E. coli* IHF). Here this Example tests the bacteria released (dispersed) due to anti-IHF treatment. 24 hour *L. reuteri* biofilms (no added PLGA, HU or DNA so as to facilitate dispersal) grown in chamber slides are treated with anti-IHF. As the peak of dispersal is about 8 to 12 hours after treatment (Goodman, et al. (2011) Biofilms Can Be Dispersed by Focusing the Immune System on a Common Family of Bacterial Nucleoid-Associated Proteins, Mucosal Immunol, 4:625-37), conditioned media containing dispersed *L. reuteri* after 12 hours of antibody treatment are used for introduction into mice by oral gavage. *L. reuteri* levels are assessed in vivo on Days 1, 3, 6, and 12 post challenge as outlined in Example 4.1. Nine mice for each time point (from triplicate experiments) with a similar number for controls using planktonic bacteria and optimized biofilm bacteria (Example 4.1 to 4.3) are used.

Biofilms are found to be superior for establishment, persistence and duration of probiotic bacteria in the gut. It is not just the biofilm per se that possesses superior features to planktonic bacteria but the bacteria that are dispersed from biofilms. In effect, the biofilm will act as a dispersed-bacteria generator. Indeed, physiologic differences in dispersed bacteria as compared to laboratory grown planktonic bacteria (e.g. in antibiotic sensitivity) have been ob served.

Example 4.5: Shelf Life

For reduction to practice and ease of use, *L. reuteri* preparations need to be in a sufficiently stable form.

Freezing. *L. reuteri* biofilms have been flash frozen and found no diminution in CFUs and minimum inhibitory concentration or MIC (>2 mg/ml ampicillin; MIC for planktonic *L. reuteri*<4 µg/ml) suggesting *L. reuteri* retains at least one property of its biofilm state, enhanced MIC. Optimized *L. reuteri* biofilms (Example 4.1. to 4.3) for ambient air freezing to −20° C. and −80° C. with and without glycerol (a cryo-protectant; See also Example 2) as well as flash freezing to −80° C. (placing storage tubes with fresh bacterial suspensions in dry ice-ethanol) are examined.

Media are first removed and the resulting biofilm are scraped off and treated to freeze. Bacteria are stored at these temperatures for 1 day, 1 week or 1 month and then thawed at ambient room temperature to be used for introduction into mice by oral gavage. Nine mice from triplicate experiments are used with a similar number for controls using planktonic bacteria and optimized biofilm bacteria (Example 4.1 to 4.3). Each mouse is assessed as in Example 4.1.

Desiccation. Optimized *L. reuteri* biofilms (Example 4.1. to 4.3) via lyophilization after freezing using the optimized technique in Example 4.5 are examined. Desiccated bacteria are stored at room temperature for about 1 day, 1 week or 1 month and then rehydrated with the original biofilm volume of sterile distilled water at ambient room temperature to be used for introduction into mice by gavage. Nine mice from triplicate experiments are used with a similar number for controls using planktonic bacteria and optimized biofilm bacteria (Example 4.1 to 4.3). Each mouse is assessed as in Example 4.1.

Finally, a strain of *L. reuteri* (ATCC23272) is utilized. Additional strains of *L. reuteri* (e.g. strain 100-23, ATCCPTA6475, ATCC55730) are also examined to assess strain differences. As an additional control, *L. reuteri* strains that are commercially available (Fleet® Pedia-Lax™ Probiotic Yums™~100 million CFU/tablet, *L. reuteri* Protectis®DSM 17938 and Gerber® Soothe Colic Drops~100 million CFU/serving (5 drops, ~200 ul), *L. reuteri* Protectis®DSM 17938) are examined. This Example finds that by dissolving each product in water and using them directly in in vitro competition experiments with *C. rodentium* each product is shown to be no better than the strain of *L. reuteri* in planktonic form.

Example 5: Dentification and Characterization of Biodegradable Surfaces and Pre-Biotic Substances to Facilitate the Endurance and Robustness of the Probiotic Biofilms Other types of microspheres as well as inherent cargo that may facilitate either probiotic growth or inhibit pathogens are explored.

Example 5.1: Testing Empty Microspheres

Empty microspheres in vitro, DNA, gelatin, Polylactic acid, Poly-α-caprolactone, chitosan and acetalated dextran are examined in this Example.

While PLGA microspheres are utilized as a surface to grow the biofilms, there are other FDA approved or GRAS biodegradable microspheres that may prove advantageous for the goals. As shown in Table 2, 5 additional types of microspheres are examined (Chellat, F. et al. (2000) In Vitro and in Vivo Biocompatibility of Chitosan-Xanthan Polyionic Complex, J Biomed Mater Res., 51:107-16; Costa, D. et al. (2012) Swelling Behavior of a New Biocompatible Plasmid DNA Hydrogel, Colloids Surf B Biointerfaces 92:106-12; Kauffman et al. (2012) Synthesis and Characterization of Acetalated Dextran Polymer and Microparticles with Ethanol as a Degradation Product, ACS Appl Mater Interfaces, 4:4149-55; Kumari et al. (2010) Biodegradable Polymeric Nanoparticles Based Drug Delivery Systems, Colloids Surf B Biointerfaces, 75:1-18; Sinha et al. (2004) Poly-Epsilon-Caprolactone Microspheres and Nanospheres: An Overview, Int J Pharm. 278:1-23; Topuz and Okay (2009) Formation of Hydrogels by Simultaneous Denaturation and Cross-Linking of DNA, Biomacromolecules 10:2652-61). Thus, DNA can be used as the microsphere material as it is the basis of the EPS for biofilms.

This is an example of an optimization strategy in vitro and in vivo from Example 4. Microspheres from materials in Table 2 and repeat Examples 4.1-4.5 are constructed. Microspheres that fail to support in vitro robust biofilm growth using height, thickness and biomass, as initial metrics; are no longer be considered. Likewise those microsphere types that subsequently fail to surpass in vivo metrics relative to planktonic bacteria are also no longer be considered. Shelf life with and without bacteria, stability at low pH (gastric conditions) are also contemplated.

and/or glycerol are made, as the former is restrictive to Gram-negative bacteria some of which are pathogens and the latter stimulates reuterin production (an antimicrobial molecule believed to give L. reuteri an advantage against competing bacteria). L. reuteri biofilm growth on these microspheres is performed on the conditions observed in Example 4 (or Example 5.1 with a variant microsphere) and is adjudicated by CSLM for height, thickness and biomass.

This example tests prebiofilmics in vitro. As in Example 4.2, the ability of prebiofilmics (HU and DNA) was examined as cargo in PLGA microspheres (and the microsphere types from Example 5.1) to support in vitro biofilm growth. In each case, biofilms are grown under the conditions observed in Example 4 with microspheres synthesized in the presence of HU and or DNA (so as to be encapsulated in the interior of the microsphere) and are adjudicated by CSLM for height, thickness and biomass.

This example tests a combination of prebiotics and prebiofilmics in vitro. Here a matrix of combinations of the two probiotic and two prebiofilmic cargos is created (all 16 combinations of two, all 4 combinations of 3, and the single combination of all 4 equaling 21 total combinations) to find the suitable prebiotics or prebiofilmics. In each case, biofilms are grown under the conditions observed in Example 1 with PLGA microspheres (and the microsphere types from Example 5.1) synthesized in the presence of cargo and are adjudicated by CSLM for height, thickness and biomass.

This example tests optimized components in vivo. Conditions from Example 5.2 that yielded the biofilms are used for in vivo experiments. The four most promising conditions for PLGA microsphere cargo (or the two most promising

TABLE 2

Types Of Biodegradable Polymeric Microspheres

| Type of Microsphere | Size Range(μm) | Degradation Products | FDA Approval |
| --- | --- | --- | --- |
| PLGA (poly-D,L,-lactide-co-glycolide)[a, b] | 20-300 | Lactic acid, Glycolic acid | X |
| PCL (poly-e-caprolactone)[a, c] | 10-500 | 6-hydroxyhexanoic acid 3-(2-hydroxyethoxy)propanoic acid | X |
| Chitosan[a, d] | 20-550 | Glucosamine, N-acetyl-D-glucosamine | X |
| Gelatin[a] | 35-100 | Amino acids | X |
| DNA (hydrogel)[e, f] | Variable | DNA, ethylene glycol diglycidyl ether | |
| Acetalated dextran[g] | 0.1-10 | Dextran, Acetone, Ethanol | |

[a]Kumari A, 2010, Colloid Surface B, supra.
[b]Beer S J, 1998, Gene Ther., supra.
[c]Sinha V R, 2004, Int J Pharm., supra.
[d]Chellat F, 2000, J Biomed Mater Res., supra.
[e]Costa D, 2012, Colloid Surface B., supra.
[f]Topuz F, 2009, Biomacromolecules., supra.
[g]Kauffman K J, 2012, App Mater Interfac., supra.

Example 5.2: Testing Prebiotic Nutrients and Additives that Favor Probiotics as Cargo The cargo of PLGA is known to diffuse slowly or not even at all relative to the rate of microsphere hydrolysis (Fredenberg, et al. (2011) The Mechanisms of Drug Release in Poly(Lactic-Co-Glycolic Acid)-Based Drug Delivery Systems—a Review, Int J Pharm, 415:34-52). Here microspheres with prebiotic cargo were synthesized and evaluated for their ability to support L. reuteri growth in vitro and in vivo in the mouse models.

This examines nutrients in vitro. As an initial test cargo is loaded into PLGA microsphere during their synthesis (so as to be encapsulated in the interior of the microsphere). These cargos include, but not limited to, inulin, fructo-oligosaccharides, and galacto-oligosaccharides as they support lactobacilli growth. In addition, microspheres with MRS media PLGA and two most promising other type of microsphere from Example 5.1) are tested on nine mice each derived from triplicate experiments. Each mouse is assessed as in Example 4.1 on Days 1, 3, 6, and 12 post-L. reuteri introduction. Sham mice (no bacteria) and planktonic bacteria serve as controls.

Example 5.3: Prebiotic Nutrients that Impede Pathogens

Microspheres containing various probiotic cargos to determine if they support pathogen biofilm growth are examined. The microspheres containing prebiofilmics come into contact with a pathogen (i.e., C. rodentium strain DBS120 (pCRP1::Tn5)) as well as probiotic.

This example tests pathogen impeding nutrients in vitro. The same prebiotic and prebiofilmic substances from Example 5.2, are used as cargo to grow in vitro biofilms. *C. rodentium* is grown in LB media and used to seed biofilms with PLGA and the aforementioned cargos. Biofilms is adjudicated by CSLM for height, thickness and biomass compared to empty PLGA microspheres.

This example tests pathogen impeding nutrients in vivo. Taking into consideration the results from in vitro biofilm data in Example 5.3, four cargos for *C. rodentium* biofilm growth and use them in vivo in mouse models are examined. Nine mice for each condition per time point (from triplicate experiments) are used with planktonic *C. rodentium* and sham (no bacteria) as controls. *C. rodentium* levels in the stool is determined via culture on all days post oral *C. rodentium* administration. On Days 1, 6, 12 and 24 post-oral *C. rodentium* administration, the colon is removed and transected longitudinally so that inflammatory cytokines (e.g., TNF-α), inflammatory mediators (e.g., inducible nitric oxide synthase (iNOS)), and chemokines (e.g., CCL2) can be assessed in half of the colon via real-time RT-PCR. In the second half of the tissue, immunohistochemistry is used to assess leukocyte infiltration into the colon (e.g., F4/80+ macrophages; myeloperoxidase (MPO)+polymorphonuclear cells). While the aforementioned immune components are necessary for protective immunity against *C. rodentium*, when produced in excess, they can lead to tissue-damaging colitis. Thus, colonic pathology is assessed via H&E staining on the second half of the tissue.

Thus, microsphere biofilm preparations can include alternative types of microspheres and varying cargo. It is Applicants' belief that biofilms (regardless of surface) are superior to planktonic bacteria at seeding probiotic colonization in vivo.

Non-limiting examples cargos, include without limitation specific effectors of innate immunity that reduce inflammation, part of the process leading to dysbiosis. For example, microspheres can comprise conditioned media from *L. reuteri* as *L. reuteri* produce such substances. Likewise other bacteria are within the scope of this disclosure, e.g., *C. rodentium* and *L. reuteri*, in general for pathologies due to dysbiosis.

Example 6: Characterization of *L. Reuteri*'s Capacity to Limit or Displace the Murine Gut Enteropathogenic Bacterium *C. Rodentium*

Previous examples have identified and characterized the means to create an *L. reuteri* biofilm with the good endurance and robustness in the murine gut while also examining how these conditions might affect the murine enteropathogenic *C. rodentium*. In this Example, the formulations of *L. reuteri* biofilms to determine if they can reduce the effects of *C. rodentium*, or even partially clear introduced or extant pathogen are examined.

Example 6.1: Testing Optimized *L. reuteri* Biofilm Growth Conditions in *C. Rodentium* Challenge; Making of *L. Reuteri*

In vitro challenge of *L. reuteri* with *C. rodentium*. This Example systematically determines which of the conditions improves *L. reuteri* prophylaxis against *C. rodentium* challenge. As shown in Table 3, the Example systematically performs in vitro experiments where *L. reuteri* is grown in biofilms (about 12, 24, and 48 hours biofilms to reflect varying age) and then treated with varying quantities of planktonic *C. rodentium* ($10^7$, $10^8$ and $10^9$ CFUs). *L. reuteri* biofilm growth conditions from Examples 4.2 (e.g., for prebiofilmics as the media for challenge needs to at least facilitate growth of both bacterial species) as well as 2.1, 2.2 and 2.3 are examined. Mixed biofilms are evaluated after 12 or 24 hours of treatment by CSLM and by plate counts on selective media to determine which species' architecture and numbers dominate under each condition. Controls include each bacterial species without the other under each condition (e.g., the addition of *C. rodentium* added to PLGA microspheres without *L. reuteri* in each chamber slide). All experiments are done in triplicate.

TABLE 3

| Optimal Conditions For *L. Reuteri* Vs. *C. Rodentium* Challenge | | |
|---|---|---|
| Condition | In vitro | In vivo |
| Example 1 | | |
| *L. reuteri* 6, 12, 18, 24, 36, 48, 72 hours biofilm | X | X |
| *L. reuteri* grown in different media (MRS, LB, THYE, mTSB) | X | |
| *L. reuteri* + HU at 0.1, 1, 10, 100 µg/ml | X | |
| *L. reuteri* + DNA at 0.1, 2, 10, 50 µg/ml | X | |
| *L. reuteri* grown at varying pH (5.5, 6, 6.5, 7) | X | |
| Optimal growth conditions | X | X |
| *L. reuteri* dose CFU/ml ($10^7$, $10^8$, $10^9$) | X | X |
| *L. reuteri* dosage frequency (1, 2, 3 days) | X | X |
| Dispersed *L. reuteri* bacteria | X | X |
| Shelf life of *L. reuteri* biofilm preparations (freezing, desiccation) | X | |
| Example 2 | | |
| *L. reuteri* + PLGA, PCL, chitosan, gelatin, DNA, acetalated dextran microspheres | X | |
| *L. reuteri* + nutrient/prebiofilmic/nutrient-prebiofilmic microspheres | | X |
| *L. reuteri* + 4 most promising conditions of loaded microspheres | X | X |
| Prebiotic nutrients that impede pathogens | X | X |
| Example 3 | | |
| *L. reuteri* 12, 24, 48 hours biofilm challenge of *C. rodentium* planktonic $10^7$ $10^8$, $10^9$ CFU | X | X |
| *C. rodentium* challenge of *L. reuteri* at 12, 24, 36 hours post-treatment with *L. reuteri* | | X |

TABLE 3-continued

Optimal Conditions For *L. Reuteri* Vs. *C. Rodentium* Challenge

| Condition | In vitro | In vivo |
|---|---|---|
| Established *C. rodentium* infection challenged by *L. reuteri* with top 3 conditions at $10^7$, $10^8$, $10^9$ CFU | X | X |

In vivo challenge of *L. reuteri* with *C. rodentium*. *L. reuteri* biofilm preparations for introduction into animals are prioritized based on the greatest retention or supremacy of *L. reuteri* observed. In addition, *L. reuteri* is prepared based on any successes derived from Examples 4.1, 4.4 and 4.5. In general, *L. reuteri* biofilms are introduced 12 hours prior to oral challenge with *C. rodentium*. Triplicate experiments are conducted for a final sample size of 9 mice for each condition and time point that are assessed at 1, 6, 12, and 24 days post-challenge (peak *C. rodentium* infection occurs at about Day 12). *C. rodentium* levels in the stool are assessed and pathogen-induced colitis is assessed as in Example 5.3. *L. reuteri* levels are also assessed as in Example 4.1. In every case, controls include *C. rodentium* without *L. reuteri* and *C. rodentium* challenge plus planktonic *L. reuteri*.

Example 6.2: Testing Dosing of Challenge Conditions

Dosing frequency and timing of *L. reuteri* with challenge by *C. rodentium* in vivo. This Example tests here how dosing of *L. reuteri* affect its ability to act as a prophylactic against *C. rodentium* challenge. The Example prioritizes the top three *L. reuteri* dosing conditions to reflect the most robust and durable results derived from Example 4.3. The Example then uses these conditions to challenge these *L. reuteri* treated mice with *C. rodentium* (about 12, 24 or 36 hours after the final *L. reuteri* treatment). Nine mice (from triplicate experiments) are used for each condition and time point. Vehicle mice infected with *C. rodentium* and single planktonic *L. reuteri* serve as controls. *C. rodentium* levels and pathogen-induced colitis are assessed on Days 1, 6, 12 and 24 post-challenge as in Example 5.3, with *L. reuteri* levels assessed as in Example 4.1.

Example 6.3 Testing Therapeutic Probiotic Challenge After Pathogenic Treatment Based on the Results in Examples 6.1, and 6.2

In Examples 6.1 and 6.2, conditions for using *L. reuteri* as a prophylactic against the pathologies caused by *C. rodentium* have been optimized. Here *C. rodentium* was introduced before *L. reuteri* to determine what effects challenge with *L. reuteri* has on extant *C. rodentium* pathogenesis.

Challenge of *C. rodentium* by *L. reuteri* biofilms in vitro. This Example shows that *L. reuteri* biofilms effectively challenged *C. rodentium* biofilms more effectively than planktonic *L. reuteri*. Here *L. reuteri* in biofilm form under conditions patterned after the three conditions from Example 6.1 is used. Briefly, *C. rodentium* biofilms (12, 24 or 36 hours) are challenged with *L. reuteri* biofilms ($10^7$, $10^8$ and $10^9$ CFUs). Mixed biofilms are evaluated after 12 or 24 hours after *L. reuteri* challenge of *C. rodentium* biofilms by CSLM and by plate counts on selective media to determine which species' architecture and numbers dominated under each condition, respectively. Controls include each bacterial species without the other under each condition (e.g., the addition of *L. reuteri* to chamber slides without extant *C. rodentium*). All experiments are done in triplicate.

Challenge of *C. rodentium* by *L. reuteri* biofilms in vivo. Here this Example determines if *L. reuteri* biofilms can challenge prior *C. rodentium* infection in the murine model. Three different *C. rodentium* conditions (single gavage 12, 24 or 36 hours) prior to challenge with *L. reuteri* were examined. Four *L. reuteri* biofilm conditions including dosing (Example 6.2) are used to challenge *C. rodentium*. At least two of these conditions are derived from Example 6.1. Nine mice from triplicate experiments are used to test each of these 12 conditions. Pathogen-induced colitis is assessed as in Example 5.3, with *L. reuteri* levels assessed as in Example 4.1.

Here, this Example determines how effective *L. reuteri* introduced in the form of a biofilm is as a prophylactic to *C. rodentium* challenge and as a treatment for extant *C. rodentium* infection. To date, *L. reuteri* under the conditions fails to clear pathogens like *C. rodentium*, so it's particularly important if conditions where a probiotic can prevent or even cure an enteropathogenic infection can be found. Results here provide a rationale for future probiotic approaches.

Finally, the in vitro assays are performed on other pathogens as a prelude to future in vivo experiments. Pathogens included in an in vitro survey are enteric pathogens with different modes of infection, including invasive pathogens (e.g., *Salmonella enterica* subspecies Typhimurium and *Shigella flexneri*), additional A/E pathogens (e.g., Enterohemorrhagic *E. coli* O157:H7; and Enteropathogenic *E. coli*), and toxin-producing pathogens (e.g., *Vibrio cholera* and Enterotoxigenic *E. coli*); the rate limiting step in these experiments is finding co-culturing conditions that sufficiently mimic the in vivo state.

Example 7: Statistical Analyses and Determination of Sample Size

Most of the experiments involve multiple parameters and groups. Thus, two, three, or four factor analysis of variance (ANOVA) are primarily used. As an example of the statistical approach, in Example 4.1, a between subject ANOVA is used with probiotic (i.e., probiotic vs. vehicle control), condition (i.e., biofilm vs. planktonic), and time of culture (i.e., 6, 12, 18, 24, or 36 hours) as between subjects variables. Because different groups of mice are harvested on Days 1, 3, 6, and 12 post-oral inoculation, day of harvest is also used as a between subjects variable.

A significant 4-way interaction is interpreted first using post hoc independent samples t-tests with Modified Bonferroni correction factor applied for multiple comparisons. Afterward, 3-way and 2-way interactions are interpreted via post hoc testing, followed by interpretation of main effects. This general approach is followed for both in vitro and in vivo experiments.

Because of the inherent variability of in vivo experiments, considerable time was spent determining the sample size that would be needed to identify statistically significant differences between groups. A power analysis conducted using preliminary data investigating *C. rodentium* levels after *L. reuteri* administration with six different groups (preliminary sample size of 6), a population mean of 3.95, and population variance of 0.75, indicated that to obtain statistical significance with α=0.05, while maintaining power at 0.8, a sample size of n=9 per condition per time point would be needed. Thus, all animal experiments involve a sample size of nine per treatment and time point. This is accomplished by combining data from triplicate experiments, each containing n=3 mice per treatment and time point.

Probiotics have been widely used for digestive health benefits, although few actually prevent pathogen colonization and reduce the inflammatory response. The effects of probiotic bacteria can be significantly improved by the manner in which they are introduced into the host; specifically by growing them in the form of a biofilm. The data suggest that colonization in vivo by the probiotic *L. reuteri* is greatly enhanced when grown as a biofilm compared to planktonic-grown cells. In addition, when *L. reuteri* was grown in the presence of a biodegradable surface (PLGA), colonization was also increased indicating that the conditions were optimized that allowed a vast improvement in regards to *L. reuteri* establishment within the host.

Unexpectedly and surprisingly, Applicants demonstrated both in vitro and in vivo that treatment of *L. reuteri* as a biofilm in the presence of PLGA prior to challenging with the bacterial pathogen *C. rodentium*, caused a significant reduction in the number of *C. rodentium* compared to planktonic *L. reuteri* treatment. These data reveal that a probiotic can colonize better when presented as a biofilm, indicating that the way in which bacteria are introduced can greatly reflect the outcome of disease.

Example 8

Probiotic microbes have also been shown to reduce anxiety and depression in otherwise healthy humans and laboratory animals. A combination of *Lactobacillus helviticus* and *B. longum* administered daily for 30 days was shown to reduce anxiety and depression in healthy human volunteers and in healthy rats (Messoudi et al. (2011) Beneficial psychological effects of a probiotic formulation (*Lactobacillus helveticus* R0052 and *Bifidobacterium longum* R0175) in healthy human volunteers. Br J Nutri, 105:755-764).

This experiment tests whether *L. reuteri* preparations are superior at reducing infectious colitis-induced sickness, anxiety-like, and depressive-like behaviors using the same experimental design as the above-noted studies assessing the effects on infectious colitis itself, with minor modifications. The primary difference is that animal behavior will be assessed as well as, circulating cytokines, circulating hormones, and neuronal activation in the brain.

To determine whether prophylactic *L. reuteri* can prevent *C. rodentium*-induced sickness, such as anxiety-like and depressive-like behavior, prophylactic treatment with *L. reuteri* biofilms is assessed to determine if *C. rodentium* will prevent bacterium-induced sickness, anxiety-, and depressive-like behaviors. Preparations of *L. reuteri* biofilms that are found to be superior in in vitro assays are administered to mice via oral gavage 12 hours prior to oral challenge with *C. rodentium*. Triplicate experiments are conducted for a final sample size of 9 mice for each condition and time point that are assessed at 1, 6, 12, and 24 days post-challenge (peak *C. rodentium* infection occurs about Day 12). At each time point, animal behavior is assessed for locomotor activity (such as on the open field test), anxiety-like behavior (such as in the light:dark preference test and elevated plus maze), depressive-like behavior (such as on the tail suspension test and Porsolt forced swim task), and sickness behavior (such as with the sucrose preference test). Blood serum cytokines associated with emotional and illness behavior (e.g., IL-1α/β and IL-6) are assessed on each day. Circulating corticosterone levels will also be assessed. Neuronal activation in the brain, especially the paraventricular nucleus of the hypothalamus, are assessed using c-Fos immunoreactivity.

Whether *L. reuteri* can be used as a therapeutic to treat *C. rodentium*-induced sickness, anxiety-like, and depressive-like behavior also is assessed. For example, the compositions are tested to determine whether treating an established *C. rodentium* infection will reduce sickness, anxiety-, and depressive-like behaviors. Preparations of *L. reuteri* that are found to be superior in in vitro assays are administered to mice via an oral gavage 12, 24, and/or 36 hours after oral challenge with *C. rodentium*. On days 1, 6, 12, and 24 post-*C. rodentium* challenge, animal behavior is assessed for locomotor activity (such as on the open field test), anxiety-like behavior (such as in the light:dark preference test and elevated plus maze), depressive-like behavior (such as on the tails suspension test and Porsolt forced swim task), and sickness behavior (such as with the sucrose preference test). Circulating cytokines associated with emotional and illness behavior (e.g., IL-1α/β and IL-6) are assessed on each day. Circulating corticosterone levels are also assessed. Neuronal activation in the brain, especially the paraventricular nucleus of the hypothalamus, are assessed using c-Fos immunoreactivity.

These examples permit to modify conditions to create a more robust and long-lasting probiotic, and once established, and allow us to test these conditions in an in vivo model that could ultimately reflect treatments for bacterial infections and human disease.

Example 9: NEC

Probiotic administration may be beneficial in the prevention of NEC. However, probiotics must be administered daily to achieve beneficial effects. Applicants describe herein a novel probiotic delivery system in which the probiotics are grown as a biofilm on the surface of prebiotic-loaded biocompatible microspheres, allowing enhanced and more durable efficacy with only a single treatment.

Following cesarean delivery, neonatal rats were subjected to experimental NEC [hypoxia/hypothermia/hypertonic feeds (stress)]. On day 1, pups were randomized to receive a single enteral dose of the following: (1) vehicle only (100 µL sterile water) (N=32); (2) $1 \times 10^9$ CFU/mL *Lactobacillus reuteri* (N=9); (3) prebiotic-loaded biocompatible microspheres (N=12); or (4) $1 \times 10^9$ CFU/mL *L. reuteri* coupled with prebiotic-loaded biocompatible microspheres (N=33). Control pups were unstressed (N=10). Pups were sacrificed when clinical signs of NEC developed or by 96 hours after birth. A verified histologic NEC injury grading system was used to measure the incidence and severity of NEC, with Grade 2 or greater injury considered to be consistent with NEC.

Figure 5A:
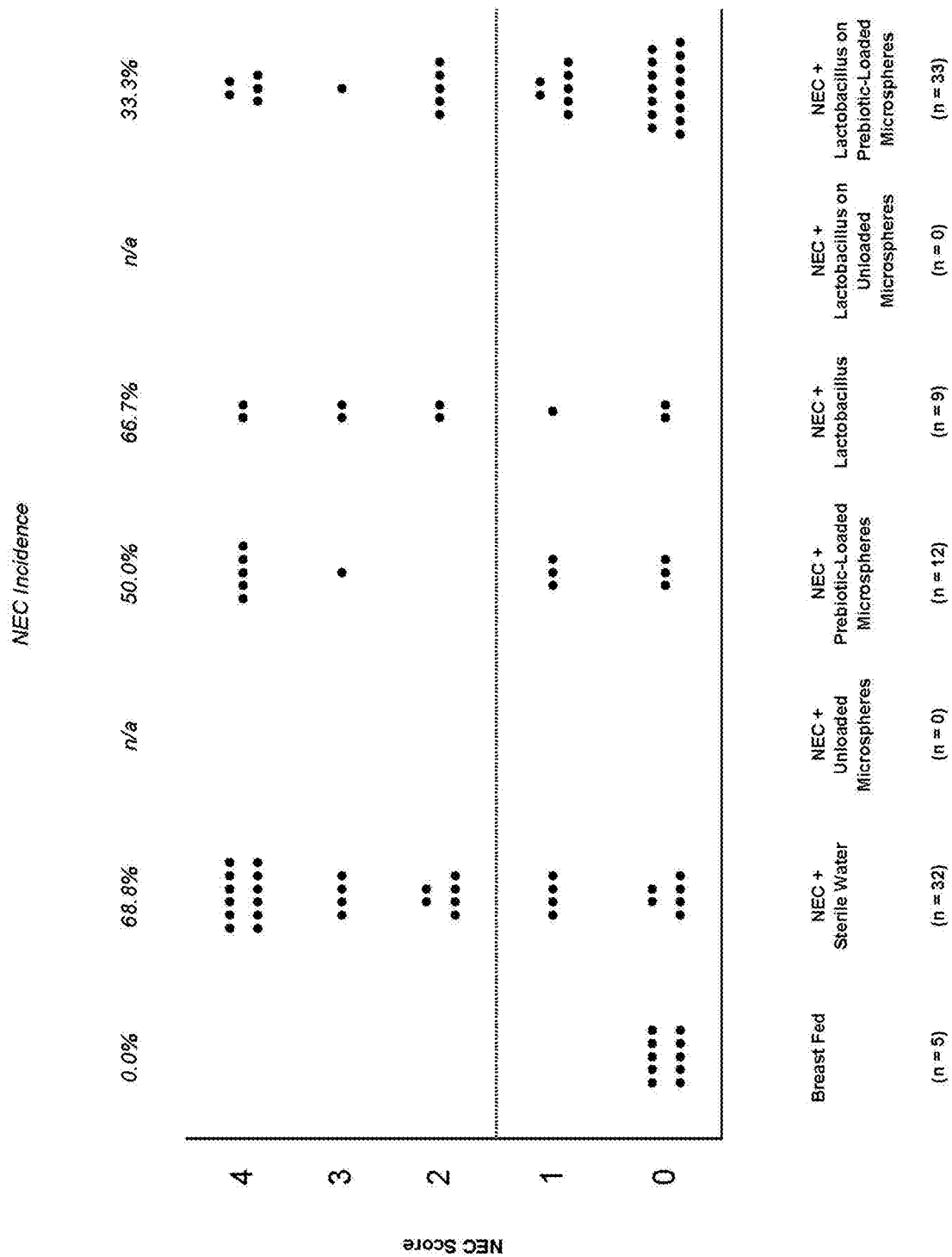
FIGS. 5A and 5B show the results of studies establishing that compositions of this disclosure are consistent with a reduction in inflammation and antagonization of bacterial pathogens in an animal model of NEC.
Figure 5B:
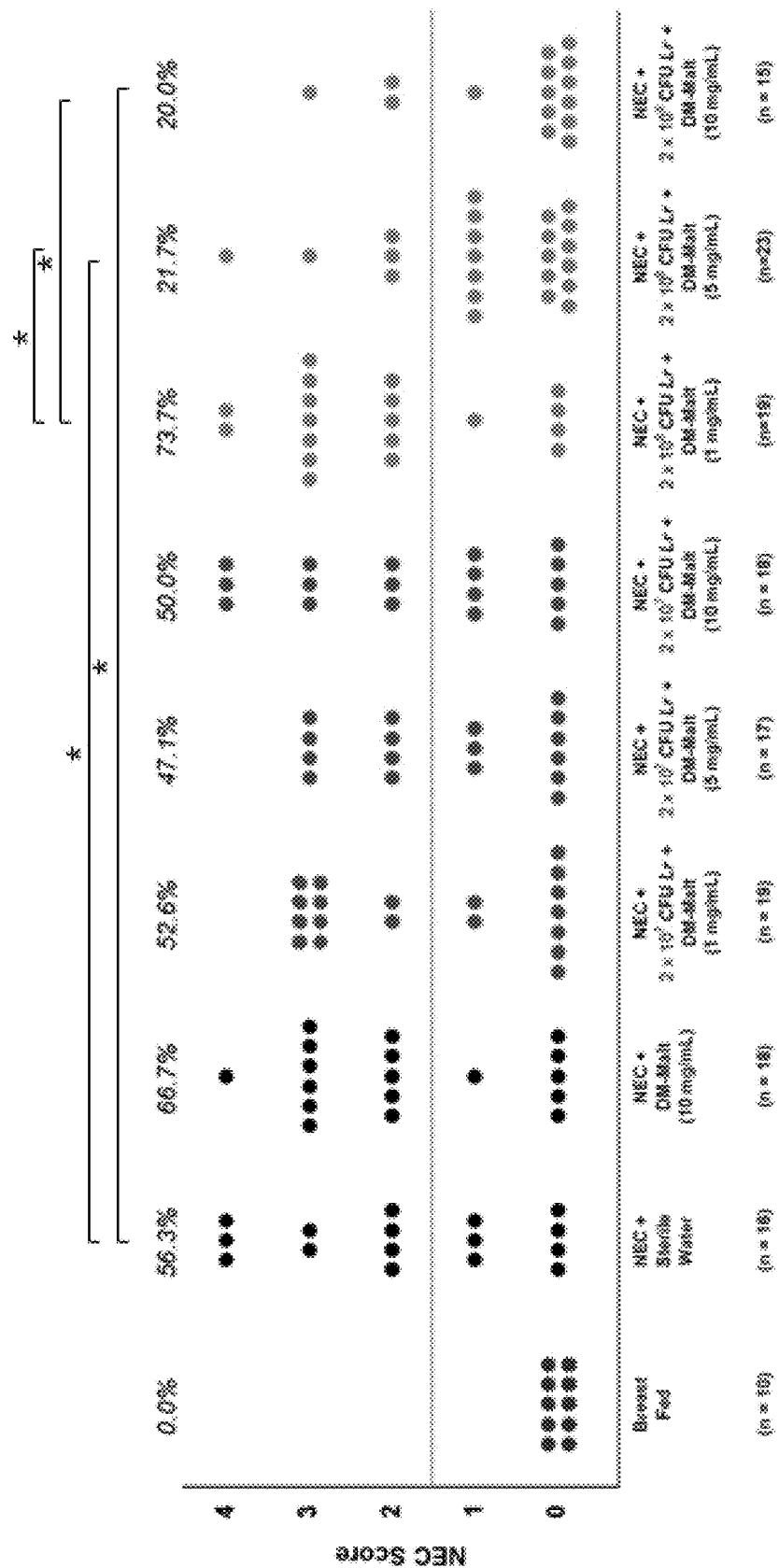

As graphically depicted in FIG. 5A, 69% of untreated stressed pups developed NEC. Compared to untreated stressed pups, 67% of pups treated with *L. reuteri* (p=0.329), 50% of pups treated with prebiotic-loaded microspheres (p=0.364), and 33% of pups treated with *L. reuteri* coupled with prebiotic-loaded microspheres (p=0.003) developed NEC. No unstressed pups developed NEC. As depicted in FIG. 5B, dosing of both *L. reuteri* and prebiotic-loaded microspheres showed that a sufficient number of *L. reuteri* (>$10^8$) and prebiotic microspheres (≥5 mg) was necessary for optimal prevention of NEC.

A single dose of a *Lactobacillus* biofilm coupled with prebiotic-loaded biocompatible microspheres reduces the incidence of NEC and therefore is an effective treatment. Without being bound by theory, the compositions as disclosed herein are prophylactic in their use in subjects in need of such treatment.

Example 10: Dessication Tolerance Assay

Another advantage of Applicants' invention is improved long-term survival of probiotic bacteria. A dessication tolerance assay was used to test stability and viability of the bacteria combined with the microspheres. The assay can generally be conducted by performing the following steps. To grow the bacteria culture, transfer 1 ml to a 1.5 ml of the culture to a microcentrifuge tube (1 tube per condition per time period to be tested). Add about 10 μl of hydrated microspheres, trehalose, or nothing to the tube. Incubate the tube for 30 minutes and then pellet the cells via centrifugation. Remove the supernatant and wash the pellet twice with sterile saline. Afterwards, remove all liquid from the pellet. Place the open tube on top of Drierite within an enclosed container and place the container into an incubator at 40° C. After 7 days, remove the tubes, rehydrate, and suspend the pellet in 1 ml of growth medium for 5 minutes. Then, serially dilute and plate for viable colony forming units. Finally, repeat rehydration and plating at 30 days and 90 days.

*P. fluorescens* and a proprietary *Azospirillum* sp. were placed after 90 days incubation at 40° C. while on top of Drierite, a strong desiccant, and then rehydrated and tested for viability. *P. fluorescens* with no microspheres shows a complete loss of colony forming units (CFU) after just one week in these conditions, whereas when incubated with cellulose microspheres, there are $10^5$ viable cells after 90 days in these conditions. *Azospirillum* sp. shows significant loss of CFUs after 30 days and complete loss after 90 days when grown without the microsphere formulation; however, when stored in harsh conditions with the microspheres, $10^6$ CFU/ml of *Azospirillum* sp. are viable even after 90 days.

Example 11: Acid Tolerance Protocol (48-Well Plate)

Microspheres filled with *L. reuteri* growth medium as cargo were utilized to provide a surface that leaches buffered nutrients to the bacteria for the formation of a biofilm that enhances survivability at low pH. Bacterial cells with microspheres show over a 2 log increase in viable colony forming units compared to cells without microspheres after sitting in pH 2 gastric acid for 4 hours. Further, *L. reuteri* with microspheres show increased adherence to mouse colonic cells, addressing the problem of poor colonization and sustainability of orally administered bacteria. Taken together, the novel microsphere formulations not only increase survivability at low pH, but also contribute to colonization of beneficial bacteria in the gut, making *L. reuteri* a more efficient probiotic.

An acid tolerance protocol assay, such as that used to generate the above information, can generally be conducted by performing the following steps. First, grow 5 ml culture overnight at 37° C. (5% $CO_2$ or anaerobically) and then dilute the culture 1:2500 in a fresh medium. Transfer 500 ml per condition per time period to be tested into a 48-well plate. Transfer ~10 ul of hydrated microspheres or nothing into the well. Afterwards, incubate at 37° C. 5% $CO_2$ (or anaerobically) for 20 hours overnight. At 20 hours, remove the spent media from the biofilm and replace with pH 2 gastric acid. At two and four hours, remove the acid from the biofilm and suspend cells by pipette mixing in the growth medium. Finally, serial dilute and plate the cells.

Example 12: Cellular Adherence Assay

Microspheres filled with *L. reuteri* growth medium as cargo were utilized to provide a surface that leaches buffered nutrients to the bacteria for the formation of a biofilm that enhances survivability at low pH. Bacterial cells with microspheres show over a 2 log increase in viable colony forming units compared to cells without microspheres after sitting in pH 2 gastric acid for 4 hours. Further, *L. reuteri* with microspheres show increased adherence to mouse colonic cells, addressing the problem of poor colonization and sustainability of orally administered bacteria. These results show that novel microsphere formulations not only increase survivability at low pH, but also contribute to colonization of beneficial bacteria in the gut, making *L. reuteri* a more efficient probiotic.

A cellular adherence assay, such as that used to generate the above information, can generally be conducted by performing the following steps. First, grow up a mammalian cell culture line and dilute to ~$10^6$ cells/ml. Transfer 500 ul of the diluted mammalian cell lines to a 48-well plate. Then, grow to confluence (time varies, at least 16 hours) and grow the bacterial culture overnight. Afterwards, transfer 500 ul of the bacterial culture to a 1.5 ml microcentrifuge tube (1 tube per condition per time period). Pellet the bacterial cells via centrifugation and wash the pellet 2-3 times to remove all growth medium. Resuspend the pelleted bacteria in a cell line culture medium. Add either microspheres hydrated in a cell line culture medium, microspheres hydrated in MRS, or nothing to the suspended bacteria.

Remove the growth medium from the confluent mammalian cell culture wells. Aspirate the bacterial conditions with cell line growth medium into mammalian cell culture wells. Incubate at 37° C. 5% $CO_2$. After 1 hour, remove the supernatant spent medium from each well and wash cells with sterile PBS twice to remove non-adhered bacteria. Add 500 ul trypsin to each well to dislodge adhered mammalian cells from the plastic and incubate at 37° C. for 5-10 minutes. Thoroughly mix the liquid in each well to resuspend the mammalian cells. Then, serially dilute and plate to calculate the number of bacteria that remained adhered to the mammalian cells. At 4 and 8 hours, remove the supernatant spent medium from each well and wash cells with sterile PBS twice to remove non-adhered bacteria. Add 500 μl trypsin to each well to dislodge adhered mammalian cells from the plastic and incubate at 37° C. for 5-10 minutes. Thoroughly mix the liquid in each well to resuspend the mammalian cells. Then, serially dilute and plate to calculate the number of bacteria that remained adhered to the mammalian cells.

Example 13: Enhanced Probiotic Potential

In one aspect, the probiotic formulation comprises *L. reuteri*'s extracellular glucosyltransferase (GTF) protein, which in the strain of *L. reuteri* used in this study (DSM 20016, containing GTFW encoded by gtfW) (Leemhuis et al., 2013; Bai et al., 2015) catalyzes the formation of exopolysaccharides of glucose (glucans) from its sole known substrate maltose. By way of background, GTF proteins typically have a glucan binding domain that recognizes its own produced exopolysaccharide (Monchois et al., 1999; Kralj et al., 2004). The GTF protein, its substrate, and resulting glucan product are highly strain-specific in *L. reuteri*; some are characterized as producing dextran (primarily α-1,6 linkages), mutan (primarily α-1,3 linkages), or the aptly named reuteran (primarily α-1,4 linkages) (Kralj et al., 2002; Kralj et al., 2004). Cell aggregation, biofilm formation, and gut colonization are directly linked to the activity of GTFA in *L. reuteri* strain TMW1.106; inactivating gtfA significantly diminishes the ability of *L. reuteri* to aggregate, form biofilms, and colonize the GI tract in vivo (Walter et al., 2008).

Applicants' novel approach comprises the selection of dextranomer microspheres [a macroscopic porous microsphere that is sold commercially for size exclusion chromatography (Porath and Flodin, 1959)] as a biocompatible surface so as to take advantage of *L. reuteri*'s GTFW native ability to bind to this cross-linked dextran (Tieking et al., 2005; Schwab et al., 2007; Walter et al., 2008). GTFW-dependent binding of *L. reuteri* to DMs results in: one, selectivity of binding to DMs and as a result better binding of *L. reuteri* to colonic epithelial cells; two, protection against low pH and three, the ability of *L. reuteri* to acquire the luminal contents of the DMs at sufficiently high concentrations to enhance *L. reuteri*'s probiotic effects.

Example 13.1: Strains and Culturing Conditions

Bacterial strains, plasmids and oligonucleotides used are listed in Table 5. *L. reuteri* (ATCC 23272) and *Lactobacillus rhamnosus* GG (ATCC 53103) were grown in MRS (de Man, Rogosa, Sharpe) medium (De Man et al., 1960) (BD, Franklin Lakes, N.J.) for 16 hours at 37° C., 5% $CO_2$. *Salmonella typhi* (strain JSG698) and *Citrobacter rodentium* (ATCC 51459) were grown in Lysogeny broth (LB, #63) at 37° C., 5% $CO_2$. *Clostridium difficile* (strain R20291) was grown in degassed brain-heart infusion (BHI) medium (BD, Franklin Lakes, N.J.) at 37° C. in an anaerobic chamber (Thermo Forma Scientific, 1025 Anaerobic System, Hampton, N.J.) established with an atmosphere of 5% $H_2$, 85% $N_2$, and 10% $CO_2$. DLD-1 (ATCC CCL-221) human colonic cells were grown in RPMI medium supplemented with 10% fetal bovine serum at 37° C., 5% $CO_2$. FHs 74 Int (ATCC CCL-241) human fetal small intestinal cells were grown in Hybri-Care medium (ATCC 46-X) supplemented with 30 ng/ml epidermal growth factor (EGF) and 10% fetal bovine serum at 37° C., 5% $CO_2$. The gtfW deletion strain (LMW500) was constructed by insertion of a chloramphenicol resistance cassette (Venereau et al.) into the gtfW open reading frame by allelic exchange as described previously (Mashburn-Warren et al., 2012). Briefly, 1 kb fragments upstream and downstream of gtfW were amplified by PCR using oligos oSG1082-1083 and oSG1084-1085, followed by cloning into pFED760 (Mashburn-Warren et al., 2012) using NotI/SalI and SalI/XhoI restriction sites respectively. The cat cassette was amplified from pEVP3 (Mashburn-Warren et al., 2012) using oligos LMW34-35, followed by cloning into pFED760 that contained the upstream and downstream fragments of gtfW using the SalI restriction site. The resulting gtfW knock-out construct plasmid (pWAR500) was then introduced into *L. reuteri* ATCC 23272 by electroporation. *L. reuteri* electrocompetent cells were prepared by growing 5 ml of culture in MRS at 37° C. with 5% $CO_2$ until $OD_{600\ nm}$ of ~1.0. Cells were then pelleted and resuspended in 10 ml of sterile cold 0.5M sucrose and 10% glycerol twice, followed by a final resuspension in100 µl sterile cold 0.5M sucrose and 10% glycerol. To this resuspension 1 µg of pWAR500 was added and the cell/DNA mixture was placed into an ice cold 2 mm electroporation cuvette (BioRad, Hercules, Calif.). Cells were electroporated at 2500V, 25 µF and 400Ω using a BioRad Gene Pulser Xcell (BioRad, Hercules, Calif.). Immediately after electroporation, cells were resuspended in 1 mL of MRS and incubated at 30° C. for 2 hours, followed by serial dilution and plating onto MRS agar containing 5 µg/ml chloramphenicol and incubated at 30° C. The mutant was selected and confirmed as previously described (Chang et al., 2011).

TABLE 5

Bacterial strains, cell lines, plasmids, and oligos used in this study.

| | Description | Source/reference |
|---|---|---|
| Bacterial Strains | | |
| *Lactobacillus reuteri* ATCC 23272 | Wild type (GTFW) | American Type Culture Collection |
| LMW500 | *L. reuteri* 23272 ΔgtfW; $Cm^R$ | This study |
| LMW501 | *L. reuteri* 23272 + pWAR501 $Cm^R$ | This study |
| LMW502 | *E. coli* ER2566 + pWAR502 | This study |
| LMW503 | *L. reuteri* 23272 + pWAR503 $Cm^R$ | This study |
| *Lactobacillus rhamnosus* GG ATCC 53102 | Wild type (non-dextran forming GTF) | G. Rajashekara |

TABLE 5-continued

Bacterial strains, cell lines, plasmids, and oligos used in this study.

| | Description | Source/reference |
|---|---|---|
| *Salmonella enterica* serovar *typhi* TY2 ATCC 700931 | Wild type (non-dextran forming GTF) | J. S. Gunn |
| *Citrobacter rodentium* ATCC 51459 | Wild type (non-dextran forming GTF) | American Type Culture Collection |
| *Clostridium difficile* R20291 (BI/NAP1/027) | Wild type (non-dextran forming GTF) | J. K. Spinler |
| Human Cell Lines | | |
| DLD-1 ATCC CCL-221 | Human colonic epithelial cells (colorectal adenocarcinoma) | G. E. Besner |
| FHs 74 Int ATCC CCL-241 | Human fetal small intestinal epithelial cells | G. E. Besner |
| Plasmids | | |
| pWAR500 | pFED760 (Mashburn-Warren et al., 2012) derivative containing cat and DNA fragments flanking gtfW to create insertion mutant; see Materials and Methods; $Cm^R$, $Erm^R$ | This study |
| pWAR501 | pJC136 (Mashburn-Warren et al., 2012) derivative containing the promoter region of gtfW upstream of the click beetle luciferase; see Materials and Methods; $Cm^R$ | This study |
| pWAR502 | pTXB1 derivative containing gtfW (with its stop codon); see Materials and Methods, $Amp^R$ | |
| pWAR503 | pJC156 (Mashburn-Warren et al., 2012) derivative containing the promoter region of elongation factor Tu (EF-Tu) upstream of the click beetle luciferase; see Materials and Methods; $Cm^R$ | This study |
| Oligos | | |
| oSG1082 | GCGTGGCGGCCGCCATTATTTTCATGTAGTGTATTT (SEQ ID NO. 9) | This study |
| oSG1083 | GCGTGGTCGACCTTTTTTATGTCCATAATCTATT (SEQ ID NO. 10) | This study |
| oSG1084 | GCGTGGTCGACGAAAATATTTAATATGAAAATGA (SEQ ID NO. 11) | This study |
| oSG1085 | GCGTGCTCGAGCCAAGCACTATTTCACGAGAAT (SEQ ID NO. 12) | This study |
| LMW34 | GCGTGGTCGACGATGAAAATTTGTTTGATTT (SEQ ID NO. 13) | Mashburn-Warren et al., 2012 |
| LMW35 | GCGTGGTCGACTTATAAAAGCCAGTCATTAG (SEQ ID NO. 14) | Mashburn-Warren et al., 2012 |
| oSG1102 | GCGTGCTCGAGCAACAAGAGTATCAGGGTAAAGC (SEQ ID NO. 15) | This study |
| oSG1103 | GCGTGGTCGACTCCTTCCCAATAGATGATTGATT (SEQ ID NO. 16) | This study |

TABLE 5-continued

Bacterial strains, cell lines, plasmids, and oligos used in this study.

| | Description | Source/reference |
|---|---|---|
| oSG1067 | GCGTGGTCGACATGGTAAAACGTGAAAAAAATGT (SEQ ID NO. 17) | This study |
| oSG1068 | GCGGCCGCTCCGCCAGCTTTTTCTAATAACT (SEQ ID NO. 18) | This study |
| oSG1120 | GCGTGGCTAGCATGAACCTGCCAACAATTCCTAA (SEQ ID NO. 19) | This study |
| oSG1126 | GCGTGGCTCTTCCGCATTAAATATTTTCTTGGTTT (SEQ ID NO. 20) | This study |
| oSG1069 | GCGTGCTCGAGCGCAAGAAATACAGTTTCTAATA (SEQ ID NO. 21) | This study |
| oSG1070 | GCGTGGTCGACAAACCTCCTGATAATTTACAAGT (SEQ ID NO. 22) | This study |

CmR: Chloramphenicol resistant;
ErmR: Erythromycin resistant;
AmpR: Ampicillin resistant.
*sequences in bold indicate restriction enzyme sequences.

To estimate transcription from the gtfW promoter ($P_{gtfW}$), the $P_{gtfW}$-CBluc reporter plasmid was constructed by amplifying the promoter region 350 bp upstream of the gtfW start codon (including the native ribosome binding site) by PCR using oligos oSG1102-1103. The resulting DNA fragment was inserted into pJC156 using the XhoI/SalI restriction sites. The click beetle luciferase (CBluc) gene was amplified from the *Streptococcus mutans* strain ldhCBGSm (Merritt et al., 2016) using oligos oSG1067-1068 and inserted downstream of the gtfW promoter region in pJC156 using SalI/NotI restriction sites. The resulting reporter plasmid pWAR501 was transformed into *L. reuteri* 23272 as described above to create the reporter strain LMW501.

The *E. coli* gtfW overexpression strain (LMW 502) was created by amplifying the *L. reuteri* gtfW open reading frame (including the stop codon) using primers oSG1120-1126. The resulting DNA fragment was inserted into pTXB1 (New England BioLabs, Ipswich, Mass.) using NheI/SapI restriction sites. The resulting plasmid, pWAR502 was then transformed into the *E. coli* expression strain ER2566 (New England BioLabs, Ipswich, Mass.) and selected on Luria-Bertani agar containing 100 µg/ml ampicillin and confirmed by DNA sequencing. This strain allows the overexpression of tagless GTFW protein.

To produce a *L. reuteri* strain constitutively expressing click beetle luciferase, a reporter plasmid was constructed by amplifying the promoter region 250 bp upstream of the elongation factor Tu (EF-Tu) start codon (including the native ribosome binding site) by PCR using oligos oSG1069-1070. The resulting DNA fragment was inserted into pJC156 using the XhoI/SalI restriction sites. The click beetle luciferase (CBluc) gene was amplified from the *S. mutans* strain ldhCBGSm (Merritt et al., 2016) using oligos oSG1067-1068 and inserted downstream of the EF-Tu promoter region in pJC156 using SalI/NotI restriction sites. The resulting reporter plasmid pWAR503 was transformed into *L. reuteri* 23272 as described above to create LMW503.

Example 13.2: Microsphere Preparation and Application

Figure 13:
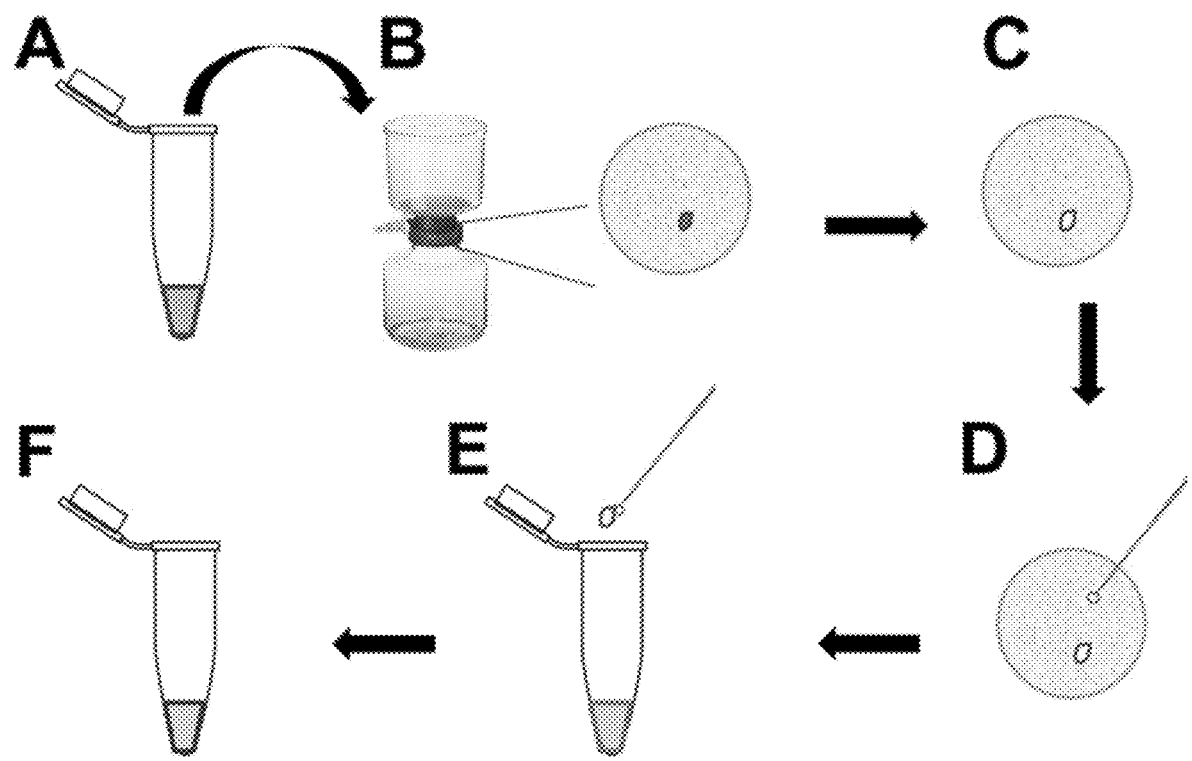
FIG. 13 is an illustration of DM cargo loading, filtration, and addition to bacterial culture. (A) Dehydrated DMs and desired cargo (e.g., 1M maltose) were incubated together to allow diffusion of solution into DMs. (B) The DM+solution is vortexed and pipetted to a vacuum filtration system. (C) The vacuum removes excess solution, leaving just DMs with absorbed cargo. (D) The DM-cargo pellet can now be removed from the vacuum filter by scraping with a sterile loop. (E) The DM-cargo pellet is transferred to a bacterial solution, typically bacteria resuspended in saline. (F) The final product is bacteria+DM-cargo together in solution, which can then be used for downstream applications (e.g., assays, oral gavage, etc.).

Anhydrous dextranomer microspheres (DMs; Sephadex® G-25 Superfine) were purchased from GE Healthcare Life Sciences (Pittsburgh, Pa.). Anhydrous cellulose microspheres (CMs; Cellulobeads D50) were obtained from Kobo Products, Inc. (South Plainfield, N.J.). Anhydrous microspheres were hydrated in growth medium or water at 50 mg/ml then autoclaved for 20 minutes. For conditions with microspheres that contained maltose, sucrose, fructose, or glucose only, microspheres previously autoclaved in water were removed from solution on a vacuum filter apparatus and approximately 50 mg were collected via sterile loop into 1 ml of filter-sterilized 1M solution of the sugar (see FIG. 13). The microsphere mixture was then vortexed vigorously and incubated for 24 hours at room temperature to reach equilibrium.

For application with *L. reuteri*, microspheres loaded with water, 1M maltose, 1M sucrose, 1M glucose, or 1M fructose were removed from solution on a vacuum filter apparatus and collected via a 10 µl sterile loop. Approximately 5 mg of hydrated microspheres were then added to 1 ml of $2 \times 10^9$ CFU *L. reuteri* from an overnight culture that had previously been pelleted by centrifugation at 3220×g for 10 minutes, washed twice with sterile 0.9% saline, and resuspended in 1 ml sterile saline. For experiments involving eukaryotic cell lines, $2 \times 10^9$ CFU of bacteria were resuspended in 1 ml RPMI instead of saline. For experiments with no microspheres but equivalent volume of cargo, 10 µl of cargo was added to 1 ml of bacteria either in sterile saline or RPMI. For all experiments, the bacteria and microsphere mixture were incubated together at room temperature for 30 minutes (unless otherwise stated) to facilitate bacterial adherence and biofilm formation on the microsphere surface prior to use in assays.

Example 13.3: Microsphere Adherence Assay

Figure 14:
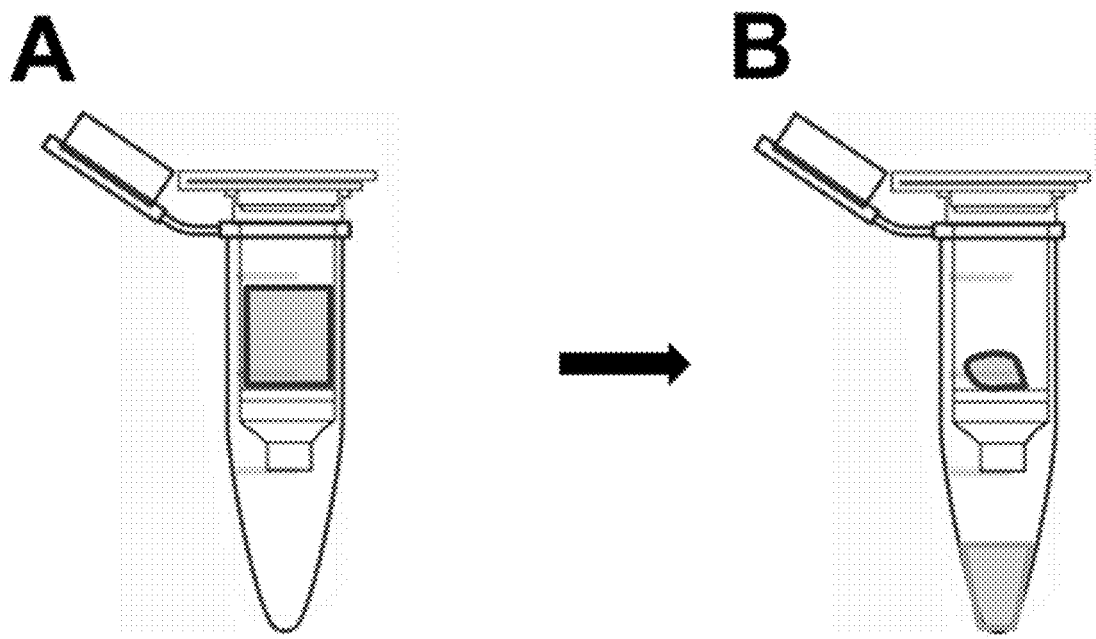
FIG. 14 is an illustration of spin column DM adherence assays. (A) A bacteria+DM-cargo mixture is incubated together on top of a spin column filter within a 1.5 or 2.0 ml microcentrifuge tube. After the desired incubation time (e.g., 5 minutes), the tube+column is centrifuged at ≤100×g to separate adhered and non-adhered bacteria to DMs. (B) After centrifugation, non-adhered cells will be in the flow through at the bottom of the microcentrifuge tube, and adhered bacteria to DMs will remain on the surface of the filter with the DMs (filter pore size is too small for DM passage, but small enough for bacterial cells). The cells present in the flow through are enumerated by serial dilution plating. A bacteria only (no DMs) control is used as a baseline, and all DM experiments are subtracted from the baseline.

*L. reuteri* culture was grown and prepared as described above and incubated with microspheres filled with either: water, 1M maltose, 1M sucrose, 1M fructose, or 1M glucose. To examine bacterial adherence to the microspheres, 300 µl of bacteria (from an overnight culture containing ~$2 \times 10^9$ CFU) in sterile saline and 5 mg of microspheres were combined and incubated for 5 minutes in a Micro Bio-Spin column (BioRad, Hercules, Calif.) (see FIG. 14). The columns were then centrifuged (100×g) for 1 minute. The flow-through was serially diluted and plated to calculate the total number of non-adhered bacteria, and this value was subtracted from the total number of starting bacteria to derive the total number of adhered bacteria. For all experiments, a control preparation that consisted of bacteria with no microspheres was used.

Example 13.4: Reporter Assay

The reporter strain LMW501 was grown at 37° C. with 5% $CO_2$ in MRS or MRS containing 3% glucose, sucrose, fructose, or maltose and optical densities ($OD_{600\ nm}$) of the cultures were measured throughout growth using an Epoch Microplate Spectrophotometer (BioTek Instruments Inc., Winooski, Vt.). At the indicated times, 80 µl aliquots of the bacterial cultures were mixed with 20 µl 2 mM D-luciferin in 0.1M citrate buffer, pH 6.0 and placed in a Falcon white flat-bottom 96-well plate (Becton, Dickinson Labware, Franklin. Lakes, N.J.), followed by kiminescence detection using a Veritas Microplate Luminometer (Turner BioSystems Inc., Sunnyvale, Calif.).

Example 13.5: GTF Enzymatic Assay

*S. mutans* was grown in Todd Hewitt Broth at 37° C. with 5% $CO_2$ until early log phase ($OD_{600\ nm}$~0.3), *L. reuteri* WT and the ΔgtfW mutant were grown in MRS at 37° C. with 5% $CO_2$ until late log phase ($OD_{600\ nm}$~1.0) for optimal gtf expression, and the *E. coli* gtfW overexpression strain was grown in Luria-Bertani broth at 37° C. shaking (200 rpm) until mid-log phase ($OD_{600\ nm}$~0.4) followed by the addition of 1 mM IPTG to induce gtfW expression and was then grown at 37° C. shaking for an additional 2 hours. Whole cells of *S. mutans*, *L. reuteri* WT, *L. reuteri* ΔgtfW, and the *E. coli* gtfW overexpression strain were assayed for GTF activity as previously described (Bai et al., 2015) using Periodic acid-Schiff staining of SDS-PAGE gels.

Example 13.6: Cargo Diffusion Assay

The rate of cargo diffusion out of the microspheres was determined by tracking crystal violet, a small molecular weight dye (407.979 g/mol) (Fisher Scientific, Hampton, N.J.). The microspheres were loaded with a 0.1% solution of crystal violet by incubating 20 mg of microspheres in 1 ml of 0.1% crystal violet solution either with or without added glycerol (40% or 80% v/v) overnight to reduce the diffusion rate by increasing viscosity. After 16 hours, excess crystal violet solution was removed from the microspheres as described above using a vacuum filter apparatus. The crystal violet-loaded microspheres were then placed into 1 ml of water, and aliquots of water were removed and analyzed for diffusion of crystal violet into solution using an Epoch Microplate Spectrophotometer (BioTek, Winooski, VT) at $OD_{590\ nm}$ every hour for 16 hours. Percent diffusion was calculated using the equivalent amount of crystal violet within the microspheres (10 µl) in water as a control equivalent to 100% cargo diffusion.

Example 13.7: Reuterin Assay

Production of reuterin by *L. reuteri* was measured via a quantitative colorimetric assay (Cadieux et al., 2008). As this assay did not differentiate between similar aldehyde products, measurements included 3-HPA and any potential derivatives, such as acrolein and 3-HPA hydrate. *L. reuteri* was grown overnight in MRS as described above, 1 ml aliquots of 2×10$^9$ CFU were pelleted at 3220×g for 10 minutes, washed twice with sterile saline, and resuspended in either 1 ml of sterile saline or 1 ml sterile saline containing 2% v/v glycerol. DM containing 0%, 2%, 10%, 20%, 30%, 40%, 50%, 60%, 70%, or 80% glycerol were prepared as described above for other cargo, and added to the resuspended *L. reuteri* in saline (so that the only source of glycerol available for reuterin production was via the microsphere cargo) for 1 hour at 37° C. Cells were then pelleted again and the reuterin-containing supernatant was removed, filtered through a 0.45 µm filter, and assayed for reuterin as described in Cadieux et al., 2008 without modification. A standard curve using reuterin at known concentrations was used to extrapolate bacterial-produced reuterin concentrations from DM-glycerol and the 2% v/v glycerol control experimental conditions.

Example 13.8: *L. Reuteri* Survival with DM-80% Glycerol

Overnight cultures of WT *L. reuteri* were aliquoted into microcentrifuge tubes, centrifuged, washed twice with sterile saline, and resuspended in either 1 ml saline or 1 ml MRS medium. 5 mg of either DM-water or DM-80% glycerol were then added to the tubes and incubated at 37° C. At hourly intervals the tubes were mixed thoroughly and aliquots were taken for subsequent serial dilution and plating for viable CFU of bacteria.

Example 13.9: Histamine Assay

Production of histamine from L-histidine by *L. reuteri* was measured via ELISA (Enzo Life Sciences, Inc., Farmingdale, N.Y.). *L. reuteri* was grown overnight in MRS as described above, 1 ml aliquots of 2×10$^9$ CFU were pelleted at 3220×g for 10 minutes, washed twice with sterile saline, and resuspended in one of the following conditions: sterile saline, saline with 3% maltose, saline with 2% v/v glycerol, 4 mg/ml L-histidine (Sigma-Aldrich, St. Louis, Mo.), 4 mg/ml L-histidine with 3% maltose, or 4 mg/ml L-histidine with 2% v/v glycerol. 5 mg of DM containing either 4 mg/ml or 30 mg/ml L-histidine were added to media lacking L-histidine, so that the only source of L-histidine for *L. reuteri* was as cargo diffusing out of the DMs. Each condition was then incubated at 37° C. for 2 hours, after which time the contents were pelleted and the supernatant was removed for histamine quantification via a histamine ELISA kit (Enzo Life Sciences, Inc., Farmingdale, N.Y.) following the manufacturer's instructions without modifications. All conditions were done in at least triplicate.

Example 13.10: pH Survivability Assay

Bacteria were exposed to a synthetic gastric acid equivalent to determine survival at pH 2. Gastric acid equivalent is a modified version of synthetic gastric fluid (Cotter et al., 2001), composed of 0.1M HCl, 0.1M NaCl, and 0.01M KCl, with pH adjusted to 2 using 0.1M NaOH. For the assay, 1 ml of 2×10$^9$ CFU of *L. reuteri* from a fresh overnight culture were pelleted at 3220×g for 10 minutes, washed twice with sterile saline, and resuspended in 1 ml 0.9% sterile saline. The cells were incubated for 30 minutes with approximately 5 mg of loaded or unloaded microspheres as described above, and the bacteria-microsphere mixture was diluted 1:100 directly into gastric acid equivalent. Aliquots of the inoculated acid solution were mixed, serially diluted, and plated at hourly time points for 4 hours to determine the number of viable bacteria. Bacteria without microspheres were used as a control.

Example 13.11: Adherence to Intestinal Epithelial Cells

DLD-1 colonic cells and FHs 74 small intestinal cells were cultured as described above. When the adherent epithelial cells reached confluence, the growth medium was removed, cells were washed twice with sterile phosphate buffered saline (PBS), and trypsin-EDTA (0.25%) was added for 10 minutes at 37° C. to dislodge the cells from the culture flask surface. Total epithelial cells were counted using a hemacytometer (Hausser Scientific, Horsham, Pa.). Cells were then diluted to a concentration of $5\times10^5$ cells/ml and 1 ml per well was seeded into a 24-well plate and incubated at 37° C., 5% $CO_2$. After either 48 hours (for DLD-1 cells) or 120 hours (for FHs 74 cells) of growth, the spent medium was removed and replaced with 1 ml of RPMI or Hybri-Care medium containing $2\times10^9$ CFU of $L.$ $reuteri$ alone, $L.$ $reuteri$ with 5 mg water-filled DMs, $L.$ $reuteri$ with 5 mg sucrose-filled DMs, or $L.$ $reuteri$ with 5 mg maltose-filled DMs. After a one hour incubation, the spent medium was removed and the well was washed with 1 ml of sterile PBS 3 times to remove non-adhered bacteria. The remaining epithelial cells, with adhered bacteria, were then trypsinized as described above, serially diluted, and plated onto solid MRS medium for enumeration of total adhered bacteria. For confocal microscopy experiments with DLD-1, Nunc Lab-Tek 8-well borosilicate chamber slides (Fisher Scientific, Hampton, N.J.) were used in place of 24-well plates. The chamber slides were treated with collagen prior to DLD-1 seeding to improve cellular adherence using the following protocol: a mixture of 100 µl of 7.5% BSA (Sigma-Aldrich, St. Louis, Mo.), 50 µl of 3.79 mg/ml collagen (Millipore, Temecula, Calif.), 100 µl of 1 mg/ml rat fibronectin (Biomedical Technologies, Stoughton, Mass.), and 9.75 ml of PBS was prepared, and 200 µl of this solution was added per chamber slide well. After incubation for 1 hour at 37° C., the solution was removed from the well, and epithelial cells were seeded and grown as described above.

Example 13.12: Mucin Adherence Assay

Mucin agar plates were created using porcine stomach mucin (Sigma-Aldrich, St. Louis, Mo.). Mucin agar plates contained 2% mucin and 0.8% agar to simulate the consistency of the mucus layer found in vivo (Macfarlane et al., 2005; Van den Abbeele et al., 2009). To assess $L.$ $reuteri$'s ability to bind mucin, $2\times10^9$ CFU of $L.$ $reuteri$ that contained a plasmid that encoded expression of the click beetle luciferase enzyme either planktonically or bound to 5 mg DM-water, DM-sucrose, or DM-maltose were incubated on both mucin agar and agar without mucin stationary at room temperature. After 60 minutes, the non-adhered $L.$ $reuteri$ were removed by washing the plates twice with sterile saline. The luciferase substrate D-luciferin (Sigma-Aldrich, St. Louis, Mo.) was then added to the plates at a concentration of 0.4 mM to visualize the remaining adhered bacteria. Relative luminosity generated from the bacteria on the plates was measured using a FluorChem E system (Protein-Simple, San Jose, Calif.) with a 20 minute exposure setting. To assess the number of bacteria bound to the mucin within the plate (and not any background binding that may occur to the agar within the plate), the amount of luminescent signal from the agar-only plates was subtracted from the mucin agar plates.

Example 13.13: Confocal Microscopy

All confocal laser scanning microscopy (CLSM) was performed using a Zeiss LSM 510 confocal microscope (Ziess A G, Oberkochen, Germany). For fluorescent staining, dextranomer and cellulose microspheres were pre-stained with Congo Red (Fisher Scientific, Hampton, N.J.) prior to incubation with the cargo (e.g. sucrose) and experiments with bacteria. $L.$ $reuteri$ was stained with SYTO 9 (Life Technologies, Carlsbad, Calif.). Differential fluorescent visualization was performed using the following settings: Congo Red excitation 554 nm/emission 568 nm, and SYTO 9 excitation 490 nm/emission 525 nm. Samples were fixed using a custom biofilm fixative containing 1.5% paraformaldehyde, 0.025% glutaraldehyde, 4.0% acetic acid, and 0.1M phosphate buffer at pH 7.4 (Devaraj et al., 2015). All microscopy was performed on samples in Nunc Lab-Tek 8-well borosilicate chamber slides (Fisher Scientific, Hampton, N.J.). For CLSM experiments with DLD-1 epithelial cells, DLD-1 was stained with 4',6-Diamidino-2-Phenylindole (DAPI, Life Technologies, Carlsbad, Calif.), $L.$ $reuteri$ was stained with carboxyfluorescein succinimidyl ester (CFSE, Life Technologies, Carlsbad, Calif.). AxioVision software (Ziess A G, Oberkochen, Germany) and ICY (de Chaumont et al., 2012) were used to analyze images and create figures from CLSM images. COMSTAT (Heydorn et al., 2000) software was used to quantify bacterial biomass in CLSM images.

For in vitro biofilm assays, overnight cultures of WT and ΔgtfW $L.$ $reuteri$ were diluted into fresh MRS growth medium to 0.01 $OD_{600\ nm}$, incubated at 37° C. 5% $CO_2$ for 2.5 hours until reaching 0.65 $OD_{600\ nm}$, diluted 1:2500 into either MRS, MRS+3% sucrose, or MRS+3% maltose, seeded into 8-well borosilicate chamber slides and incubated for 1, 3, or 6 hours at 37° C. 5% $CO_2$. At the designated time intervals, the bacteria were stained for viability with LIVE/DEAD stain, fixed, visualized via confocal microscopy, and quantified via COMSTAT analysis of the fluorescent signal.

Example 13.14: Scanning Electron Microscopy

All scanning electron microscopy (SEM) was performed using a Hitachi S-4800 field emission SEM (Hitachi, Tokyo, Japan). Samples were prepared as described in "Adherence to colonic cells", with the exception that DLD-1 human colonic epithelial cells were grown on 15 mm diameter thermanox coverslips (Electron Microscopy Sciences, Hatfield, Pa.) placed within the well of a 12-well plate. Samples of DLD-1 cells and adhered bacteria were fixed overnight at 4° C. in a solution of 2.5% glutaraldehyde in 0.1M phosphate buffer (pH 7.2). Samples were then washed with double distilled water and stained with a 1% solution of osmium tetroxide (Sigma-Aldrich, St. Louis, Mo.) in 0.1M phosphate buffer (pH 7.2) for 1 hour, washed for 5 minutes, stained with a 1% solution of thiocarbohydrazide (Sigma-Aldrich, St. Louis, Mo.), washed for 5 minutes, and further stained with 1% osmium tetroxide for 30 minutes. Samples were then dehydrated using a graded series of ethanol: 25% ethanol for 15 minutes, 50% ethanol for 15 minutes, 70% ethanol for 30 minutes, 95% ethanol for 15 minutes (twice), 100% ethanol (twice), a 1:1 mixture of 100% ethanol to 100% hexamethyldisilazane (HMDS, Sigma-Aldrich, St. Louis, Mo.) for 100 minutes, 100% HMDS for 15 minutes, and a final immersion in 100% HMDS that was allowed to air dry overnight. Dehydrated sample coverslips were then mounted onto 15 mm diameter metal SEM specimen stubs (Electron Microscopy Sciences, Hatfield, Pa.) using colloidal silver (Electron Microscopy Sciences, Hatfield, Pa.). The outer edge, where the stub and coverslip meet, was then coated with a light layer of colloidal silver, and allowed to dry overnight. Samples were sputter coated with gold and palladium for 2 minutes at 25 mA using an Emitech K550X sputter coater (Quorum Technologies Ltd., Laughton, United Kingdom).

Example 13.15: Statistical Analysis

All experiments were conducted a minimum of three times and statistical analysis was performed via a Student's t-test using GraphPad Prism software (GraphPad Software, Inc., La Jolla, Calif.), wherein a P-value less than 0.05 was accepted as significant.

Results

Example 13.16: Maltose or Sucrose within the Lumen of DMs Improved *L. reuteri* Adherence to DMs in a GTF-Dependent Manner Dextranomer microspheres (DMs) were differentially stained with Congo Red and *L. reuteri* were differentially stained with SYTO 9, and examined binding via confocal laser scanning microscopy (CLSM) to determine if probiotic bacteria would adhere to a bicompatibel surface and induce the formation of a biofilm. As shown in FIGS. 6A-6C, aggregates of bacteria were associated with the surface of numerous DMs which indicated that *L. reuteri* was able to adhere to the DM surface within the time allotted. Since DMs are cross-linked glucan similar to the native reuteran produced by *L. reuteri*, without being bound by theory Applicants hypothesized that either an increase in GTFW (for enhanced binding to DMs) or production of glucan to stimulate aggregation and biofilm formation would facilitate the adhered state of *L. reuteri*. To this end, adherence of *L. reuteri* to DMs that contained luminal cargo of either sucrose (an inducer of gtfW expression but not a substrate for GTFW; see FIGS. 15A & 15B) or maltose (the sole substrate of GTFW) were compared. As shown in FIGS. 6B & 6C, compared to DMs that contained only water within the lumen (FIG. 6A) there were greater numbers of *L. reuteri* adhered to DMs with either sugar as cargo.

Figure 15A:
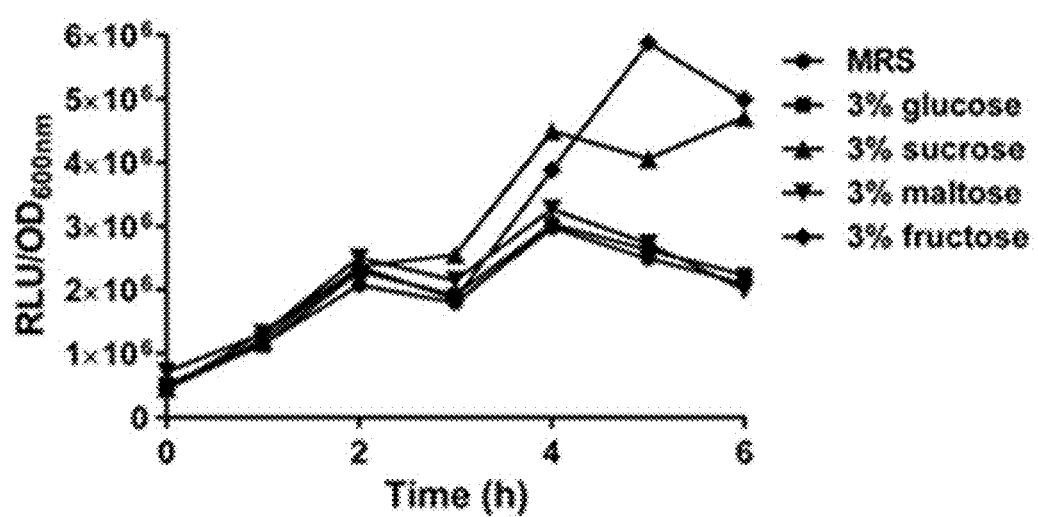
FIGS. 15A and 15B show that sucrose induces gtfW, but maltose is the substrate for GTFW.
Figure 15B:
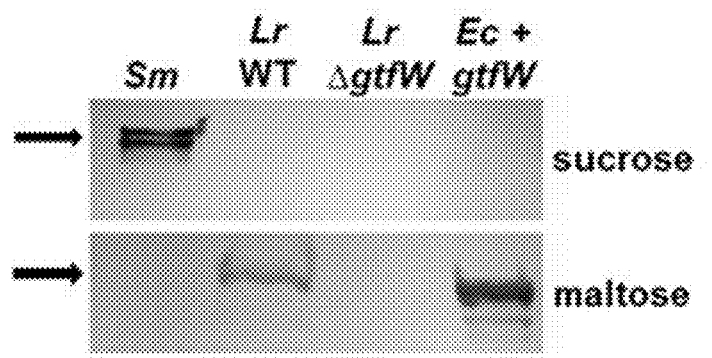

To further investigate *L. reuteri*'s ability to bind DMs, other DM lumen compounds were tested on the theory that the materials should not affect GTFW protein mediated binding and thus unlikely to support increased adherence to DMs. For this assay, the monosaccharide subunits of maltose and sucrose (e.g., glucose for maltose, glucose and fructose for sucrose) were chosen because the GTF enzyme cannot utilize them to catalyze glucan polymers. Interestingly, fructose (and not glucose) was shown to induce gtfW expression at a rate similar to sucrose, but did not result in enhanced binding to DMs as was found with sucrose (FIG. 15A, FIG. 7A).

Figure 7C:
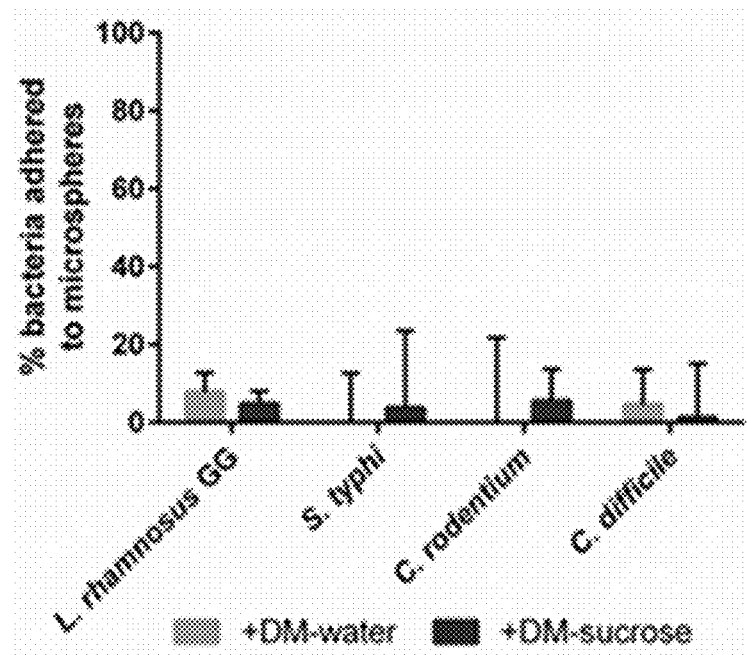
Figure 16A:
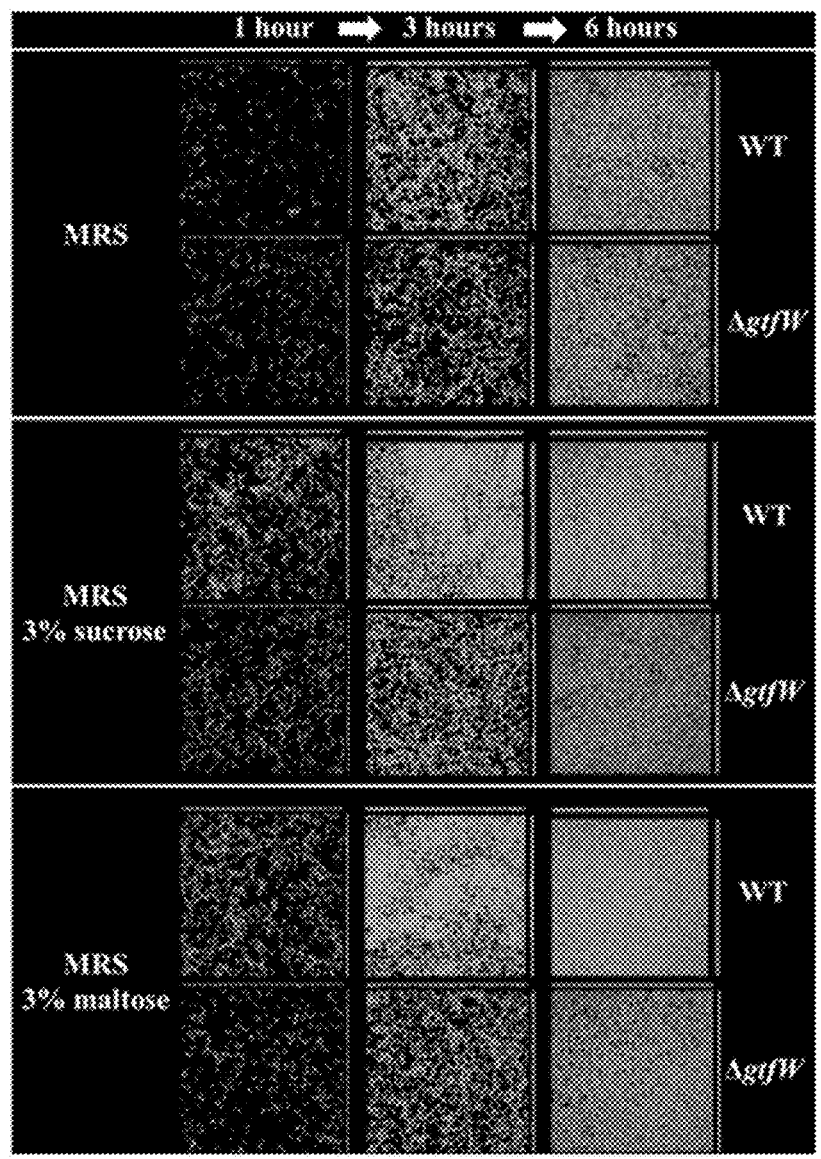
FIGS. 16A-16D show that GTFW contributed to early biofilm formation in growth medium supplemented with sucrose or maltose. *L. reuteri* WT and ΔgtfW were seeded into 8-well borosilicate chamber slides and incubated for 1, 3, or 6 hours at 37° C. 5% $CO_2$. At the designated time intervals, the bacteria were stained for viability with LIVE/DEAD stain, fixed, visualized via confocal microscopy (CLSM), and quantified via COMSTAT analysis of the fluorescent signal.
Figure 16B:
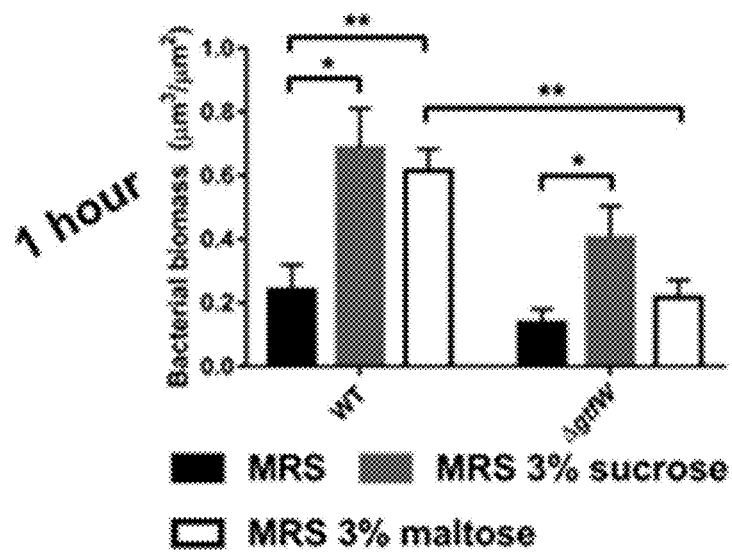
Figure 16C:
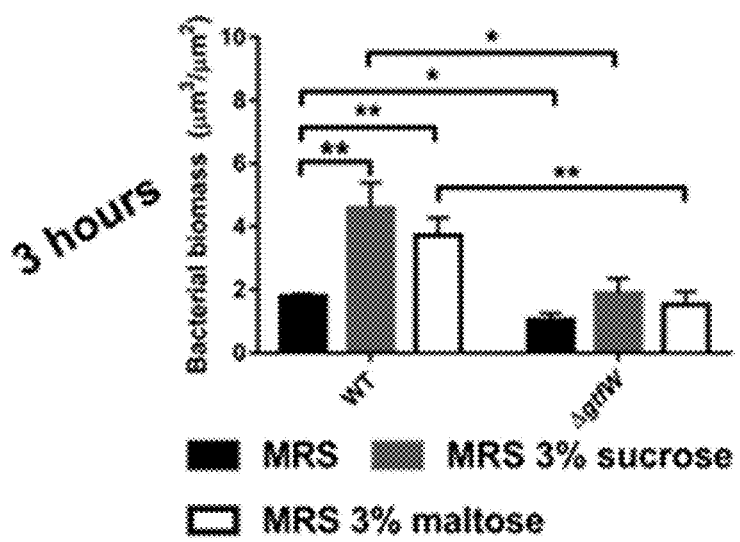
Figure 16D:
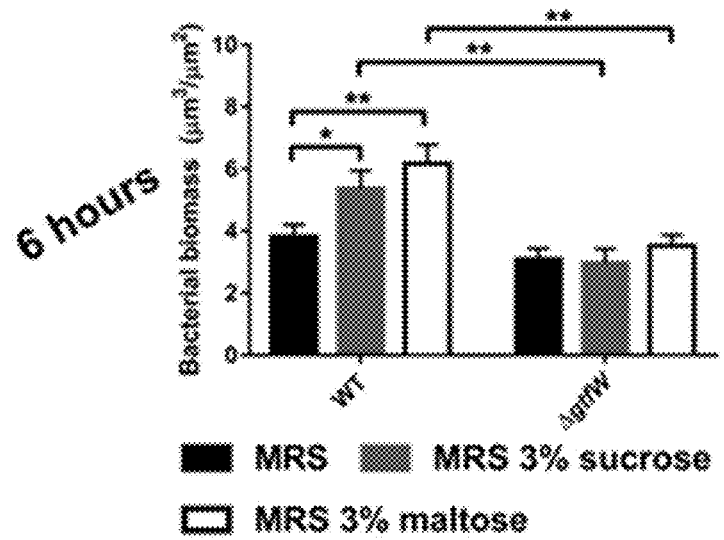

To determine if this GTFW-dependent binding is specific to the glycosyl linkages of DMs, *L. reuteri* binding to cellulose microspheres (CMs) were compared, as DMs are composed of polymers of glucose with α-linkages while CMs possess β-linkages between the glucose units (Updegraff, 1969; Kralj et al., 2002). As shown in FIG. 7A, only ~10% of *L. reuteri* adhered to CMs regardless of luminal contents. Collectively the data in FIGS. 7A-7C indicated that *L. reuteri* does not bind to CMs, binding to DMs was GTFW-dependent and further, that inclusion of maltose or sucrose significantly enhanced the binding of *L reuteri* to DMs. Applicants hypothesized that the predicted glucan binding domain of GTFW is a necessary component of *L. reuteri*'s ability to adhere to DMs. To further test if the adherence to DM is GTF-dependent, a mutant strain of *L. reuteri* (LMW500) was created with a chloramphenicol resistance gene inserted in place of the gtfW gene. As shown in FIG. 7B, the ΔgtfW strain was not able to bind to DMs as effectively as the wild type (WT) in the spin column assay, regardless of the cargo within the DM lumen. To further demonstrate the difference between the WT and ΔgtfW, Applicants examined biofilm formation on glass chamber slides in media supplemented with sucrose or maltose (FIGS. 16A-16D). After a 1 h incubation, the WT had more bacteria present and noticeably more bacterial aggregation when sucrose or maltose was added to the growth medium (FIGS. 16A & 16B). After 3 and 6 hours with sucrose or maltose supplemented media, the WT displayed a significantly more robust biofilm with greater biomass compared to the gtfW mutant under every condition, with significantly more cells present when sucrose or maltose was in the growth medium (FIGS. 16A, 16C & 16D).

Applicants next tested whether bacteria that do not express a similar GTF would lack the adherent phenotype shown in FIGS. 7A & 7B. To examine this, Applicants performed the disclosed DM adherence assay with another probiotic bacterium and three enteric pathogens that *L. reuteri* would likely encounter within the gastrointestinal tract: *Lactobacillus rhamnosus* GG, a Gram-positive bacterium commonly found in the genitourinary system and sold commercially as a probiotic; *Salmonella typhi*, a Gram-negative bacterium responsible for typhoid fever in humans; *Citrobacter rodentium*, a Gram-negative bacterium that causes colitis in rodents; and *Clostridium difficile*, a Gram-positive spore-forming bacterium that can cause severe colitis and recurring infections in humans. As shown in FIG. 7C, all of the non-GTF expressing bacteria showed minimal adherence to DMs, regardless of cargo present within the DM lumen.

Example 13.17: Diffusion of Cargo from DMs

Initial binding of bacteria to DMs is necessary for the microsphere compositions. However equally important is the ability to co-deliver beneficial luminal cargo needed by the adherent bacteria during transit of DMs through the gastrointestinal tract. Targeted delivery of maltose (or any other beneficial compound) via diffusion out of the DMs directly to the probiotic bacterium over time is a desired feature of this system. However, since the method of cargo delivery would be diffusion through the porous surface of the microsphere and not its degradation, such as occurs in poly(lactic-co-glycolic) acid (PLGA) microspheres (Danhier et al., 2012), the rate of diffusion is dependent upon the size of the microsphere, the mass of the solute, and the viscosity of the diluent.

Figure 8:
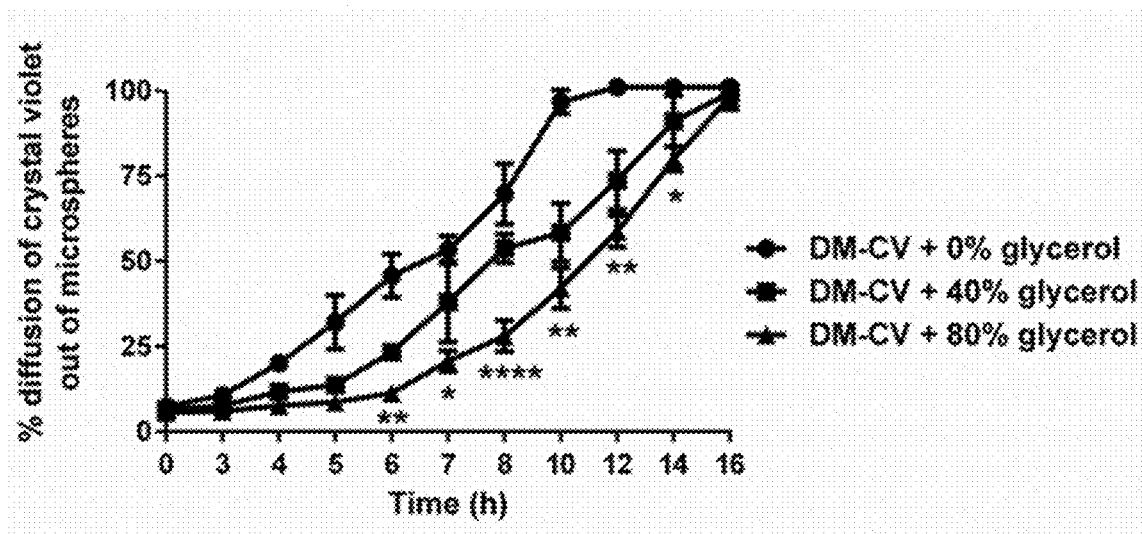
FIG. 8 Diffusion of cargo out of microspheres over time. Crystal violet (CV)-loaded DMs with and without glycerol (added to increase viscosity) were assayed to determine the relative rate of CV diffusion from the microspheres. With 0% added glycerol, CV diffused at a higher rate (100% diffusion after 10 hours) compared to DMs that contained 40% or 80% glycerol. Applicant observed 100% diffusion from DMs after 16 hours regardless of viscosity. Error bars represent standard error of the mean. Statistical significance from DMs with 0% added glycerol is indicated by the following: *$P<0.05$, $P<0.01$, **$P<0.0001$.

DMs were filled with crystal violet, a small molecular weight stain (407.979 g/mol), and the diffusion rate of the dye out of the DMs was tested with and without changing the viscosity of the solution in the DM lumen. As shown in FIG. 8, the crystal violet diffused out of the DM lumen with a half-life of ~6 hours. When the viscosity was increased by adding 40% glycerol, the half-life of release was increased to ~8 hours. At 80% glycerol, the half-life of crystal violet release was further enhanced to 12 hours. By 16 hours >95% of all of the crystal violet had been released under all tested conditions.

Example 13.18: *L. Reuteri* Produced Reuterin from Glycerol-Loaded Microspheres

Figure 17:
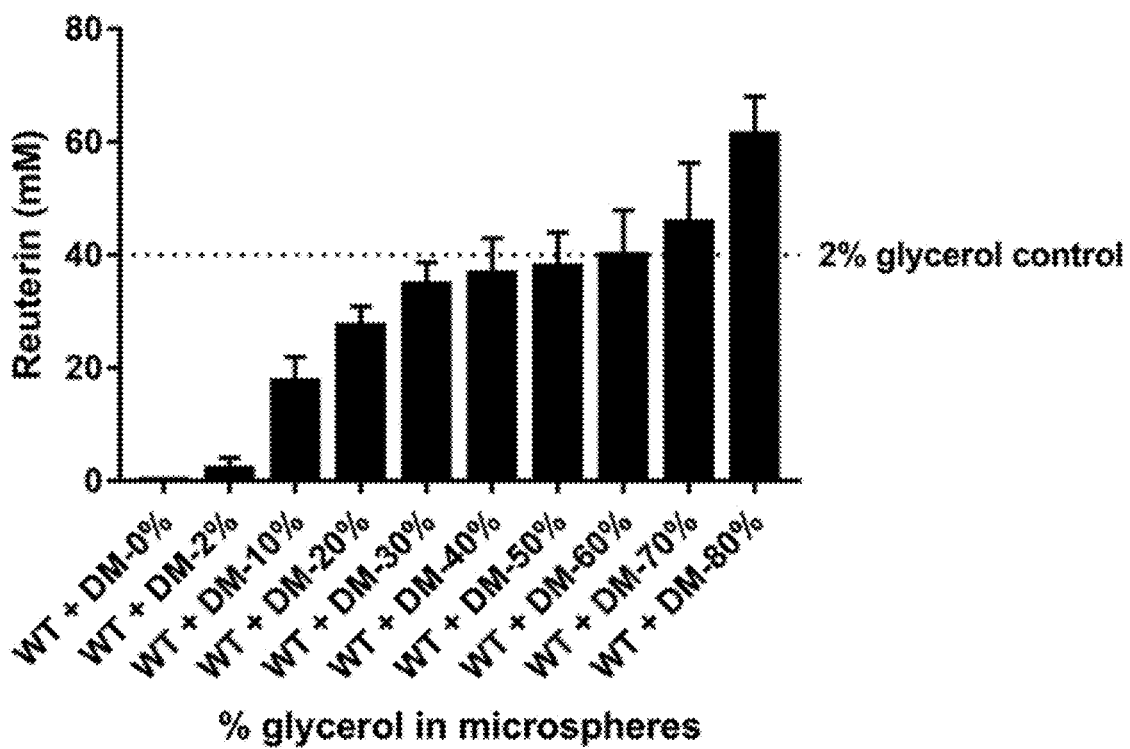
FIG. 17 shows that *L. reuteri* can produce reuterin from glycerol-loaded microspheres. *L. reuteri* incubated for 1 hour with DMs that contained 0-80% glycerol as the only source of glycerol in the experimental conditions were measured for relative reuterin production. For comparison, the amount of reuterin produced by *L. reuteri* without DMs in a 2% glycerol solution was used as a control (dotted line). Error bars represent standard error of the mean.
Figure 18:
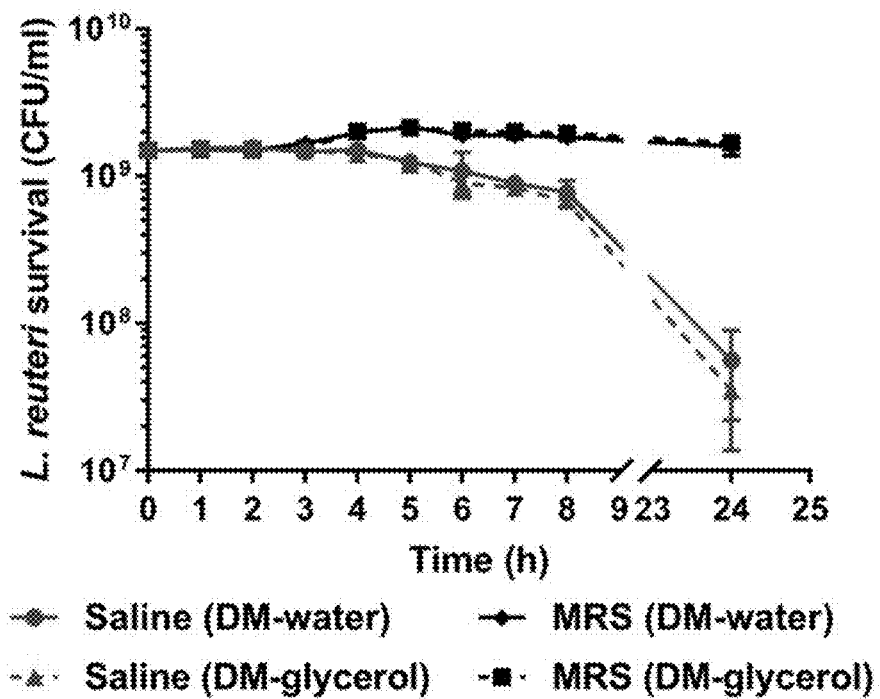
FIG. 18 show that glycerol delivered via DMs and any subsequently produced metabolites did not affect *L. reuteri* survival. Overnight cultures of WT *L. reuteri* were washed and resuspended in either saline or MRS medium. 5 mg of DM-water or DM-80% glycerol were then added to *L. reuteri* and incubated at 37° C. At hourly intervals the aliquots were taken for subsequent serial dilution and plating for viable CFU. After 24 hours there was no significant difference between cultures incubated in the same medium (saline or MRS) with either DM-water or DM-80% glycerol.
Figure 19:
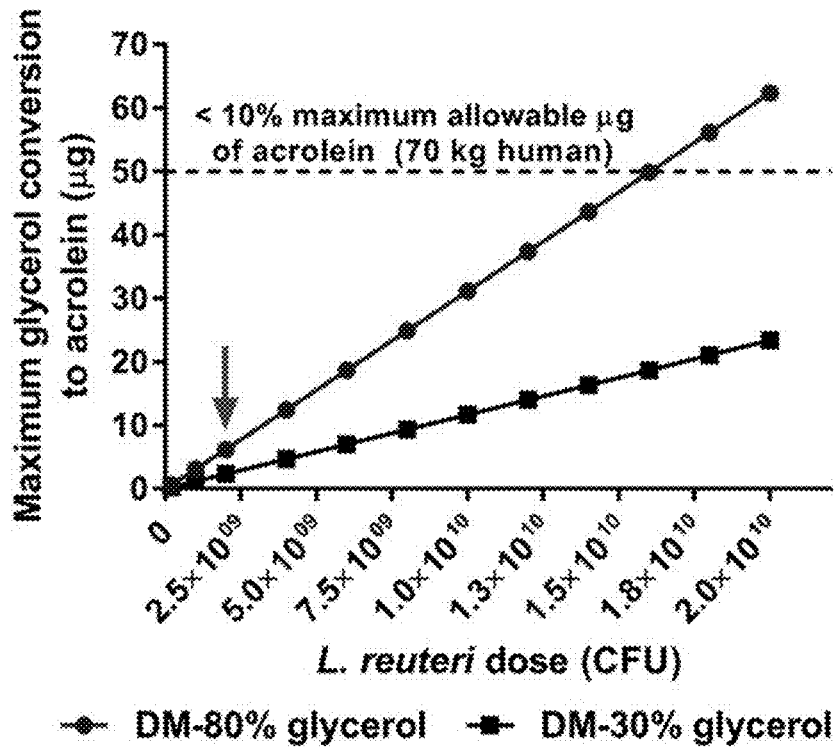
FIG. 19 illustrates maximum conversion of DM-provided glycerol to acrolein did not result in toxic levels of acrolein. The World Health Organization (WHO) recommends ingestion of no more than 7.5 µg/kg of body weight of acrolein per day. Assuming 100% conversion of available glycerol provided via DMs into acrolein by *L. reuteri*, the dosage of *L. reuteri* and DM-glycerol utilized in this work (red arrow) resulted in a maximum of 6.24 µg acrolein produced. The dashed line (50 µg acrolein) represents <10% of the daily allowable amount of acrolein for a 70 kg human.

An important feature of *L. reuteri*'s function as a probiotic bacterium is its ability to compete with pathogenic bacteria within the host potentially via production of antimicrobials e.g. extracellular reuterin (Cleusix et al., 2007; Spinler et al., 2008). Due to limited glycerol availability, suboptimal endogenous concentrations of glycerol in the GI tract would likely limit adequate reuterin production. In order to obviate the need to provide high levels of glycerol to satisfy *L. reuteri*'s optimal needs, Applicants provided targeted delivery of glycerol directly to the bacteria attached to the surface of DMs. To test this in vitro, a colorimetric assay for reuterin production (Cadieux et al., 2008) was utilized. As shown in FIG. 17, DMs filled with glycerol concentrations ranging from 10-80% were able to induce reuterin production. Compared to the 2% glycerol solution control, DMs filled with 80% glycerol produced on average 53% more reuterin in 1 hour (average concentration of reuterin produced: 2% glycerol=40 mM, DM-80% glycerol=61 mM). To determine if the 80% glycerol or the resulting reuterin/downstream metabolites of glycerol fermentation produced by *L. reuteri* is toxic to *L. reuteri*, Applicants compared hourly colony forming units (CFU) of *L. reuteri* incubated with either DM-water or DM-80% glycerol, in either sterile saline or MRS growth medium. As shown in FIG. 18, there was no loss of CFU regardless of DM cargo when *L. reuteri* was incubated in MRS. Incubating *L. reuteri* in saline did result in a steady loss of viable CFU over time, though there was no difference in viability between the DM-water and DM-80% glycerol over this time, suggesting the loss of CFU was not due to any potentially toxic compounds, such as reuterin or acrolein, from glycerol fermentation (FIG. 18). As acrolein in particular is known to be toxic to humans and is a byproduct of reuterin production, Applicants next calculated the maximum possible amount of acrolein that could be produced from the dosage of *L. reuteri* and volume of glycerol provided via DMs in the formulation, assuming all available glycerol was converted 1:1 into acrolein. As shown in FIG. 19, the amount of acrolein that could possibly be produced via this formulation is a nominal ~6 μg (for reference, the World Health Organization recommends less than 7.5 μg/kg body weight per day) (Gomes et al., 2002). From these results and the data presented in FIG. 8, Applicants suggest that DMs loaded with glycerol would have two beneficial effects in vivo, namely slowing the release of beneficial cargo and providing a substrate for reuterin production.

Figure 9:
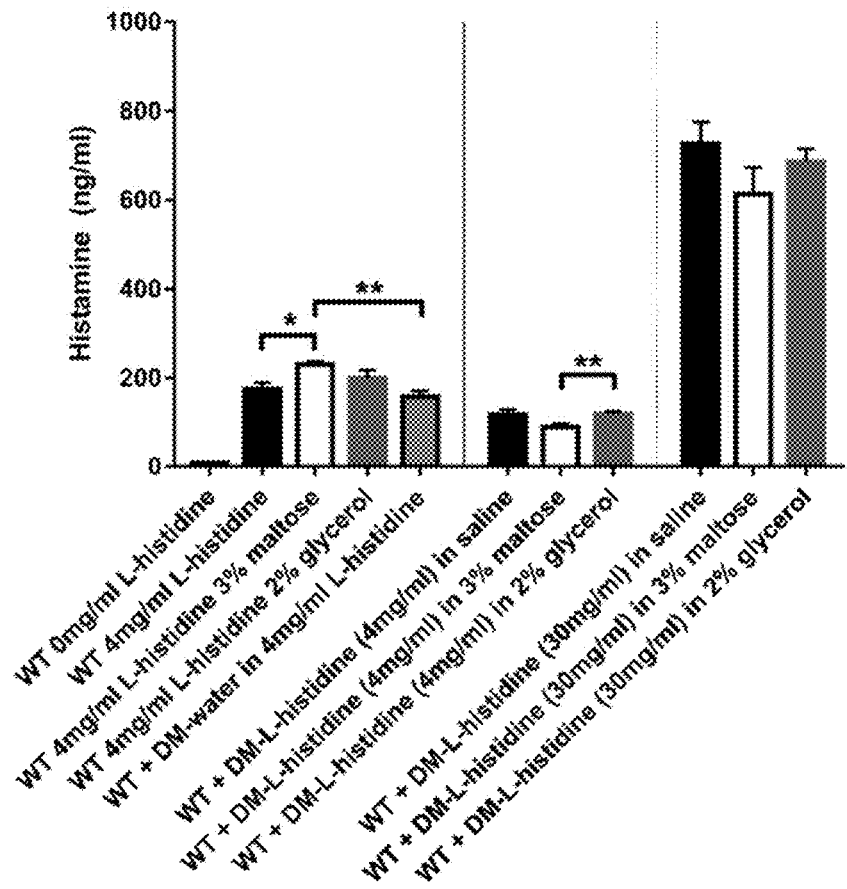
FIG. 9 shows that histamine can be produced by L. reuteri from L-histidine delivered via DM. Stationary phase WT L. reuteri was incubated for 2 hours in either saline with and without 3% maltose or 2% glycerol, or 4 mg/ml L-histidine with and without 3% maltose or 2% glycerol. Histamine production was increased with addition of 3% maltose to 4 mg/ml L-histidine solution (white bar black border) compared to just 4 mg/ml L-histidine (black bar and grey bar black border). When L-histidine at 4 mg/ml was provided via DM the overall levels of histamine produced were significantly lower (middle 3 bars) compared to L-histidine provided in solution (left 4 bars), likely due to less immediate availability of L-histidine to the bacteria. However, when the concentration of L-histidine loaded into DM was increased to 30 mg/ml, significantly more histamine was produced (right 3 bars) despite any caveats related to slower access to L-histidine due to availability only via diffusion out of DM. Error bars represent standard error of the mean. Statistical significance is indicated by the following: *$P<0.05$, **$P<0.01$.

Example 13.19: *L. Reuteri* Produced Histamine from L-Histadine-Loaded Microspheres Histamine produced by *L. reuteri* has previously been shown to inhibit pro-inflammatory cytokines such as TNF via $H_2$ receptors and reduce colitis in an animal model (Thomas et al., 2012; Gao et al., 2015). The microsphere formulations described herein provide a unique method for delivery of the histamine precursor substrate L-histidine to *L. reuteri*. To test this in vitro, DMs were filled with 30 mg/ml and 4 mg/ml L-histidine and measured the amount of histamine produced by the bacteria when the only source of L-histidine was via diffusion out of the DMs. As shown in FIG. 9, DM-L-histidine (4 mg/ml) resulted in histamine levels only slightly lower than those produced when bacteria were incubated in 4 mg/ml L-histidine solution without DMs. When the DMs were loaded with a higher concentration of L-histidine, the amount of histamine produced was 6-7 times greater than the lower 4 mg/ml concentration, consistent with the DM-L-histidine (30 mg/ml) providing ~7 times more L-histidine than the DM-L-histidine (4 mg/ml) (FIG. 9). In addition, whether other cargo relevant DM cargo substrates, such as maltose and glycerol, would negatively affect histamine production was also tested. Addition of glycerol did not result in reduced histamine production, regardless of whether the L-histidine was in solution or provided via DMs (FIG. 9). With addition of maltose, histamine production actually increased when L-histidine was provided in solution, but statistically unchanged when L-histidine was provided via DMs (FIG. 9).

Figure 10:
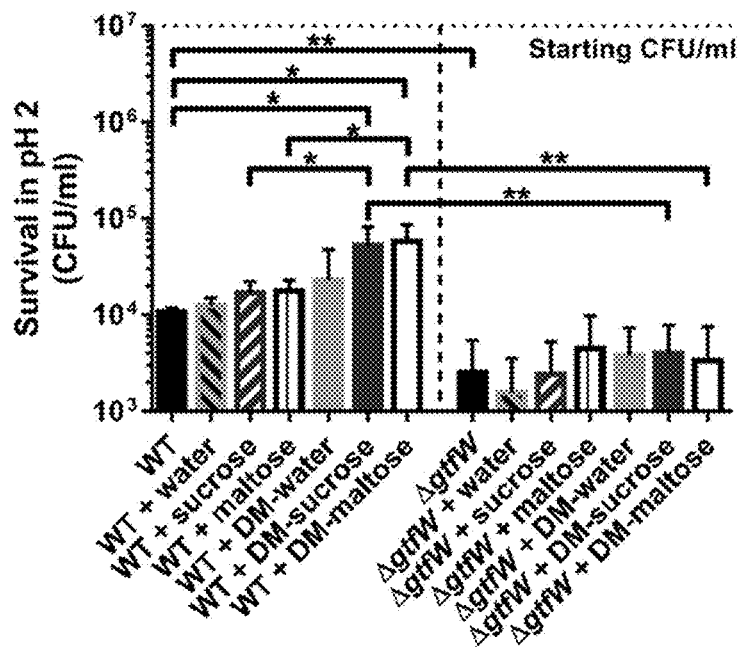
FIG. 10 shows gastric acid survival. WT and ΔgtfW L. reuteri ($10^7$ CFU/ml) viability after 4 hours in pH 2 synthetic gastric acid in the absence or presence of 5 mg of DMs that contained water, sucrose (1M), or maltose (1M) as cargo, or 10 μl of the cargo alone without DMs. Relative survival in acid was enhanced when WT L. reuteri was adhered as a biofilm on DMs that contained sucrose or maltose compared to equivalent volumes of the same cargo delivered without DMs, which indicated that the biofilm phenotype contributed to better survival during exposure to low pH. ΔgtfW showed decreased resistance to acid compared to the WT, regardless of the presence or absence of either DMs or sugar alone. Error bars represent standard error of the mean. Statistical significance is indicated by the following: *$P<0.05$, **$P<0.01$.

Example 13.20: Microspheres Filled with Sucrose or Maltose Improved *L. Reuteri* Survival at Low pH Orally consumed probiotics face a significant pH challenge upon reaching the stomach, where pH values are as low as 1.5 when the stomach is empty (Dressman et al., 1990). Enhancing the ability to deliver a maximal number of viable *L. reuteri* to the colon is crucial to its sustainability and effectiveness as a probiotic. *L. reuteri* bound to the surface of DMs in the form of a biofilm should increase survival upon exposure to acid, and that DMs filled with sucrose or maltose would result in even greater survival in a GTFW-dependent manner. As shown in FIG. 10, less than 0.1% of WT *L. reuteri* without DMs survived in synthetic gastric acid after 4 hours at pH 2, which resulted in a nearly 3 log loss of viable probiotic. Addition of water-filled DMs did not significantly alter the survival rate of WT *L. reuteri* in gastric acid; however, when either DM-sucrose or DM-maltose was delivered with WT, nearly 1 log more survived the acid stress (FIG. 10). To show that the protective effect is dependent on the microspheres and not the cargo within the DM lumen, *L. reuteri* was incubated with the equivalent amount of diffusible cargo without the DMs. Acid survival in the presence of cargo only was no different than *L. reuteri* alone (FIG. 10), which strongly indicated the importance of the bacterial biofilm-on-DM delivery system for the observed protective effect.

To investigate whether this phenotype is GTFW-dependent, synthetic gastric acid survival was tested using the ΔgtfW strain of *L. reuteri* and found that the beneficial effect of DM-sucrose and DM-maltose was lost (FIG. 10). Interestingly, the mutant also showed deficiency in acid survival without DMs compared to WT, which indicated that GTFW's role in cellular aggregation and biofilm formation (FIGS. 16A-16D) may contribute significantly to survival in synthetic gastric acid.

Figures 11A, 11B:
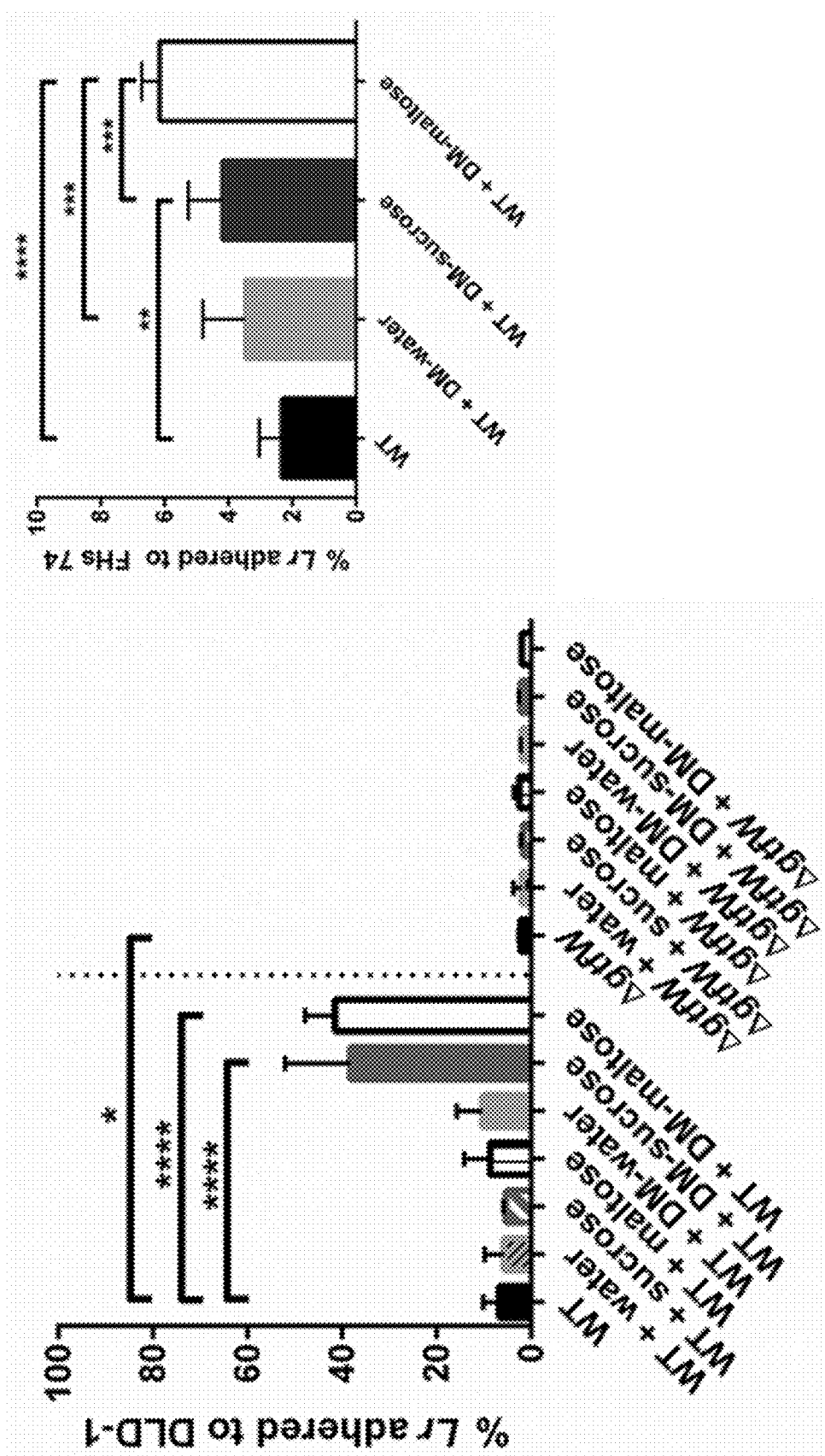
FIGS. 11A and 11B show that delivery of L. reuteri adhered to DMs as a biofilm supported increased adherence to intestinal epithelial cells.

Example 13.21: Microspheres Promote *L. Reuteri* Adherence to Human Intestinal Epithelial Cells This example investigated what effect the DMs, the DM luminal cargo and the product of the gtfW gene have on the relative adherence of *L. reuteri* when delivered as planktonic cells or as biofilms on DMs to the human intestinal cell lines DLD-1 (adult human colonic epithelial cells) and FHs 74 Int (3-4 months gestation, small intestine epithelial cells) in vitro. As shown in FIG. 11A, after a 1 h incubation on DLD-1 cells, significantly more WT *L. reuteri* (without DMs) adhered to the colonic cells compared to ΔgtfW either with or without DMs, which indicated that GTFW contributed to host cell adherence. When *L. reuteri* adhered to DMs that contained sucrose or maltose were added to colonic cells, relative adherence of WT *L. reuteri* to the colonic cells was increased by 4.7 fold for DMs that contained sucrose and by 5.2 fold for DMs that contained maltose (FIG. 11A). Although overall fewer WT *L. reuteri* adhered to the FHs 74 cells than to DLD-1 cells, delivering the bacteria with either DM-sucrose or DM-maltose resulted in 1.8 fold (DM-sucrose) or 2.7 fold (DM-maltose) more adhered bacteria compared to WT bacteria without DM (FIG. 11B).

Figure 12A:
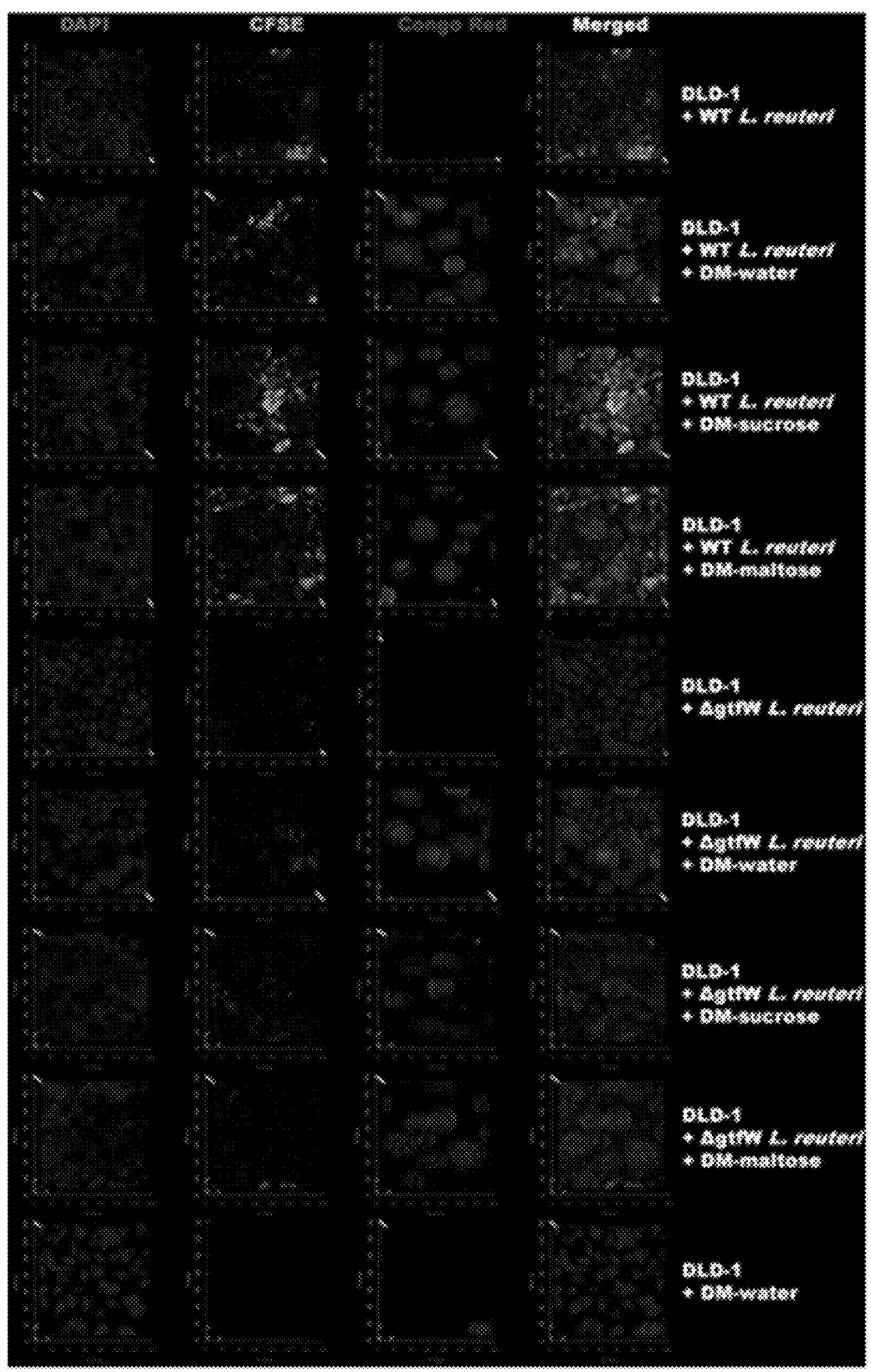
FIGS. 12A and 12B show that increased adherence to DLD-1 colonic epithelial cells is observed when L. reuteri was delivered as a biofilm attached to DMs.
Figure 12B:
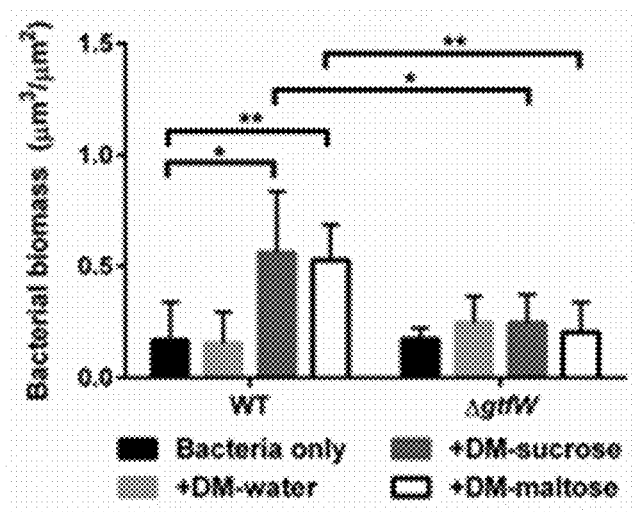

To further show that DM luminal cargo of maltose and sucrose improved relative adherence of *L. reuteri* to epithelial cells in vitro, we analyzed WT and ΔgtfW *L. reuteri* adherence after 1 hour incubation on DLD-1 cells visually, using CSLM (FIGS. 12A & 12B). As with the CFU data presented in FIGS. 11A & 11B, delivery of WT *L. reuteri* as a biofilm on maltose or sucrose-loaded DMs supported greater adherence to the DLD-1 cells than those delivered on water-loaded DMs or with no DMs, both by visual inspection (FIG. 12A) and when analyzed by quantification of bacterial biomass using COMSTAT analysis of CSLM images (FIG. 12B). The observed adherence was significantly diminished in the ΔgtfW mutant compared to the wild type, consistent with measured CFUs (FIG. 11A).

Figure 20:
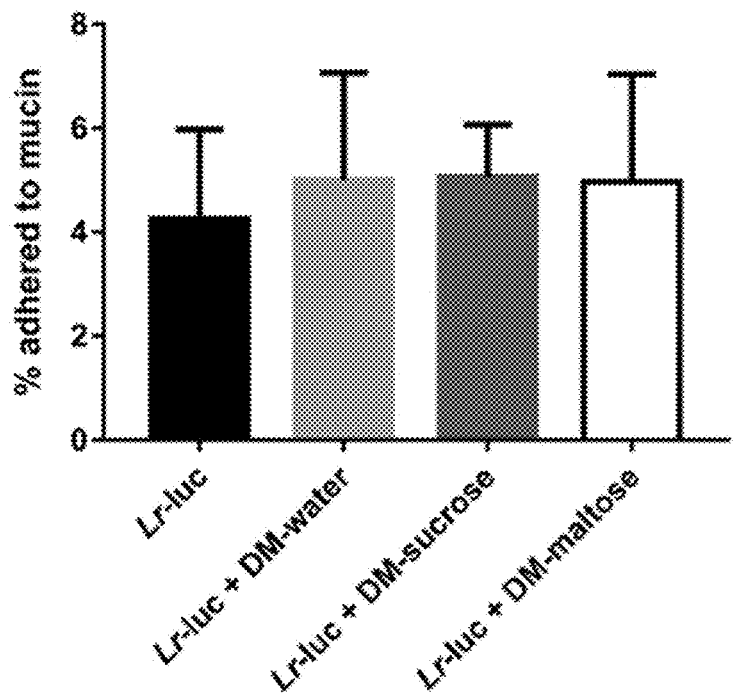
FIG. 20 shows that *L. reuteri* delivered as a biofilm on DMs does not inhibit adherence to mucin. *L. reuteri* reporter that expressed click beetle luciferase was dispensed either planktonically or as a biofilm on the DM surface onto agar plates that contained either 2% mucin+0.8% agar or 0.8% agar, incubated at room temperature for 1 hour, then washed to remove non-adhered *L. reuteri*. D-luciferin (0.4 mM) was then added to the plates, and the plates were imaged for luminescent signal that originated from remaining adhered bacteria. To calculate the amount of bacteria adhered to only mucin, the relative luminosity of the agar-only plates was subtracted from the relative luminosity of the mucin+agar plates.
Figure 21A:
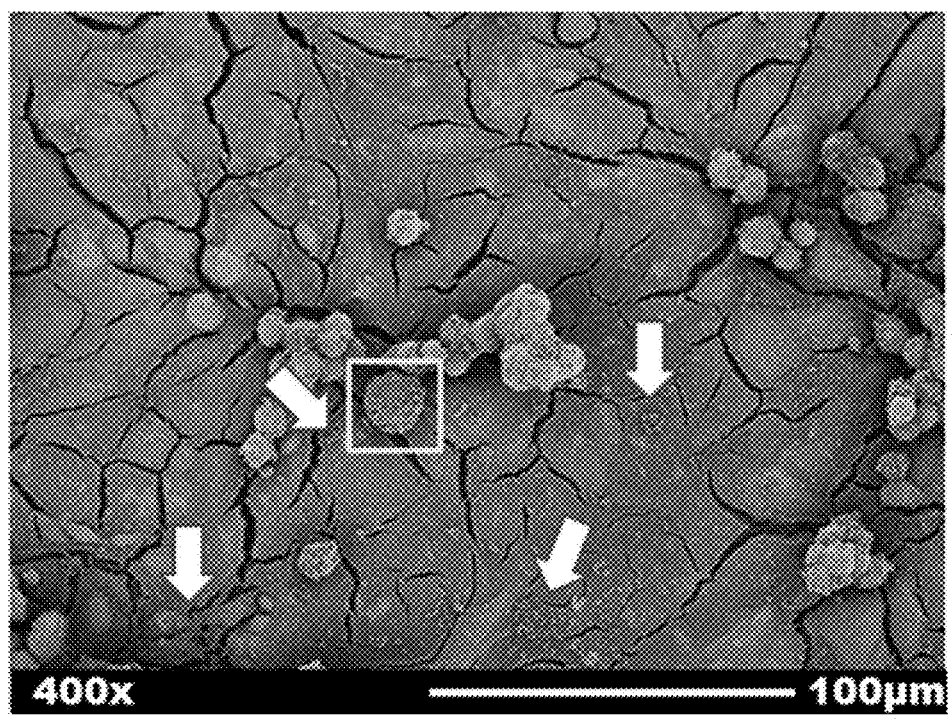
FIGS. 21A and 21B show that *L. reuteri* adhered to DMs and *L. reuteri* attached to the surface of DLD-1 human colonic epithelial cells. In vitro SEM of *L. reuteri* and DMs on a confluent monolayer of DLD-1 cells. Bacteria and DMs were incubated for 1 hour on DLD-1 epithelial cells, washed three times, fixed and prepared for SEM analysis. 400× (FIG. 21A) and 2500× (FIG. 21B) magnification showed *L. reuteri* adhered to a DM (yellow box) and several clusters of *L. reuteri* without DMs (white arrows) adhered to the surface of DLD-1.
Figure 21B:
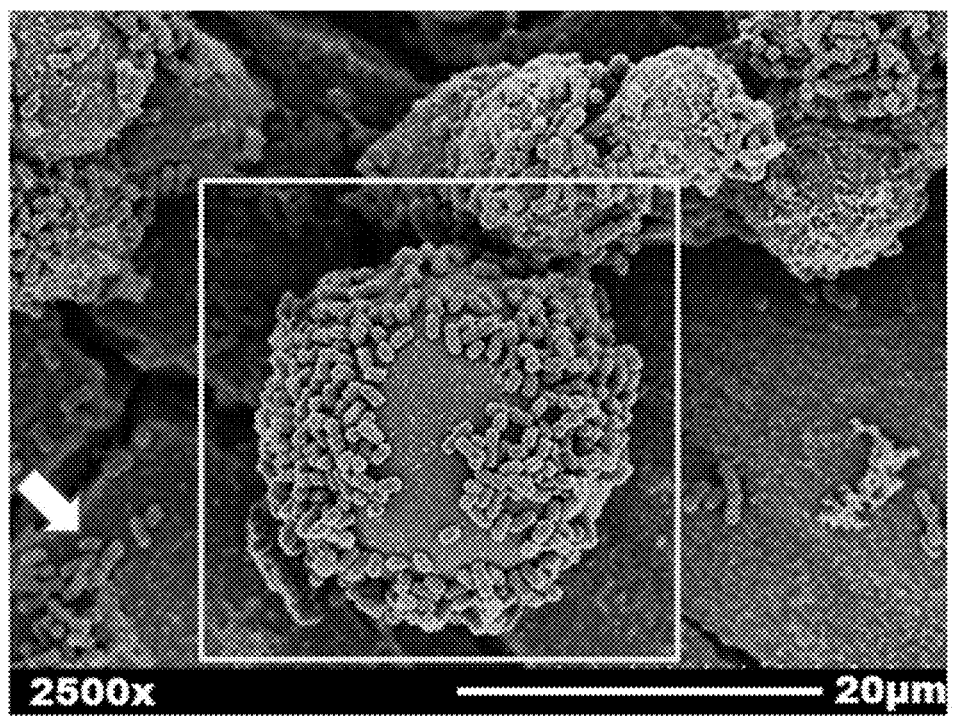

Finally, the effect of DM adhered WT *L. reuteri*'s ability to bind to mucin was tested. While cellular binding of probiotics likely plays a role in colonization, a healthy GI tract has a mucus layer on the apical surface of epithelial cells, of which the primary constituent is mucin (Turner, 2009). Indeed it is believed that healthy commensals are found primarily within this layer so it is preferred that the formulation maintains it enhanced probiotic effects in the presence of mucin. As mucin adherence is not GTF-dependent, but rather controlled by specific mucin-binding proteins (Miyoshi et al., 2006; Lukic et al., 2012), it was anticipated that being bound to DMs would not have an effect on the ability of *L. reuteri* to adhere to mucin. As shown in FIG. 20, there is no significant difference in relative adherence of WT *L. reuteri* to mucin when delivered as either a planktonic bacterial suspension or as a biofilm adhered to DMs after a 60 min incubation on mucin agar plates.

Example 13.22: Discussion

It has been shown that a single dose of *L. reuteri* delivered as a biofilm adhered to DMs reduces the incidence of necrotizing enterocolitis (NEC) by 50% (Olson et al., 2016) in a rat pup model. Example 13 shows that *L. reuteri* bound to DMs with appropriate luminal cargo promoted significantly increased survival at low pH and supported increased adherence to human epithelial cells in vitro. Importantly *L. reuteri* and DMs are considered "generally recognized as safe" (Grasser et al.) by the FDA. In fact, DMs have been used in medical products that are left in the body for long periods of time (years) with no ill effects (Roy, 2012), such as with Debrisan®, a cicatrizant wound dressing (Jacobsson et al., 1976), Deflux®, a bulking gel used to treat vesicoureteral reflux (VUR) in children (Stenberg and Lackgren, 1995), and Solesta™, a bulking gel injected submucosaly into the anal canal to treat fecal incontinence (Hoy, 2012). The results described herein show a small subset of possible beneficial cargos that can be placed into the DM lumen for utilization by *L. reuteri*, and for many applications one can match the lumen cargo precursor to the desired *L. reuteri*-produced effect (e.g. reuterin and histamine. Moreover, this formulation obviates recombinant versions of probiotics, an approach not currently approved by the FDA (Venugopalan et al., 2010).

Figure 22A:
FIGS. 22A and 22B show incidence and severity of NEC.
Figure 22B:
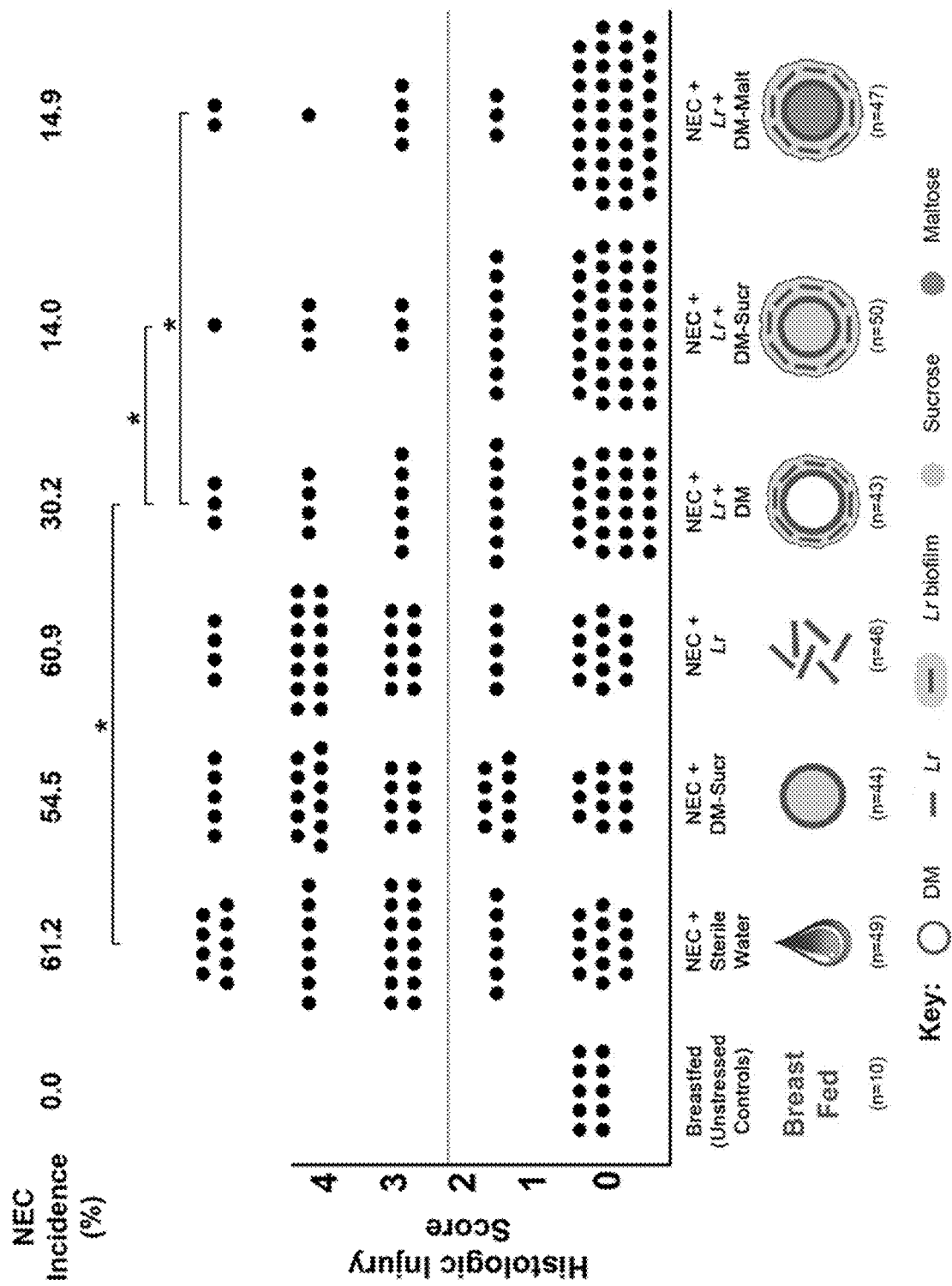

An exciting feature of our novel formulation is the ability to directly deliver beneficial compounds to the probiotic bacteria that are adhered to the DM surface as a biofilm (FIG. 22B). To combine beneficial compounds (prebiotics) with beneficial bacteria to stimulate growth is a well-established concept in probiotic research and commercial applications (Collins and Gibson, 1999; de Vrese and Schrezenmeir, 2008). There is significant evidence to show that synergism between probiotics and prebiotics effectively increases the overall population of probiotic bacteria (de Vrese and Schrezenmeir, 2008; van Zanten et al., 2014) and promotes effective treatments of diseases such as inflammatory bowel disease (Geier et al., 2007) and necrotizing enterocolitis (Asmerom et al., 2015). However a major drawback of traditional prebiotics is that they are typically limited to carbohydrates that are non-digestible or absorbable by the host to ensure sufficient availability to the probiotic bacteria in the gut. The disclosed compositions effectively solve this problem in that the probiotic bacterium *L. reuteri* is now delivered: (1) in association with DMs to which it adheres in greater numbers; (2) in the form of a biofilm which confers resistance to clearance; (3) along with a cargo of nutrients that promotes bacterial growth; (4) with cargos that promote production of the antimicrobial reuterin or histamine; (5) in a format that is resistant to acid-mediated killing thus promoting improved survival during transit through the acidic stomach and (6) in a manner that appeared to better support adherence to intestinal epithelial cells and thus likely to promote persistence in the gut. With regard to *L. reuteri*-induced release of substance potentially beneficial to the host, reuterin has been suggested to inhibit competition by other gut flora, and histamine has been shown to have anti-inflammatory effects. Although the secondary metabolites produced from glycerol metabolism to generate reuterin (e.g. acrolein) and histamine could result in adverse effects at high levels, the maximum quantities generated with our formulations are <1% and <40% less than what is thought to be problematic in humans for acrolein (FIG. 19) and histamine, respectively (Maintz and Novak, 2007; Thomas et al., 2012; Engels et al., 2016).

Using maltose as cargo have particular value for several reasons; it is the substrate for this strain of *L. reuteri*'s glucosyltransferase (GTFW) (Leemhuis et al., 2013; Bai et al., 2015), induces *L. reuteri* to aggregate in a GTF-dependent manner (Walter et al., 2008), and causes *L. reuteri* to grow significantly faster and to a higher cell density (CFU/ml). In this experiment it is shown that both maltose and sucrose have a positive effect on *L. reuteri* adherence to microspheres, promote adherence of *L. reuteri* to human intestinal epithelial cells, and improves bacterial survival in gastric acid (FIGS. 6A-6C, 7A-7C, 11A & 11B, 12A & 12B, & 13). *S. mutans* and *L. reuteri* GTF proteins are very similar in sequence and structure. Sucrose is the sole substrate for *S. mutans* and most *L. reuteri* GTF proteins (Tieking et al., 2005; Walter et al., 2008), and sucrose has previously been shown to cause *L. reuteri* cultures to aggregate rapidly in a GTF-dependent manner (Walter et al., 2008). The positive effect of sucrose to induce GTFW dependent adhesion is likely due to GTFW acting as an adhesin to DMs (via the glucan binding domain) and sucrose's ability to induce gtfW expression (FIG. 15A). Indeed, failure of sucrose to affect *L. reuteri* adherence to CMs (cross-linked glucan with variant glycosidic linkages)

supports this notion. Sucrose-dependent biofilm formation has previously been linked to two-component regulatory systems in the rodent strain 100-23 of *L. reuteri* (Frese et al., 2011; Su and Ganzle, 2014); however, the genes necessary for this phenomenon appear to be absent in the human-derived strain of *L. reuteri* used in this study (23272/DSM 20016). Since sucrose is a preferred carbon source of the *L. reuteri* used in this study via its sucrose phophorylase mediated metabolism (Ganzle and Follador, 2012) it was not surprising that sucrose had a positive impact on biofilm formation and increased adherence to DMs and is likely due to the increased doubling time of *L. reuteri* in the presence of sucrose. The failure of glucose (a carbon source but not a gtfW inducer or GTFW substrate) and fructose [an inducer of gtfW, but not a carbon source (FIGS. 15A & 15B), or substrate for GTFW] to enhance adherence to DMs suggests that understanding bacterial physiology will be critical in selecting beneficial luminal cargos.

Many parameters important to *L. reuteri*'s survivability and sustainability within the host can be improved by delivering *L. reuteri* as a biofilm on the surface of DMs that contain beneficial cargo. With more viable bacteria available after low pH challenge and supporting increased adherence to intestinal epithelial cells, the resulting expansion of probiotic bacteria available within the host should have an increased potentially beneficial effect. Further, targeted nutrients and substrates can be directly delivered to the bacteria adhered on the DM surface, which has broad-reaching implications for the type of compounds that can be co-delivered with orally consumed *L. reuteri*, which to date have been limited to carbohydrates that are indigestible by the host.

Example 14: Protection from Necrotizing Enterocolits in Rats

To determine NEC incidence and survival, rat pups were delivered prematurely, given a single enteral Lr treatment, and subjected to experimental NEC (hypercaloric feeds/hypoxia/hypothermia). Pups were sacrificed 96 h post-delivery or when clinical NEC developed. Tissue was harvested for histologic evaluation and measurement of inflammatory markers. Intestinal mucosal barrier integrity was assessed by serum levels of enterally-administered FITC-dextran. A bioluminescent strain of Lr was constructed to assess persistence in the GI tract. A GtfW-deficient strain of Lr was developed to assess the role of biofilm formation. Lr adhered to sucrose- or maltose-loaded DM significantly reduced experimental NEC compared to Lr adhered to unloaded DM. Lr adhered to sucrose- or maltose-loaded DM improved survival, decreased intestinal permeability, and reduced intestinal inflammation.

Neonatal Rat Model of Experimental NEC. All animal studies were conducted in compliance with protocol #AR15-00012 approved by the IACUC of The Research Institute at Nationwide Children's Hospital. Sprague-Dawley rat pups at 20.5 days gestational age were delivered from timed-pregnant dams (Envigo, Indianapolis, Ind.) via cesarean section under $CO_2$ anesthesia. Immediately after delivery, pups were randomized into experimental groups that received a single enteral Lr or control treatment via gastric gavage. Pups were then subjected to our well-established model of experimental NEC (Dressman et al., 1990; Freire et al., 2016) which is a modification of a stress protocol to induce NEC first introduced by Barlow et al. in 1974 (Freire et al., 2011; Frese et al., 2011). In short, pups were subjected to repeated episodes of: 1) hypertonic, hypercaloric formula feeds via orogastric gavage five times daily with 15 g Similac 60/40 (Abbott Nutrition, Columbus, Ohio) in 75 mL of Esbilac (Pet-Ag, New Hampshire, Ill.), providing a combined 836.8 kJ/kg/day; 2) three episodes of hypoxia and hypothermia each day (placement in a chamber of $N_2$ gas calibrated to $FiO_2$<1.5% for 90 seconds directly followed by placement in a 4° C. environment for 10 min); and 3) gastric gavage of 2 mg/kg lipopolysaccharide (LPS, Sigma-Aldrich, St. Louis, Mo.) on the first day of life. Between each of these episodes, pups were housed in an incubator at 35° C. Breastfed control pups were placed with a surrogate dam immediately after cesarean delivery and were not exposed to experimental stress.

Lr Biofilm Preparation and Administration. Human feces-derived *Lactobacillus reuteri* 23272 was purchased from American Type Culture Collection (ATCC, Manassas, Va.) and grown in de Man, Rogosa, and Sharpe (MRS) broth (Fisher Scientific, Pittsburg, Pa.)[35] overnight at 37° C. under 5% $CO_2$. For planktonic Lr administration, Lr was pelleted and resuspended in sterile 0.9% saline and administered via gastric gavage to neonatal pups at a dose of $2 \times 10^8$ CFU/pup (a dose consistent with other published studies) (Gao et al, 2015). For Lr administered in its biofilm state, Lr was introduced to DM prior to administration as described previously (Eaton et al., 2011). In short, sterile, dry DM (Sephadex G-25 Superfine, GE Healthcare Bio-Sciences, Pittsburgh, Pa.) were hydrated in water at 50 mg/mL and then autoclaved for 20 min. For treatment groups that contained sucrose or maltose, DM were removed from solution and collected into 1 mL of sterile 1 M solution of the sugar. The solution was vortexed and incubated at RT for 24 h. DM were then removed from the solution using a vacuum filter and aseptically scraped with a sterile loop into a tube containing resuspended bacteria. Lr was allowed to incubate with DM for 30 min at RT to facilitate binding and biofilm formation. Pups were then gavaged with 100 µL of the bacterial-DM solution resulting in a final dose of $2 \times 10^8$ CFU/pup.

Incidence and Severity of Experimental NEC. Immediately after delivery pups were randomly divided into 1 of 7 experimental groups that received one of the following treatments via gastric gavage: 1) 100 µL sterile water (vehicle control) (n=49); 2) DM-Sucr (n=44); 3) $2 \times 10^8$ CFU Lr (n=46); 4) $2 \times 10^8$ CFU Lr+DM (n=43); 5) $2 \times 10^8$ CFU Lr+DM-Sucr (n=50); or 6) $2 \times 10^8$ CFU Lr+DM-Malt (n=47). An additional group of pups were returned to surrogate dams and served as breastfed unstressed controls. After receiving their single treatment dose, pups were subjected to the experimental NEC protocol previously described. When signs of NEC developed (bloody stools, severe abdominal distention, lethargy, respiratory distress, cyanosis) pups were sacrificed. All remaining pups were sacrificed 96 h after delivery. Upon sacrifice, intestinal tissue was harvested and fixed in 10% formalin for 24 h. Fixed tissue was paraffin-embedded and then hematoxylin and eosin (H&E)-stained transverse sections were prepared. Two independent observers graded each section in a blinded fashion using an established histologic injury grading scale initially established by Caplan et al. (Dressman et al., 1990; Freire et al., 2016; Geier et al., 2007) Histologic injury was classified as: grade 0, no visible histological villus damage; grade 1, distal villus enterocyte detachment; grade 2, sloughing of enterocytes to the mid-villus level; grade 3, loss of entire villus with preservation of the crypts; and grade 4, transmural necrosis (FIG. 22A). Experimental NEC was defined as an injury score of grade 2 or higher.

Intestinal permeability. Immediately after delivery pups were randomized to receive one of the following: 1) 100 μL sterile water (vehicle control) (n=20); 2) 2×10⁸ CFU Lr (n=20); 3) 2×10⁸ CFU Lr+DM-Sucr (18); or 4) 2×10⁸ CFU Lr+DM-Malt (n=15). An additional group of pups were returned to surrogate dams and served as breastfed unstressed controls. Pups were then subjected to the experimental NEC protocol for 48 h, at which time each received 1500 mg/kg of fluorescein isothiocyanate (FITC) labeled dextran (FD70, molecular weight 70,000) (Sigma-Aldrich Inc., St. Louis, Mo.) suspended in sterile PBS via orogastric gavage. Pups were sacrificed 4 h later and serum collected into BD Microtainer SST tubes (Becton, Dickinson and Company, Franklin Lakes, N.J.). Serum was extracted and fluorescence measured with a fluorescent plate reader (SpectraMax M2, Molecular Devices, Sunnyvale, Calif.) using a 492/518 nm filter set. The plasma concentration of FD70 for each pup was then extrapolated using a standard curve generated from a 1:2 serial dilution of a known FD70 concentration.

Following cesarean delivery, pups were randomly divided to receive one of two enteral treatments: 1) 2×10⁸ CFU Lr-Luc (n=6); or 2) 2×10⁸ CFU Lr-Luc+DM-Sucr (n=6). Pups were then subjected to experimental NEC. After 48 h all pups were sacrificed and their GI tract harvested. The contents of the small intestine and cecum/colon were separated and homogenized by bead-beating with 0.7 mm beads for 2.5 min. 2 mM D-luciferin (luciferase substrate) was added to each tissue homogenate and bioluminescence was measured using a Xenogen IVIS Spectrum imaging system (PerkinElmer, Inc, Waltham, Mass.).

Statistical analyses. All data are expressed as the mean±SEM. One-way analysis of variance, followed by pairwise comparison was performed with GraphPad Prism 7 (La Jolla, Calif.) and SAS 9.4 software (SAS Institute, Inc., Cary, N.C.). For animal survival, a Log-rank test was performed. For RNA expression, IQR method was used to identify outliners. Statistical significance was defined as $p \leq 0.05$.

Results

Effect of Lr biofilm formation on NEC incidence and severity. Nearly two thirds of untreated pups subjected to the experimental protocol developed NEC (FIG. 22B). The incidence of NEC was statistically unchanged for pups that received DM-Sucr alone (p=0.343) or planktonic Lr alone (p=0.334). In contrast, compared to untreated pups, pups that received Lr+DM had a significant reduction in NEC incidence (p<0.001). Finally, a single dose of Lr+DM-Sucr or Lr-DM-Malt resulted in a further decrease in NEC incidence to 14% (p<0.001) and 15% (p<0.001), respectively. Importantly, compared to Lr+DM, both Lr+DM-Sucr and Lr+DM-Malt resulted in a significant reduction in NEC severity (p=0.045 and p=0.022, respectively). No breast fed pups developed NEC.

Figure 23:
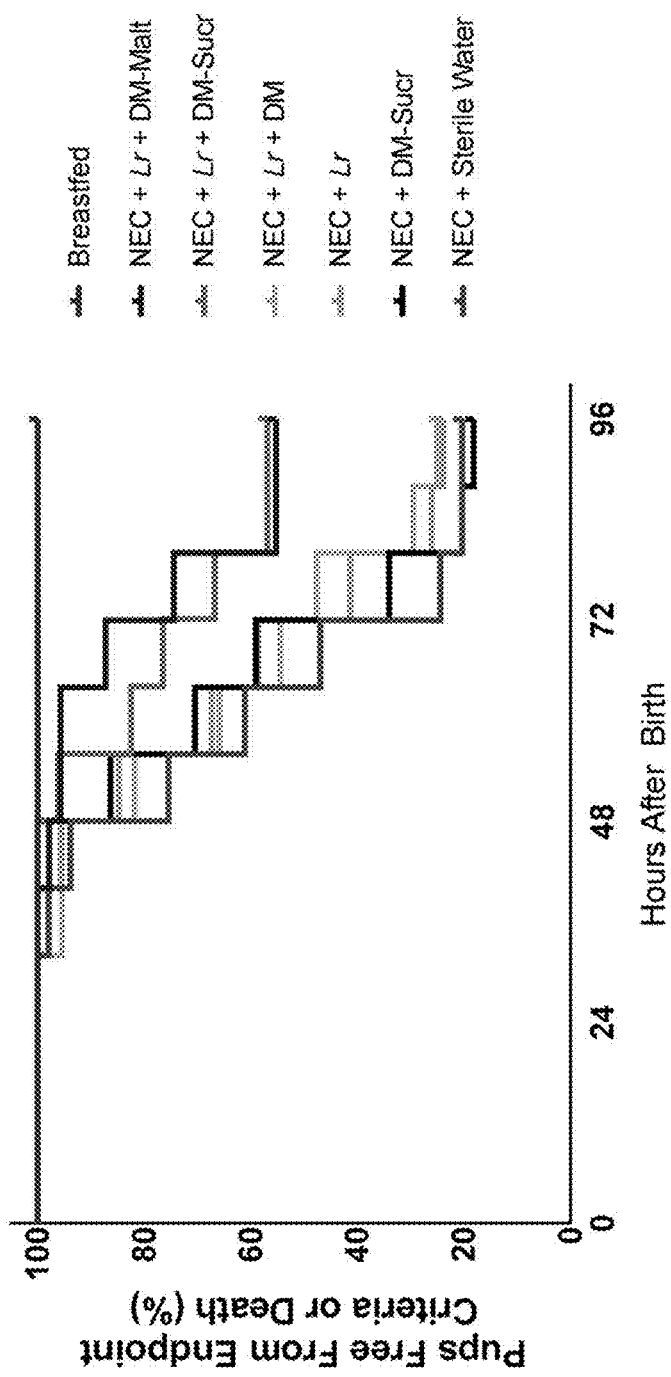
FIG. 23 shows rat pup survival. The number of pups alive and free from endpoint criteria (lethargy, bloody stools, agonal breathing, cyanosis) are depicted for each experimental group in 8 h intervals over the course of the 96 h experimental NEC protocol.

Effect of Lr biofilm formation on survival. All breastfed pups survived the entire 96 h protocol (FIG. 23). In contrast, only 20.4% of untreated pups subjected to the protocol were alive and free from endpoint criteria (lethargy, bloody stools, agonal breathing, cyanosis) after 96 h. Pups treated with DM-Sucr (18.2%), Lr (23.9%), or Lr+DM (25.6%) had no improvement in survival. However, pups that were treated with a single dose of either Lr+DM-Sucr or Lr+DM-Malt had significantly improved survival compared to untreated pups. Pups treated with Lr+DM-Sucr had 58.0% survival (hazard ratio of 2.62 with 95% CI 1.57-4.37), while pups treated with Lr+DM-Malt had 55.3% survival (hazard ratio of 2.88 with 95% CI of 1.72-4.84).

Figure 24:
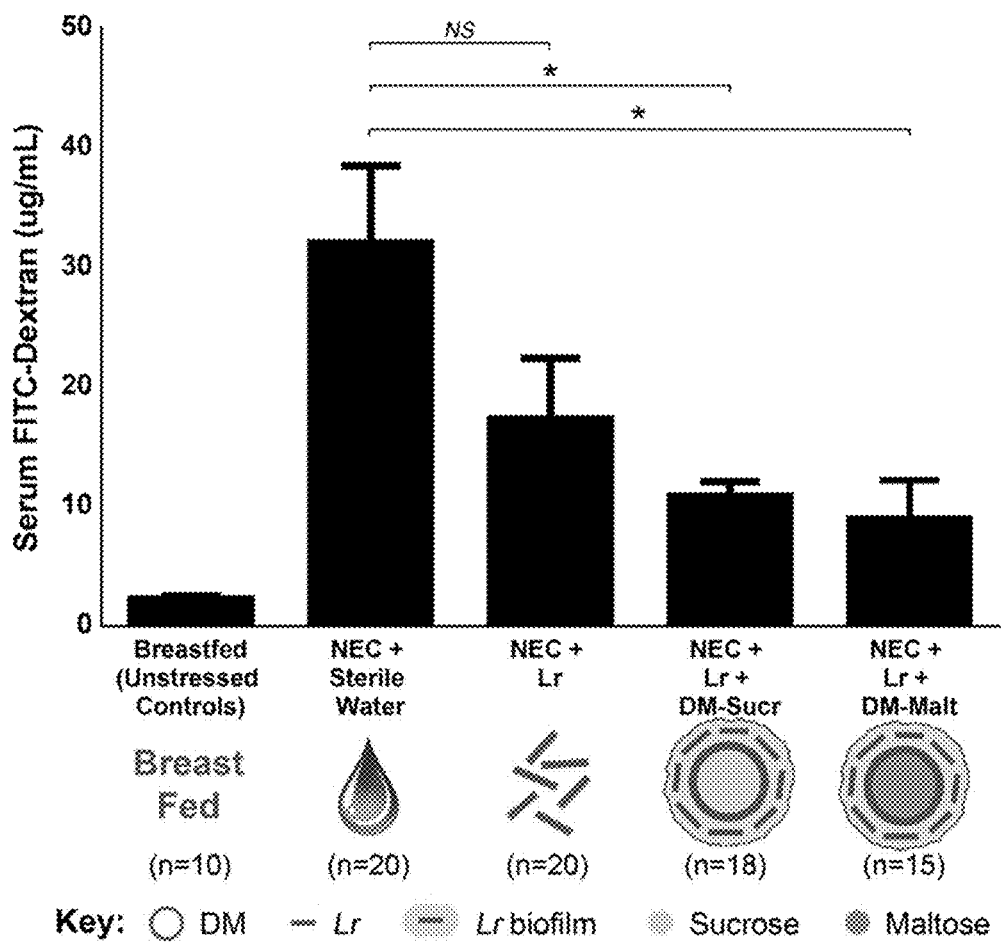
FIG. 24 shows intestinal permeability of rat pups subjected to experimental NEC. Intestinal permeability was determined by measuring serum levels of FITC dextran 4 h after gastric administration of FITC dextran, with greater levels of serum FITC dextran indicating greater intestinal permeability. FITC, fluorescein isothiocyanate. *p<0.05.

Effect of Lr biofilm formation on intestinal mucosal permeability. After 48 h of the experimental NEC protocol, untreated pups had significantly increased intestinal permeability compared to breastfed control pups, as demonstrated by significantly higher serum levels of FD-70 4 h after enteral FD-70 administration (31.99±6.5 μg/mL vs. 2.22±0.3 μg/mL; p=0.003) (FIG. 24). Although pups treated with planktonic Lr alone had some decrease in serum FD-70 (17.32±5.0 μg/mL; p=0.083), pups treated with a single dose of Lr+DM-Sucr or Lr+DM-Malt had a significant reduction in serum FD-70 (10.83±1.2 μg/mL; p=0.004, and 8.98±3.2 μg/mL; p=0.007).

Figure 25:
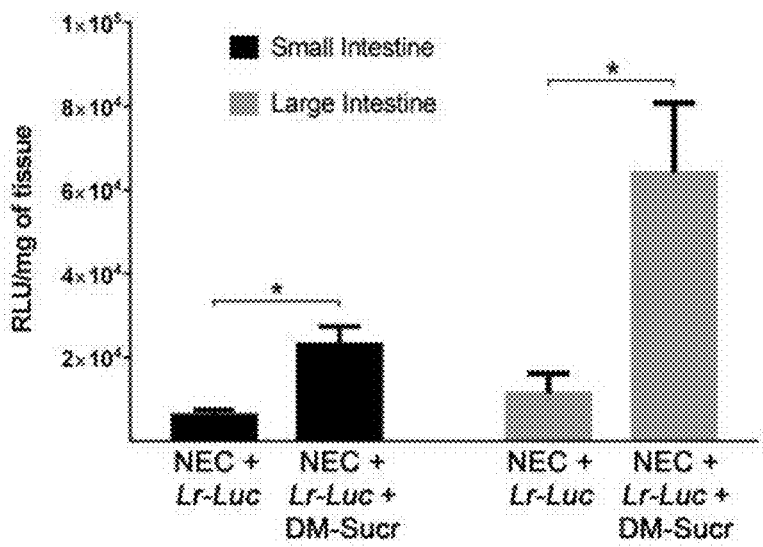
FIG. 25 shows Lr Persistence in the GI tract. A bioluminescent strain of Lr was generated and used to track Lr presence in the small and large intestine (as the amount of light emitted) after 48 h of the experimental NEC protocol. RLU, relative light units. *p<0.05.
Figure 26A:
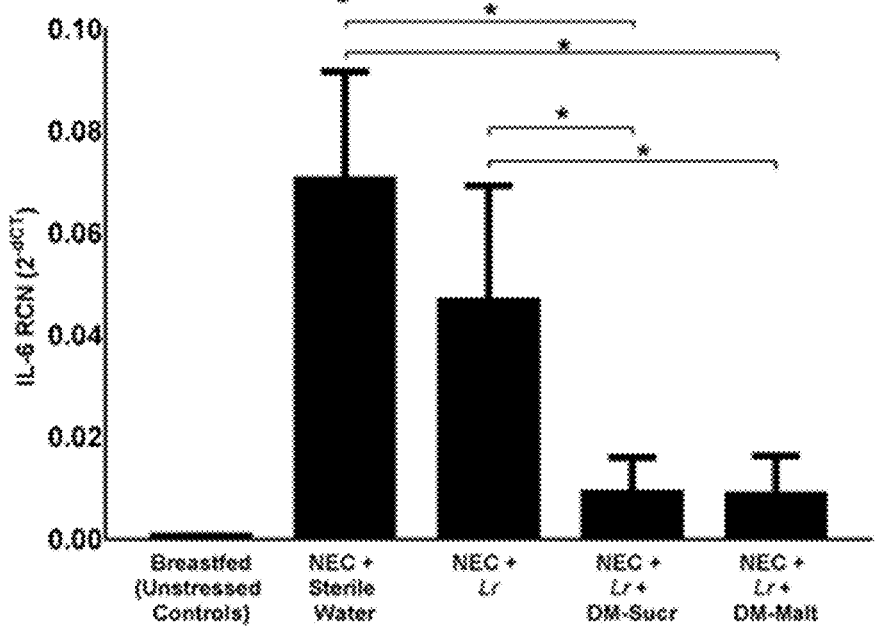
FIGS. 26A-26E show inflammatory markers. Intestinal specimens were collected and fixed in formalin. RNA was isolated and analyzed with real-time qPCR for the expression of (FIG. 26A) IL-6, (FIG. 26B) IL-1β, (FIG. 26C) CCL-2, (FIG. 26D) CXCL-1, and (FIG. 26E) IL-10. Results represent the mean±SEM of 7-10 different rat pups, performed in duplicate. *p<0.05.
Figure 26B:
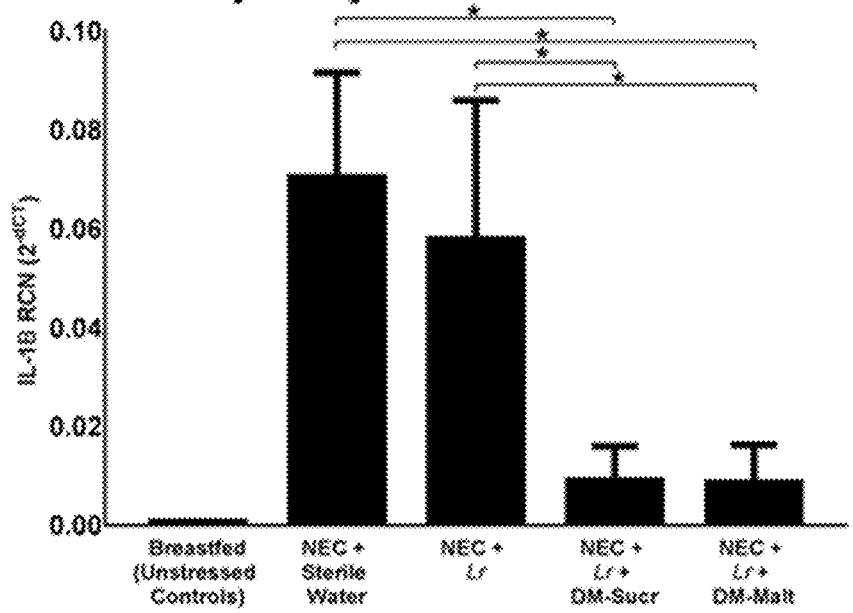
Figure 26C:
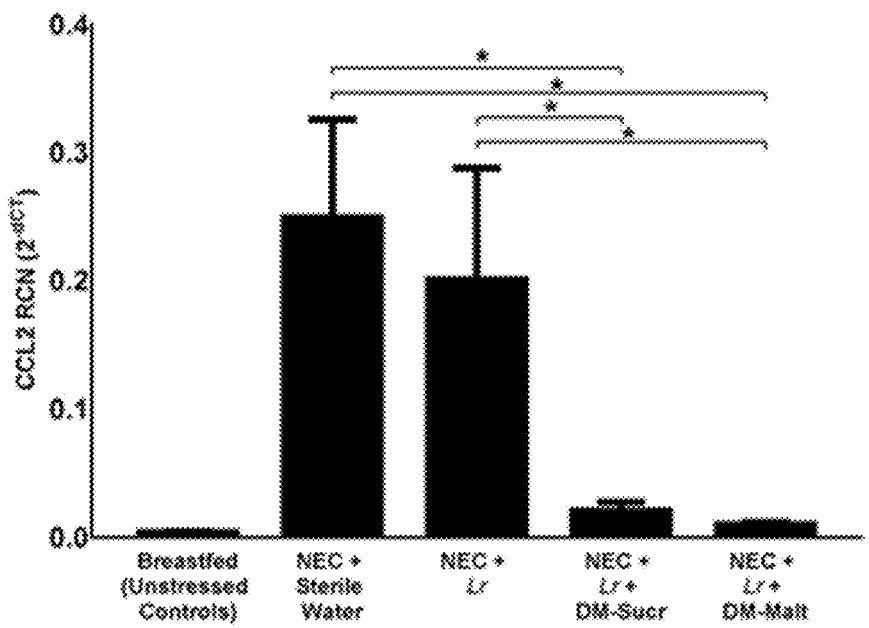
Figure 26D:
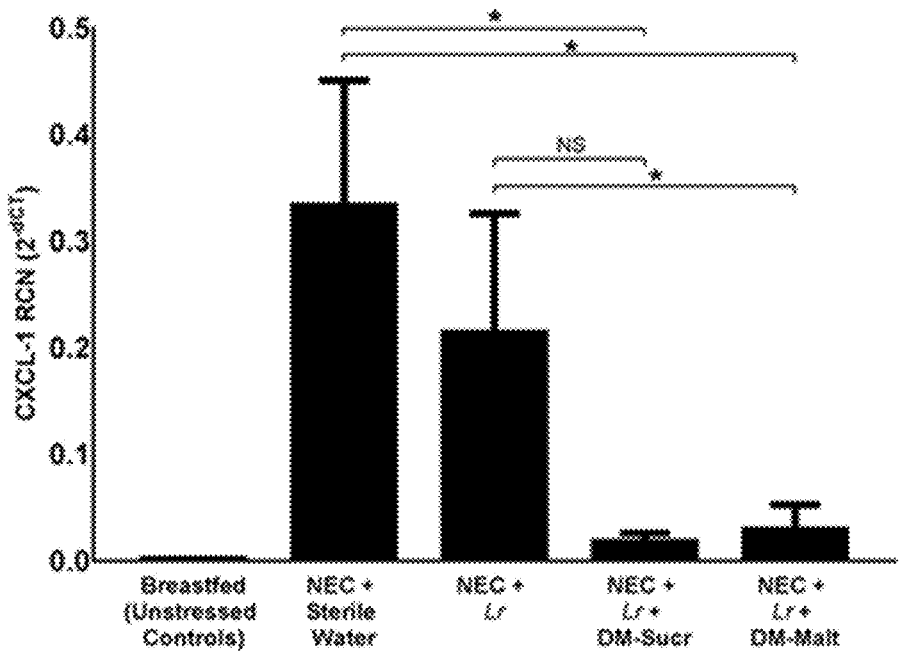
Figure 26E:
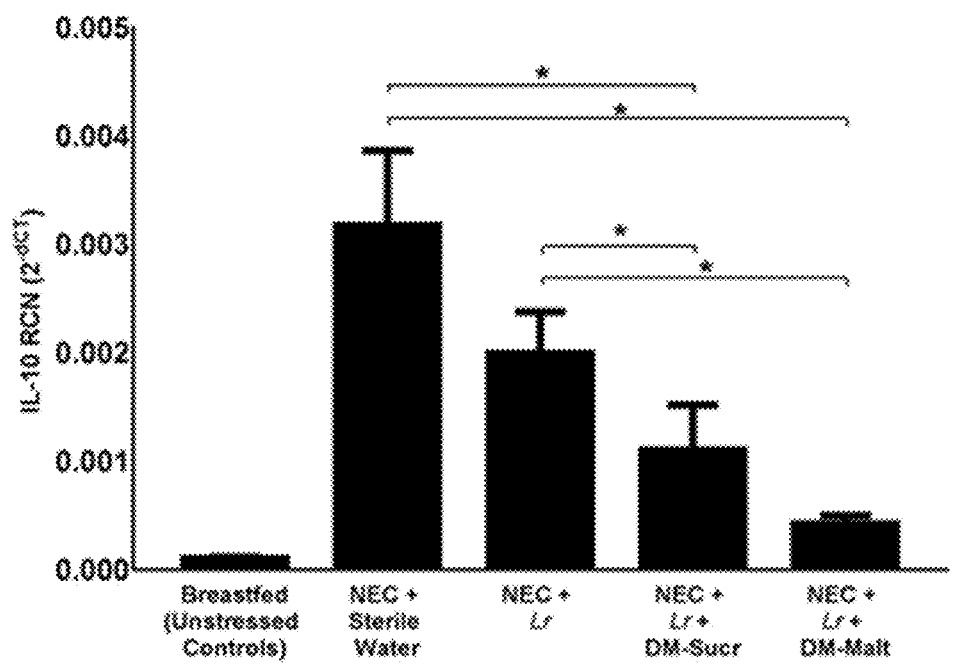

Effect of Lr biofilm formation on Lr persistence in the GI tract. After 48 h of the experimental NEC protocol, the amount of luminescence detected in the small intestine of pups that received a single dose of planktonic Lr was $6.2 \times 10^3 \pm 1.2 \times 10^3$ RLU/mg tissue, which increased to $1.1 \times 10^4 \pm 4.8 \times 10^3$ RLU/mg tissue in pups that received Lr+DM-Sucr albeit not significantly (p=0.322) (FIG. 25). In contrast, in the large intestine there was significantly more luminescence detected in pups that received Lr+DM-Sucr compared to pups that received Lr alone ($6.4 \times 10^4 \pm 1.7 \times 10^4$ vs. $2.3 \times 10^4 \pm 4.2 \times 10^3$ RLU/mg tissue, p=0.038).

Effect of Lr biofilm formulation on markers of inflammation. Untreated pups subjected to experimental NEC, as well as pups treated with a single dose of Lr, had significant elevation of IL-6, IL1-β, CCL-2, CXCL-1, and IL-10 (FIGS. 26A-26E). However, expression of each of these cytokines was substantially reduced when pups were treated with a single dose of Lr+DM-Sucr or Lr+DM-Malt. Compared to pups treated with planktonic Lr, the administration of Lr+DM-Sucr or Lr+DM-Malt led to a statistically significant reduction in the expression of IL-6, IL-1β, CCL-2, and IL-10. CXCL-1 expression was significantly reduced with the administration of Lr+DM-Malt but not Lr+DM-Sucr.

Figure 27:
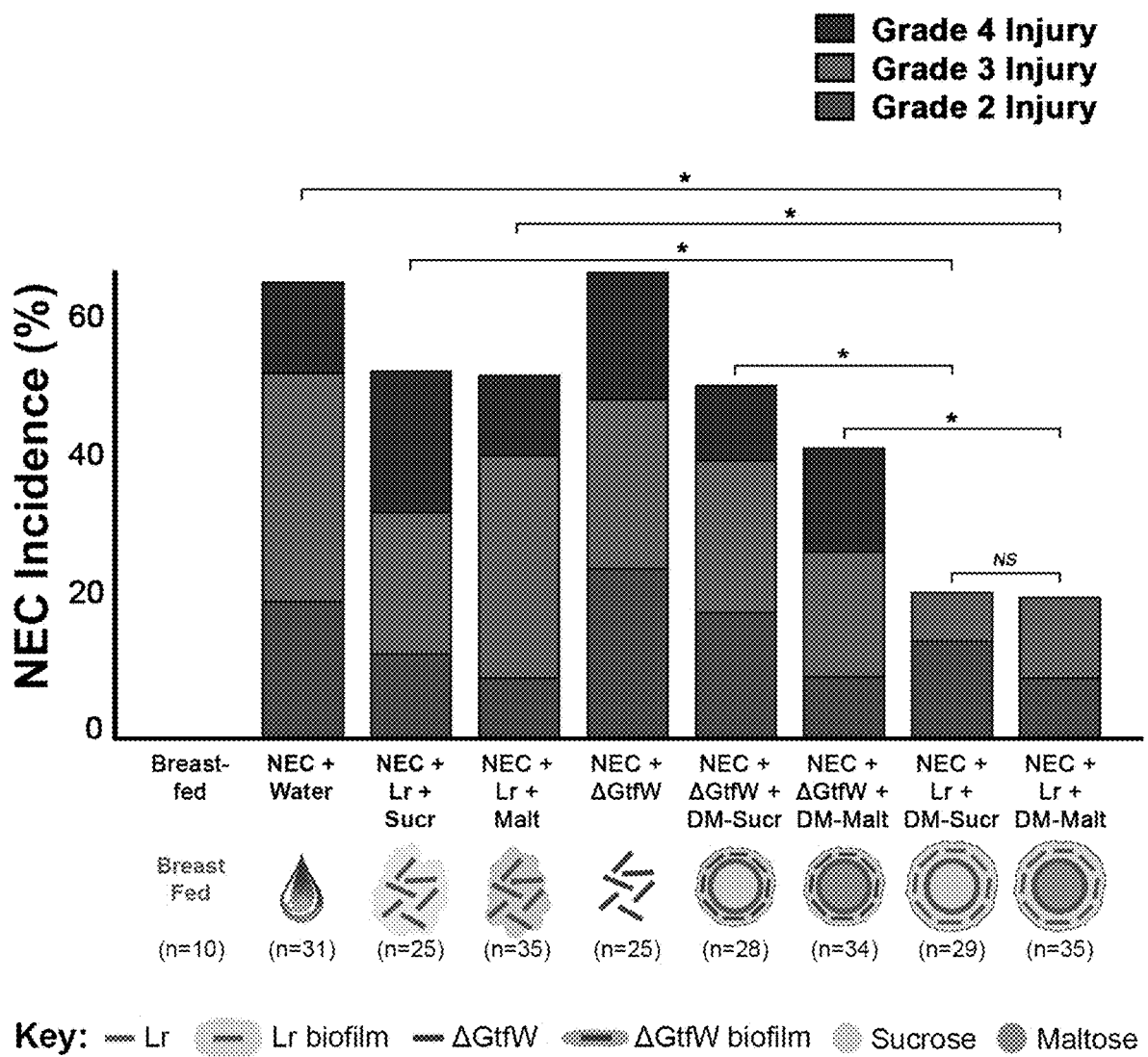
FIG. 27 shows incidence and severity of NEC. Rat pups were delivered prematurely, given a single enteral treatment as indicated, and then subjected to the experimental NEC protocol. Pups were sacrificed when signs of clinical NEC developed or after 96 h, intestinal tissue was harvested, and H&E sections were graded to determine the extent of intestinal damage. The incidence of NEC for each experimental group of pups is shown. For each treatment group the percentage of pups with grade 2, grade 3, and grade 4 injury are depicted. *p<0.05.

Effect of altered biofilm formation on NEC Incidence and Severity. In this experiment, control pups that received water alone had a NEC incidence of 65% (FIG. 27). In contrast, pups that received either Lr-DM-Sucr or Lr-DM-Malt had a significantly reduced NEC incidence of 21% (p<0.001) and 22% (p=0.002), respectively. However, these protective effects were lost with administration of the DM-deficient treatments Lr-Sucr and Lr-Malt, which had NEC incidences of 52% (p=0.014) and 51% (p=0.018), respectively (FIG. 27). Similarly, the protective effects of Lr were lost with administration of the GtfW-deficient treatments ΔGtfW-DM-Sucr and ΔGtfW-DM-Malt, which had NEC incidences of 50% (p=0.044) and 41% (p=0.035), respectively (FIG. 27). No breast fed pups developed NEC.

Discussion

Lr was originally isolated from human breast milk (Ghouri et al., 2014) and is present in healthy human intestine (Gomes et al., 2002; Gustave et al., 2013). Human-derived Lr strains belong to two distinct clades, clade II and clade VI (based on multi-locus sequencing), with only clade II strains possessing both anti-inflammatory and anti-microbial capabilities. The strain of Lr used for our current studies was clade II Lr ATCC23272 (also known as DSM 20016), and was originally isolated from the feces of a healthy human (Hall-Stoodley et al., 2004). Some clade II strains of Lr, including ATCC23272, can down-regulate both cytokine and chemokine production by colonic epithelial cells stimulated with C. rodentium (Heydorn et al., 2000; Higgins et al., 1999) Lr has also been shown to reduce intestinal inflammation in both juvenile and adult animals (Hoy, 2012; Ito et al., 2008). Furthermore, clade II strains of Lr produce antimicrobial compounds, the best characterized of which is reuterin (Jacobsson et al., 1976), which is derived from the substrate glycerol. Reuterin is a potent anti-microbial compound that inhibits the growth of numerous pathogenic microorganisms such as Gram-positive bacteria, Gram-negative bacteria, fungi, and protozoa (Johnston et al., 2012). Importantly, clade II strains readily form a biofilm, a community architecture of bacteria adhered to a surface, where the bacteria are encased in a self-produced matrix of extracellular polymeric substance (EPS). In addition, Lr has great affinity for the cross-linked dextran of DM, which results in excellent binding and subsequent biofilm formation (Eaton et al., 2011). For these reasons, along with the accumulating evidence that Lr is beneficial in human diseases such as colic (Justice et al, 2012), diarrhea (Kailasapathy, 2014), IgE-mediated eczema (Kralj et al., 2004), and NEC (Kralj et al., 2002), Lr was chosen for use in the current experiments.

In this study, Applicants showed that administration of a single dose of Lr adhered to DM in a biofilm state is superior to a single dose of planktonic administration of Lr for the prevention of experimental NEC. Importantly, the beneficial effects of the Lr biofilm can be significantly enhanced with the addition of either sucrose or maltose to the DM lumen. In addition to reducing NEC incidence, Lr+DM-Sucr and Lr+DM-Malt increased survival. These treatments reduced intestinal permeability during experimental NEC, thus preserving gut barrier function, and facilitated persistence of Lr in the intestinal tract. Importantly, this probiotic administration strategy also reduced the excessive inflammation characteristic of NEC.

DM are biodegradable, non-immunogenic, non-mutagenic, non-allergenic, and Generally Recognized As Safe (GRAS) by the FDA. They have been used in numerous FDA-approved medical products to date, including Solesta™, a bulking gel injected submucosally in the anal canal for treatment of fecal incontinence (Lebeis et al., 2008), Debrisan®, a cicatrizant wound dressing (Leemhuis et al., 2013), and Deflux®, a bulking gel used to treat vesicoureteral reflux (Lin et al., 2008). These long-standing uses of DM provide evidence for safety in human administration. Further, the DM lumen can be filled with compounds useful to Lr but limited in vivo, which diffuse over time directly to Lr adhered to DM (Lr+DM) as they transit the GI tract after enteral administration.

Changes in the microbial community such as the increasing prevalence of Proteobacteria (which includes many commonly observed Gram-negative pathogens)[2] have been reported in infants prior to the onset of NEC (Lukic et al., 2012). One large observational prospective study showed an increased proportion of Gammaproteobacteria and decreased proportion of Negativicutes in infants that went on to develop NEC compared to control infants (Cleusix et al., 2007). A separate systematic review provided similar findings, demonstrating an increase in Proteobacteria and a decrease in Firmicutes and Bacteroidetes preceeding NEC in preterm infants (Collins and Gibson, 1999). In some cases the pathogen *Cronobacter sakazakii* has been definitively linked to NEC outbreaks (Macfarlane et al., 2007; Macfarlane et al., 2005). These findings provide further evidence that dysbiosis is central the development of NEC

EQUIVALENTS

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that the materials, methods, and examples provided here are representative of preferred embodiments, are exemplary, and are not intended as limitations on the scope of the invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

TABLE 4

| Gram (+) - only HU, Gram (−) - all have HU some also IHF | | |
|---|---|---|
| Bacteria strain | Abbreviation | Protein name(s) |
| *S. sobrinus* 6715 | Ss | 1310 (HU) |
| *S. pyogenes* MGAS10270 | Spyog | Spy1239 (HU) |
| *S. gordonii* Challis NCTC7868 | Sg | SGO_0701 (HlpA) |
| *S. agalactiae* (Group B Strep)2603V/R | GBS | SAG_0505 (Hup) |
| *S. mutans* UA159 | Sm | Smu_589 (HU) |
| *S. pneumoniae* R6 | Spneu | spr1020 (HU) |
| *S. gallolyticus* UCN34 (*S. bovis*) | Sgall | YP_003430069 (HlpA) |
| *S. aureus* MW2 | Sa | MW1362 (HU) |
| *S. epidermidis* RP62A | Se | SERP1041 (Hup) |

TABLE 4-continued

Gram (+) - only HU, Gram (−) - all have HU some also IHF

| Bacteria strain | Abbreviation | Protein name(s) |
|---|---|---|
| *E. coli* K12-MG1655 | Ec | b1712 (HimA) |
| | | b0912 (HimD) |
| | | (HupA) |
| | | (HupB) |
| *H. influenza* KW20 Rd | Hi | HI1221 (HimA) |
| | | HI1313 (HimD) |
| | | HI0430 (HupA) |
| *Salmonella enteric serovar typhi* CT18 | Salm | Sty1771 (HimA) |
| | | Sty0982 (HimD) |
| *Aggregatibacter actinomycetemcomitans* D11S-1 | Aa | YP_003255965 (IHFalpha) |
| | | YP_003256209 (IhfB) |
| *P. gingivalis* W83 | Pg | YP_003255304 (HU) |
| | | PG_0121 (Hup-1) |
| | | PG_1258 (Hup-2) |
| *N. gonorrhoeae* FA1090 (Oklahoma) | Ng | NGO603 (IHFβ) |
| | | NGO030 (IHFα) |
| *N. meningitides* MC58 | Nm | NMB_0729 (HimA) |
| | | NMB_1302 (HimA) |
| *P. aeruginosa* | Pa | PA3161 (HimD) |
| | | PA1804 (HupB) |
| | | PA2758 (HimA) |
| *H. pylori* 26695 | Hp | Hp0835 (Hup) |
| *B. burgdorferi* B31 | Bb | BB_0232 (Hbb) |
| *Moraxella catarrhalis* RH4 | Mc | YP_003626307 (HimA) |
| | | YP_003627027 (HimD) |
| | | YP_003626775 (HupB) |
| *V. cholera* El Tor N16961 | Vc | VC_0273 (HupA) |
| | | VC_1914 (HipB) |
| | | VC_1919 (HupB) |
| | | VC_1222 (HimA) |
| *Burkholderia cenocepacia* HI2424 | Bc | Bcen2424_1048 (IHFB) |
| | | Bcen2424_1481 (IHFA) |
| *Burkholderia pseudomallei* 668 | Bp | BURPS668_2881 (IHFB) |
| | | BURPS668_1718 (IHFA) |
| *Mycobacterium tuberculosis* CDC1551 | Mtb | MT_3064 (HU) |
| *Mycobacterium smegmatis* MC2 | Ms | MSMEG_2389 (Hup) |
| *Treponema denticola* ATCC 35405 | Td | TDE_1709 (HU) |
| *Treponema palladium* Nichols | Tp | TP_0251 (DNA binding protein II) |
| *Prevotella melaninogenica* ATCC 25845 | Pm | PREME0022_2103 (HupB) |
| | | PREME0022_0268 (HupA) |
| | | PREME0022_0341 (Hup) |
| | | PREME0022_0340 (HimA) |
| *Prevotella intermedia* 17 | Pi | PIN_A0704 (Hup) |
| | | PIN_A1504 (Hup-2) |
| | | PIN_0345 (HimA) |
| | | PIN_0343 (Hypothetical protein) |
| *Bordetella pertusis* Tohama 1 | Bpert | BP2572 (IhfA) |
| | | BP3530 (HupB) |
| | | BP0951 (IhfB) |
| *Enterococcus faecalis* V583 | Ef | Ef1550 (hup) |

TABLE 6

Physical properties of Sephadex ® dextranomer microspheres

| Gel type | Dry bead size (μm) Low | Dry bead size (μm) High | Wet bead size (μm) Low | Wet bead size (μm) High | Permeability K* | Fractionation [Mr] globular proteins | Fractionation [Mr] dextrans | Exclusion limit (Da) | Swelling factor (ml/g) |
|---|---|---|---|---|---|---|---|---|---|
| G-10 | 40 | 120 | 55 | 165 | 19 | 700 | 700 | >700 | 2-3 |
| G-15 | 40 | 120 | 60 | 180 | 18 | 1,500 | 1,500 | >1,500 | 2.5-3.5 |
| G-25 superfine | 10 | 40 | 17 | 70 | 9 | 1,000-5,000 | 100-100 | >5,000 | 4-6 |
| G-25 fine | 20 | 80 | 35 | 140 | 30 | 1,000-5,000 | 100-100 | >5,000 | 4-6 |
| G-25 medium | 50 | 150 | 85 | 260 | 80 | 1,000-5,000 | 100-100 | >5,000 | 4-6 |
| G-25 coarse | >100 | # | 87 | 510 | 290 | 1,000-5,000 | 100-5,000 | >5,000 | 4-6 |
| G-50 superfine | 20 | 50 | 20 | 80 | 13.5 | 1,000-30,000 | 500-10,000 | >30,000 | 9-11 |
| G-50 fine | 20 | 80 | 34 | 208 | 36 | 1,000-30,000 | 500-10,000 | >30,000 | 9-11 |
| G-50 coarse | 100 | 300 | 200 | 610 | 400 | 1,000-30,000 | 500-10,000 | >30,000 | 9-11 |

TABLE 6-continued

Physical properties of Sephadex ® dextranomer microspheres

| Gel type | Dry bead size (μm) Low | Dry bead size (μm) High | Wet bead size (μm) Low | Wet bead size (μm) High | Permeability K* | Fractionation [Mr] globular proteins | Fractionation [Mr] dextrans | Exclusion limit (Da) | Swelling factor (ml/g) |
|---|---|---|---|---|---|---|---|---|---|
| G-75 superfine | 20 | 50 | 22 | 143 | # | 3,000-70,000 | 1,000-100,000 | >70,000 | 12-15 |
| G-75 | 40 | 120 | 90 | 280 | # | 3,000-80,000 | 1,000-50,000 | >70,000 | 12-15 |
| G-100 superfine | 10 | 40 | 25 | 100 | # | 4,000-100,000 | 1,000-100,000 | >100,000 | 15-20 |
| G-100 | 40 | 120 | 100 | 310 | # | 4,000-150,000 | 1,000-100,000 | >150,000 | 15-20 |

*Darcy's Law: $U = K (\Delta P) (L^{-1})$
U = linear flow rate in cm/h;
ΔP = pressure drop over bed in cm H2O;
L = bed height in cm;
K = specific permeability constant of particle size and water regain
not provided by manufacturer

REFERENCES

1. Agerholm-Larsen, L., Bell, M. L., Grunwald, G. K., and Astrup, A. (2000). The effect of a probiotic milk product on plasma cholesterol: a meta-analysis of short-term intervention studies. *European Journal of Clinical Nutrition* 54(11), 856-860. doi: DOI 10.1038/sj.ejcn.1601104.
2. Araya, M., Morelli, L., Reid, G., Sanders, M. E., and Stanton, C. (2006). *Probiotics in food: health and nutritional properties and guidelines for evaluation*. Rome: Food and Agriculture Organization of the United Nations: World Health Organization.
3. Argues, J. L., Fernandez, J., Gaya, P., Nunez, M., Rodriguez, E., and Medina, M. (2004). Antimicrobial activity of reuterin in combination with nisin against food-borne pathogens. *International Journal of Food Microbiology* 95(2), 225-229. doi: 10.1016/j.ijfoodmicro.2004.03.009.
4. Asmerom, M., Crowe, L., and Marin, T. (2015). Understanding the Biologic Therapies of Probiotics, Prebiotics, and Synbiotics: Exploring Current Evidence for Use in Premature Infants for the Prevention of Necrotizing Enterocolitis. *J Perinat Neonatal Nurs* 29(3), 240-247. doi: 10.1097/JPN.0000000000000120.
5. L. T. Axelsson, et al., Production of a Broad Spectrum Antimicrobial Substance by *Lactobacillus Reuteri*, Microbial Ecology in Health and Disease, 2 (1989).
6. M. T. Bailey, et al., Stressor Exposure Disrupts Commensal Microbial Populations in the Intestines and Leads to Increased Colonization by Citrobacter Rodentium, Infect Immun, 78 (2010), 1509-19.
7. Bai, Y., van der Kaaij, R. M., Leemhuis, H., Pijning, T., van Leeuwen, S. S., Jin, Z., et al. (2015). Biochemical Characterization of the *Lactobacillus reuteri* Glycoside Hydrolase Family 70 GTFB Type of 4,6-alpha-Glucanotransferase Enzymes That Synthesize Soluble Dietary Starch Fibers. *Appl Environ Microbiol* 81(20), 7223-7232. doi: 10.1128/AEM.01860-15.
8. X. M. Ben, et al., Low Level of Galacto-Oligosaccharide in Infant Formula Stimulates Growth of Intestinal *Bifidobacteria* and *Lactobacilli*, World J Gastroenterol, 14 (2008), 6564-8.
9. R. E. Black, et al., W. H. O. Child Health Epidemiology Reference Group of, and Unicef, "Global, Regional, and National Causes of Child Mortality in 2008: A Systematic Analysis", Lancet, 375 (2010), 1969-87.
10. C. P. Braegger, and T. T. MacDonald, Immune Mechanisms in Chronic Inflammatory Bowel Disease, Ann Allergy, 72 (1994), 135-41.
11. K. A. Brandstetter, et al., Antibodies Directed against Integration Host Factor Mediate Biofilm Clearance from Nasopore, Laryngoscope (2013).
12. Cadieux, P., Wind, A., Sommer, P., Schaefer, L., Crowley, K., Britton, R. A., et al. (2008). Evaluation of reuterin production in urogenital probiotic *Lactobacillus reuteri* RC-14. *Appl Environ Microbiol* 74(15), 4645-4649. doi: 10.1128/AEM.00139-08.
13. Chang, J. C., LaSarre, B., Jimenez, J. C., Aggarwal, C., and Federle, M. J. (2011). Two group A streptococcal peptide pheromones act through opposing Rgg regulators to control biofilm development. *PLoS Pathog* 7(8), e1002190. doi: 10.1371/journal.ppat.1002190.
14. Cleusix, V., Lacroix, C., Vollenweider, S., Duboux, M., and Le Blay, G. (2007). Inhibitory activity spectrum of reuterin produced by *Lactobacillus reuteri* against intestinal bacteria. *BMC Microbiol* 7, 101. doi: 10.1186/1471-2180-7-101.
15. Collins, M. D., and Gibson, G. R. (1999). Probiotics, prebiotics, and synbiotics: approaches for modulating the microbial ecology of the gut. *Am J Clin Nutr* 69(5), 1052S-1057S.
16. Cook, M. T., Tzortzis, G., Charalampopoulos, D., and Khutoryanskiy, V. V. (2012). Microencapsulation of probiotics for gastrointestinal delivery. *J Control Release* 162(1), 56-67. doi: 10.1016/j.jconrel.2012.06.003.
17. Cotter, P. D., Gahan, C. G., and Hill, C. (2001). A glutamate decarboxylase system protects Listeria monocytogenes in gastric fluid. *Mol Microbiol* 40(2), 465-475.
18. Danhier, F., Ansorena, E., Silva, J. M., Coco, R., Le Breton, A., and Preat, V. (2012). PLGA-based nanoparticles: an overview of biomedical applications. *J Control Release* 161(2), 505-522. doi: 10.1016/j.jconrel.2012.01.043.
19. de Chaumont, F., Dallongeville, S., Chenouard, N., Herve, N., Pop, S., Provoost, T., et al. (2012). Icy: an open bioimage informatics platform for extended reproducible research. *Nat Methods* 9(7), 690-696. doi: 10.1038/nmeth.2075.
20. De Man, J. C., Rogosa, M., and Sharpe, M. E. (1960). A medium for the cultivation of *Lactobacilli*. *J Appl Bact* 23(1), 6. doi: 10.1111/j.1365-2672.1960.tb00188.x.
21. J. C. De Man, M. et al., A Medium for the Cultivation of Lactobacilli, J Applied Bacteriology, 23 (1960), 130-35.
22. Devaraj, A., Justice, S. S., Bakaletz, L. O., and Goodman, S. D. (2015). DNABII proteins play a central role in UPEC biofilm structure. *Mol Microbiol* 96(6), 1119-1135. doi: 10.1111/mmi.12994.

23. de Vos, W. M. (2015). Microbial biofilms and the human intestinal microbiome. *Npj Biofilms And Microbiomes* 1, 15005. doi: 10.1038/npjbiofilms.2015.5.
24. de Vrese, M., and Schrezenmeir, J. (2008). Probiotics, prebiotics, and synbiotics. *Adv Biochem Eng Biotechnol* 111, 1-66. doi: 10.1007/10_2008_097.
25. De Weirdt, R., Crabbé, A., Roos, S., Vollenweider, S., Lacroix, C., van Pijkeren, J. P., et al. (2012). Glycerol supplementation enhances *L. reuteri*'s protective effect against S. Typhimurium colonization in a 3-D model of colonic epithelium. *PloS One* 7, e37116. doi: 10.1371/journal.pone.0037116.
26. Ding, W. K., and Shah, N. P. (2007). Acid, bile, and heat tolerance of free and microencapsulated probiotic bacteria. *J Food Sci* 72(9), M446-450. doi: 10.1111/j.1750-3841.2007.00565.x.
27. Dressman, J. B., Berardi, R. R., Dermentzoglou, L. C., Russell, T. L., Schmaltz, S. P., Barnett, J. L., et al. (1990). Upper gastrointestinal (GI) pH in young, healthy men and women. *Pharm Res* 7(7), 756-761.
28. K. A. Eaton, A. et al., Probiotic Lactobacillus Reuteri Ameliorates Disease Due to Enterohemorrhagic Escherichia Coli in Germfree Mice, Infect Immun, 79 (2011), 185-91.
29. L. Eckmann, Animal Models of Inflammatory Bowel Disease: Lessons from Enteric Infections, Ann N Y Acad Sci, 1072 (2006), 28-38.
30. el-Ziney, M. G., and Debevere, J. M. (1998). The effect of Reuterin on Listeria monocytogenes and *Escherichia coli* 0157:H7 in milk and cottage cheese. *J Food Prot* 61(10), 1275-1280.
31. Engels, C., Schwab, C., Zhang, J., Stevens, M. J., Bieri, C., Ebert, M. O., et al. (2016). Acrolein contributes strongly to antimicrobial and heterocyclic amine transformation activities of reuterin. *Sci Rep* 6, 36246. doi: 10.1038/srep36246.
32. Freire, M. O., Devaraj, A., Young, A., Navarro, J. B., Downey, J. S., Chen, C., et al. (2016). A Bacterial Biofilm Induced Oral Osteolytic Infection Can be Successfully Treated by Immuno-Targeting an Extracellular Nucleoid Associated Protein. *Mol Oral Microbiol*. doi: 10.1111/omi.12155.
33. Freire, M. O., Sedghizadeh, P. P., Schaudinn, C., Gorur, A., Downey, J. S., Choi, J. H., et al. (2011). Development of an animal model for Aggregatibacter actinomycetemcomitans biofilm-mediated oral osteolytic infection: a preliminary study. *J Periodontol* 82(5), 778-789. doi: 10.1902/jop.2010.100263.
34. Frese, S. A., Benson, A. K., Tannock, G. W., Loach, D. M., Kim, J., Zhang, M., et al. (2011). The evolution of host specialization in the vertebrate gut symbiont *Lactobacillus reuteri*. *PLoS Genet* 7(2), e1001314. doi: 10.1371/journal.pgen.1001314.
35. Ganzle, M. G., and Follador, R. (2012). Metabolism of oligosaccharides and starch in lactobacilli: a review. *Front Microbiol* 3, 340. doi: 10.3389/fmicb.2012.00340.
36. Gao, C., Major, A., Rendon, D., Lugo, M., Jackson, V., Shi, Z., et al. (2015). Histamine H2 Receptor-Mediated Suppression of Intestinal Inflammation by Probiotic *Lactobacillus reuteri*. *MBio* 6(6), e01358-01315. doi: 10.1128/mBio.01358-15.
37. Geier, M. S., Butler, R. N., and Howarth, G. S. (2007). Inflammatory bowel disease: current insights into pathogenesis and new therapeutic options; probiotics, prebiotics and synbiotics. *International Journal of Food Microbiology* 115(1), 1-11. doi: 10.1016/j.ijfoodmicro.2006.10.006.
38. Ghouri, Y. A., Richards, D. M., Rahimi, E. F., Krill, J. T., Jelinek, K. A., and DuPont, A. W. (2014). Systematic review of randomized controlled trials of probiotics, prebiotics, and synbiotics in inflammatory bowel disease. *Clin Exp Gastroenterol* 7, 473-487. doi: 10.2147/CEG.S27530.
39. Gomes, R., Meek, M. E., and Eggleton, M. (2002). *Acrolein*. Geneva: World Health Organization.
40. J. E. Gustave, et al., Targeting Bacterial Integration Host Factor to Disrupt Biofilms Associated with Cystic Fibrosis, J Cyst Fibros, 12 (2013), 384-9.
41. Hall-Stoodley, L., Costerton, J. W., and Stoodley, P. (2004). Bacterial biofilms: from the natural environment to infectious diseases. *Nat Rev Microbiol* 2(2), 95-108. doi: 10.103 8/nrmicro821.
42. Heydorn, A., Nielsen, A. T., Hentzer, M., Sternberg, C., Givskov, M., Ersboll, B. K., et al. (2000). Quantification of biofilm structures by the novel computer program COMSTAT. *Microbiology-Uk* 146, 2395-2407.
43. L. M. Higgins, et al., Citrobacter Rodentium Infection in Mice Elicits a Mucosal Th1 Cytokine Response and Lesions Similar to Those in Murine Inflammatory Bowel Disease, Infect Immun, 67 (1999), 3031-9.
44. Hoy, S. M. (2012). Dextranomer in stabilized sodium hyaluronate (Solesta(R)): in adults with faecal incontinence. *Drugs* 72(12), 1671-1678. doi: 10.2165/11209030-000000000-00000.
45. F. Ito, H. et al., Factors Affecting the Loading Efficiency of Water-Soluble Drugs in Plga Microspheres, Colloids Surf B Biointerfaces, 61 (2008), 25-9.
46. Jacobsson, S., Jonsson, L., Rank, F., and Rothman, U. (1976). Studies on healing of Debrisan-treated wounds. *Scand J Plast Reconstr Surg* 10(2), 97-101.
47. Johnston, B. C., Ma, S. S. Y., Goldenberg, J. Z., Thorlund, K., Vandvik, P. O., Loeb, M., et al. (2012). Probiotics for the Prevention of Clostridium difficile-Associated Diarrhea A Systematic Review and Meta-analysis. *Annals of Internal Medicine* 157(12), 878-U225.
48. S. S. Justice, B. et al., Aberrant Community Architecture and Attenuated Persistence of Uropathogenic *Escherichia Coli* in the Absence of Individual Ihf Subunits, PLoS One, 7 (2012), e48349.
49. Kailasapathy, K. (2014). Microencapsulation for Gastrointestinal Delivery of Probiotic Bacteria. *Nano-and Microencapsulation for Foods*, 167-197. doi: Book_Doi 10.1002/9781118292327.
50. Kralj, S., van Geel-Schutten, G. H., Dondorff, M. M. G., Kirsanovs, S., van der Maarel, M. J. E. C., and Dijkhuizen, L. (2004). Glucan synthesis in the genus *Lactobacillus*: isolation and characterization of glucansucrase genes, enzymes and glucan products from six different strains. *Microbiology-Sgm* 150, 3681-3690. doi: 10.1099/mic.0.27321-0.
51. Kralj, S., van Geel-Schutten, G. H., Rahaoui, H., Leer, R. J., Faber, E. J., van der Maarel, M. J., et al. (2002). Molecular characterization of a novel glucosyltransferase from *Lactobacillus reuteri* strain 121 synthesizing a unique, highly branched glucan with alpha-(1→4) and alpha-(1→6) glucosidic bonds. *Appl Environ Microbiol* 68(9), 4283-4291.
52. S. L. Lebeis, et al., Protective and Destructive Innate Immune Responses to Enteropathogenic Escherichia Coli and Related a/E Pathogens, Future Microbiol, 3 (2008), 315-28.
53. Leemhuis, H., Dijkman, W. P., Dobruchowska, J. M., Pijning, T., Grijpstra, P., Kralj, S., et al. (2013). 4,6-alpha-Glucanotransferase activity occurs more widespread in 53. *Lactobacillus* strains and constitutes a separate GH70 subfamily. *Appl Microbiol Biotechnol* 97(1), 181-193. doi: 10.1007/s00253-012-3943-1.

54. Y. P. Lin, et al., Probiotic Lactobacillus Reuteri Suppress Proinflammatory Cytokines Via C-Jun, Inflamm Bowel Dis, 14 (2008), 1068-83.

55. Lukic, J., Strahinic, I., Jovcic, B., Filipic, B., Topisirovic, L., Kojic, M., et al. (2012). Different roles for lactococcal aggregation factor and mucin binding protein in adhesion to gastrointestinal mucosa. *Appl Environ Microbiol* 78(22), 7993-8000. doi: 10.1128/AEM.02141-12.

56. Macfarlane, S., and Dillon, J. F. (2007). Microbial biofilms in the human gastrointestinal tract. *J Appl Microbiol* 102(5), 1187-1196. doi: 10.1111/j.1365-2672.2007.03287.x.

57. Macfarlane, S., Woodmansey, E. J., and Macfarlane, G. T. (2005). Colonization of mucin by human intestinal bacteria and establishment of biofilm communities in a two-stage continuous culture system. *Appl Environ Microbiol* 71(11), 7483-7492. doi: 10.1128/AEM.71.11.7483-7492.2005.

58. Mackos, A. R., Galley, J. D., Eubank, T. D., Easterling, R. S., Parry, N. M., Fox, J. G., et al. (2016). Social stress-enhanced severity of Citrobacter rodentium-induced colitis is CCL2-dependent and attenuated by probiotic *Lactobacillus reuteri*. *Mucosal Immunol* 9(2), 515-526. doi: 10.1038/mi.2015.81.

59. Maintz, L., and Novak, N. (2007). Histamine and histamine intolerance. *Am J Clin Nutr* 85(5), 1185-1196.

60. Mashburn-Warren, L., Morrison, D. A., and Federle, M. J. (2012). The cryptic competence pathway in Streptococcus pyogenes is controlled by a peptide pheromone. *J Bacteriol* 194(17), 4589-4600. doi: 10.1128/JB.00830-12.

61. McFarland, L. V. (2006). Meta-analysis of probiotics for the prevention of antibiotic associated diarrhea and the treatment of Clostridium difficile disease. *American Journal of Gastroenterology* 101(4), 812-822. doi: 10.1111/j.1572-0241.2006.00465.x.

62. Merritt, J., Senpuku, H., and Kreth, J. (2016). Let there be bioluminescence: development of a biophotonic imaging platform for in situ analyses of oral biofilms in animal models. *Environ Microbiol* 18(1), 174-190. doi: 10.1111/1462-2920.12953.

63. Miyoshi, Y., Okada, S., Uchimura, T., and Satoh, E. (2006). A mucus adhesion promoting protein, MapA, mediates the adhesion of *Lactobacillus reuteri* to Caco-2 human intestinal epithelial cells. *Biosci Biotechnol Biochem* 70(7), 1622-1628. doi: 10.1271/bbb.50688.

64. Monchois, V., Willemot, R. M., and Monsan, P. (1999). Glucansucrases: mechanism of action and structure-function relationships. *FEMS Microbiol Rev* 23(2), 131-151. doi: Doi 10.1016/S0168-6445(98)00041-2.

65. Mooser, G., Shur, D., Lyou, M., and Watanabe, C. (1985). Kinetic-Studies on Dextransucrase from the Cariogenic Oral Bacterium *Streptococcus*-Mutans. *Journal of Biological Chemistry* 260(11), 6907-6915.

66. National Institutes of Health, 2013, http://grants2.nih.gov/grants/guide/pa-files/PA-06-537.html.

67. Neu, J., and Walker, W. A. (2011). Necrotizing enterocolitis. *N Engl J Med* 364(3), 255-264. doi: 10.1056/NEJMra1005408.

68. Nguyen, T. D. T., Kang, J. H., and Lee, M. S. (2007). Characterization of *Lactobacillus* plantarum PH04, a potential probiotic bacterium with cholesterol-lowering effects. *International Journal of Food Microbiology* 113 (3), 358-361. doi: 10.1016/j.ijfoodmicro.2006.08.015.

69. L. A. Novotny, et al., Structural Stability of Burkholderia Cenocepacia Biofilms Is Reliant on Edna Structure and Presence of a Bacterial Nucleic Acid Binding Protein, PLoS One, 8 (2013), e67629.

70. Olson, J. K., Rager, T. M., Navarro, J. B., Mashburn-Warren, L., Goodman, S. D., and Besner, G. E. (2016). Harvesting the benefits of biofilms: A novel probiotic delivery system for the prevention of necrotizing enterocolitis. *J Pediatr Surg* 51(6), 936-941. doi: 10.1016/j.jpedsurg.2016.02.062.

71. Porath, J., and Flodin, P. (1959). Gel filtration: a method for desalting and group separation. *Nature* 183(4676), 1657-1659.

72. G. A. Preidis, et al., Probiotics Stimulate Enterocyte Migration and Microbial Diversity in the Neonatal Mouse Intestine, FASEB J, 26 (2012), 1960-9.

73. L. A. Sarmiento-Rubiano, et al., Dietary Supplementation with Sorbitol Results in Selective Enrichment of *Lactobacilli* in Rat Intestine, Res Microbiol, 158 (2007), 694-701.

74. Savino, F., Cordisco, L., Tarasco, V., Palumeri, E., Calabrese, R., Oggero, R., et al. (2010). *Lactobacillus reuteri* DSM 17938 in infantile colic: a randomized, double-blind, placebo-controlled trial. *Pediatrics* 126(3), e526-533. doi: 10.1542/peds.2010-0433.

75. Schaefer, L., Auchtung, T. A., Hermans, K. E., Whitehead, D., Borhan, B., and Britton, R. A. (2010). The antimicrobial compound reuterin (3-hydroxypropionaldehyde) induces oxidative stress via interaction with thiol groups. *Microbiology* 156(Pt 6), 1589-1599. doi: 10.1099/mic.0.035642-0.

76. O. Schreiber, et al., *Lactobacillus Reuteri* Prevents Colitis by Reducing P-Selectin-Associated Leukocyte- and Platelet-Endothelial Cell Interactions, Am J Physiol Gastrointest Liver Physiol, 296 (2009), G534-42.

77. Schwab, C., Walter, J., Tannock, G. W., Vogel, R. F., and Ganzle, M. G. (2007). Sucrose utilization and impact of sucrose on glycosyltransferase expression in *Lactobacillus reuteri*. *Syst Appl Microbiol* 30(6), 433-443. doi: 10.1016/j.syapm.2007.03.007.

78. Soh, S. E., Aw, M., Gerez, I., Chong, Y. S., Rauff, M., Ng, Y. P. M., et al. (2009). Probiotic supplementation in the first 6 months of life in at risk Asian infants—effects on eczema and atopic sensitization at the age of 1 year. *Clinical and Experimental Aller* 39(4), 571-578. doi: 10.1111/j.1365-2222.2008.03133.x.

79. Spinier, J. K., Taweechotipatr, M., Rognerud, C. L., Ou, C. N., Tumwasorn, S., and Versalovic, J. (2008). Human-derived probiotic *Lactobacillus reuteri* demonstrate antimicrobial activities targeting diverse enteric bacterial pathogens. *Anaerobe* 14(3), 166-171. doi: 10.1016/j.anaerobe.2008.02.001.

80. Stefka, A. T., Feehley, T., Tripathi, P., Qiu, J., McCoy, K., Mazmanian, S. K., et al. (2014). Commensal bacteria protect against food allergen sensitization. *Proc Natl Acad Sci USA* 111(36), 13145-13150. doi: 10.1073/pnas.1412008111.

81. Stenberg, A., and Lackgren, G. (1995). A New Bioimplant for the Endoscopic Treatment of Vesicoureteral Reflux—Experimental and Short-Term Clinical-Results. *Journal of Urology* 154(2), 800-803. doi: Doi 10.1016/S0022-5347(01)67168-4.

82. Su, M. S., and Ganzle, M. G. (2014). Novel two-component regulatory systems play a role in biofilm formation of *Lactobacillus reuteri* rodent isolate 100-23. *Microbiology* 160(Pt 4), 795-806. doi: 10.1099/mic.0.071399-0.

83. Sung, V., Hiscock, H., Tang, M. L. K., Mensah, F. K., Nation, M. L., Satzke, C., et al. (2014). Treating infant colic with the probiotic *Lactobacillus reuteri*: double blind, placebo controlled randomised trial. *Bmj-British Medical Journal* 348. doi: 10.1136/Bmj.G2107.
84. N. Takemura, et al., Inulin Prolongs Survival of Intragastrically Administered *Lactobacillus* Plantarum No. 14 in the Gut of Mice Fed a High-Fat Diet, J Nutr, 140 (2010), 1963-9.
85. Talarico, T. L., Casas, I. A., Chung, T. C., and Dobrogosz, W. J. (1988). Production and isolation of reuterin, a growth inhibitor produced by *Lactobacillus reuteri*. *Antimicrobial Agents and Chemotherapy* 32, 1854-1858.
86. Thomas, C. M., Hong, T., van Pijkeren, J. P., Hemarajata, P., Trinh, D. V., Hu, W., et al. (2012). Histamine derived from probiotic *Lactobacillus reuteri* suppresses TNF via modulation of PKA and ERK signaling. *PLoS One* 7(2), e31951. doi: 10.1371/journal.pone.0031951.
87. Tieking, M., Kaditzky, S., Valcheva, R., Korakli, M., Vogel, R. F., and Ganzle, M. G. (2005). Extracellular homopolysaccharides and oligosaccharides from intestinal lactobacilli. *J Appl Microbiol* 99(3), 692-702. doi: 10.1111/j.1365-2672.2005.02638.x.
88. Turner, J. R. (2009). Intestinal mucosal barrier function in health and disease. *Nat Rev Immunol* 9(11), 799-809. doi: 10.1038/nri2653.
89. Updegraff, D. M. (1969). Semimicro determination of cellulose in biological materials. *Anal Biochem* 32(3), 420-424.
90. Van den Abbeele, P., Grootaert, C., Possemiers, S., Verstraete, W., Verbeken, K., and Van de Wiele, T. (2009). In vitro model to study the modulation of the mucin-adhered bacterial community. *Appl Microbiol Biotechnol* 83(2), 349-359. doi: 10.1007/s00253-009-1947-2.
91. van Zanten, G. C., Krych, L., Roytio, H., Forssten, S., Lahtinen, S. J., Abu Al-Soud, W., et al. (2014). Synbiotic *Lactobacillus acidophilus* NCFM and cellobiose does not affect human gut bacterial diversity but increases abundance of lactobacilli, bifidobacteria and branched-chain fatty acids: a randomized, double-blinded cross-over trial. *FEMS Microbiol Ecol* 90(1), 225-236. doi: 10.1111/1574-6941.12397.
92. Venugopalan, V., Shriner, K. A., and Wong-Beringer, A. (2010). Regulatory oversight and safety of probiotic use. *Emerg Infect Dis* 16(11), 1661-1665. doi: 10.3201/eid1611.100574.
93. Walter, J., Loach, D. M., Alqumber, M., Rockel, C., Hermann, C., Pfitzenmaier, M., et al. (2007). D-alanyl ester depletion of teichoic acids in *Lactobacillus reuteri* 100-23 results in impaired colonization of the mouse gastrointestinal tract. *Environ Microbiol* 9(7), 1750-1760. doi: 10.1111/j.1462-2920.2007.01292.x.
94. Walter, J., Schwab, C., Loach, D. M., Ganzle, M. G., and Tannock, G. W. (2008). Glucosyltransferase A (GtfA) and inulosucrase (Inu) of *Lactobacillus reuteri* TMW1.106 contribute to cell aggregation, in vitro biofilm formation, and colonization of the mouse gastrointestinal tract. *Microbiology* 154(Pt 1), 72-80. doi: 10.1099/mic.0.2007/010637-0.
95. Q. Xia, et al., Quantitative Analysis of Intestinal Bacterial Populations from Term Infants Fed Formula Supplemented with Fructo-Oligosaccharides, J Pediatr Gastroenterol Nutr, 55 (2012), 314-20.
96. Grasser, K. D., Teo, S. H., Lee, K. B., Broadhurst, R. W., Rees, C., Hardman, C. H., et al. (1998). DNA-binding properties of the tandem HMG boxes of high-mobility-group protein 1 (HMG1). *Eur J Biochem* 253(3), 787-795.
97. Venereau, E., Casalgrandi, M., Schiraldi, M., Antoine, D. J., Cattaneo, A., De Marchis, F., et al. (2012). Mutually exclusive redox forms of HMGB1 promote cell recruitment or proinflammatory cytokine release. *J Exp Med* 209(9), 1519-1528. doi: 10.1084/jem.20120189.

```
Sequence Listing
Seq. ID NO. 1: Full Length Wild type (wt) 86-028NP
Haemophilus influenzae IhfA; Genbank accession
No.: AAX88425.1, last accessed Mar. 21, 2011:
MATITKLDIIEYLSDKYHLSKQDTKNVVENFLEEIRLSLESGQDVKLSGF

GNFELRDKSSRPGRNPKTGDVVPVSARRVVTFKPGQKLRARVEKTK

Seq. ID NO. 2: Full Length wt 86-028NP Haemophilus
influenzae HU, Genbank accession No.:
YP_248142.1, last accessed Mar. 21, 2011:
MRFVTIFINHAFNSSQVRLSFAQFLRQIRKDTFKESNFLFNRRYKFMNKT

DLIDAIANAAELNKKQAKAALEATLDAITASLKEGEPVQLIGFGTFKVNE

RAARTGRNPQTGAEIQIAASKVPAFVSGKALKDAIK

Seq. ID NO. 3: Full Length wt R2846 Haemophilus
influenzae IhfA, Genbank accession No.:
ADO96375, last accessed Mar. 21, 2011:
MATITKLDIIEYLSDKYHLSKQDTKNVVENFLEEIRLSLESGQDVKLSGF

GNFELRDKSSRPGRNPKTGDVVPVSARRVVTFKPGQKLRARVEKTK

Seq. ID NO. 4: Full Length wt E. coli K12 IhfA;
Genbank accession No.: AAC74782.1, last accessed
Mar. 21, 2011:
MALTKAEMSEYLFDKLGLSKRDAKELVELFFEEIRRALENGEQVKLSGFG NFDLRDKNQRPGRNPKTGEDIPITARRVVTFRPGQKLKSRVENASPKDE;
DNA Genbank No. NC_000913

Seq. ID NO. 5: Full Length wt P. aeruginosa PA
01 IhfA; Genbank accession No.: AAG06126.1, last
accessed Mar. 21, 2011:
MGALTKAEIAERLYEELGLNKREAKELVELFFEEIRQALEHNEQVKLSGF

GNFDLRDKRQRPGRNPKTGEEIPITARRVVTFRPGQKLKARVEAYAGTKS

Seq. ID NO. 6: Full Length wt Rd Haemophilus
influenzae IhfA; Genbank accession No.:
AAC22959.1, last accessed Mar. 21, 2011:
MATITKLDIIEYLSDKYHLSKQDTKNVVENFLEEIRLSLESGQDVKLSGF

GNFELRDKSSRPGRNPKTGDVVPVSARRVVTFKPGQKLRARVEKTK

SEQ ID NO. 7: E. coli hupA, Genbank accession
No.: AP_003818, Last accessed Mar. 21, 2011:
MNKTQLIDVIAEKAELSKTQAKAALESTLAAITESLKEGDAVQLVGFGTF

KVNHRAERTGRNPQTGKEIKIAAANVPAFVSGKALKDAVK

SEQ ID NO. 8: E. coli hupB, Genbank accession
No.: AP_001090.1, Last accessed Mar. 21, 2011:
MNKSQLIDKIAAGADISKAAAGRALDAIIASVTESLKEGDDVALVGFGTF

AVKERAARTGRNPQTGKEITIAAAKVPSFRAGKALKDAVN

Seq. ID NO. 6 Full Length Wild type (wt) 86-028NP
Haemophilus influenzae IhfA; Genbank acce
Seq. ID NO. 6 Full Length Wild type (wt) 86-028NP
Haemophilus influenzae IhfA; Genbank accession
No.: AAX88425.1, last accessed Mar. 21, 2011:
MATITKLDIIEYLSDKYHLSKQDTKNVVENFLEEIRLSLESGQDVKLSGF

GNFELRDKSSRPGRNPKTGDVVPVSARRVVTFKPGQKLRARVEKTK
```

What is claimed is:

1. A composition comprising:
   a microsphere comprising dextran cross-linked with epichlorohydrin;
   a prebiotic; and
   a strain of *Lactobacillus reuteri* ("*L. reuteri*") that expresses glucosyltransferase (GTF) protein, wherein the prebiotic comprises an effective amount of a nutritional supplementation for the *L. reuteri* strain to support the formation of a biofilm.

2. The composition of claim 1, wherein the strain of *L. reuteri* is adhered to the microsphere.

3. The composition of claim 1, wherein the strain of *L. reuteri* is selected from the group consisting of: ATCC 23272, *L. reuteri* strain 100-23, ATCC PTA 6475, ATCC 55730, DSM 17938 and combination(s) thereof.

4. The composition of claim 1, wherein the prebiotic comprises a water-soluble carbohydrate, wherein the water-soluble carbohydrate comprises one or more of inulin, oligofructose, fructo-oligosaccharide, galacto-oligosaccharide, glucose, starch, maltose, maltodextrins, polydextrose, amylose, sucrose, fructose, lactose, isomaltulose, polyols, glycerol, carbonate, thiamine, choline, histidine, trehalose, nitrogen, sodium nitrate, ammonium nitrate, phosphorus, phosphate salts, hydroxyapatite, potassium, potash, sulfur, homopolysaccharide, heteropolysaccharide, cellulose, chitin, vitamins, or a combination thereof.

5. The composition of claim 4, wherein the water-soluble carbohydrate is maltose and/or sucrose.

6. The composition of claim 1, further comprising a pharmaceutically acceptable carrier or a biocompatible scaffold.

7. The composition of claim 1, wherein the strain of *L. reuteri* provides one or more of supporting anti-bacterial immunity, correcting dysbiosis, enhancing or supporting the gastrointestinal barrier, supporting or enhancing gastrointestinal motility, localized release of antibiotic compositions, or antagonizing disease-related bacterial infections.

8. A formulation comprising the composition of claim 1, wherein the composition is formulated in a dosage form selected from the group consisting of: suppository, within a biocompatible scaffold, powder, liquid, capsule, chewable tablet, swallowable tablet, buccal tablet, troche, lozenge, soft chew, solution, suspension, spray, tincture, decoction, infusion, and combinations thereof.

9. A method of treating a disease selected from the group consisting of inflammatory bowel disease (IBD), colitis, enteric infectious disease, necrotizing enterocolitis (NEC), infection-induced colitis, traveler's diarrhea, and psychological disorders in a subject in need thereof, comprising administering to the subject an effective amount of the composition of claim 1.

10. A method of preparing the composition of claim 1 comprising admixing a microsphere comprising dextran cross-linked with epichlorohydrin with [a biofilm-generating probiotic bacterium] the strain of *L. reuteri*, and a prebiotic.

11. The method of claim 10, wherein the [biofilm-generating probiotic bacterium is selected from the group consisting of:] strain of *L. reuteri* is selected from the group consisting of: ATCC 23272, *L. reuteri* strain 100-23, ATCC PTA 6475, ATCC 55730, DSM 17938 [*L. acidophilus, L. crispatus, L. gasseri, L. delbrueckii, L. salivarius, L. casei, L. paracasei, L. plantarum, L. rhamnosus, L. reuteri, L. brevis, L. buchneri, L. fermentum, L. rhamnosus, B. adolescentis, B. angulation, B. bifidum, B. breve, B. catenulatum, B. infantis, B. lactis, B. longum, B. pseudocatenulatum, S. thermophiles, Pseudomonas fluorescens, P. protegens, P. brassicacearum, P. aeruginosa, Azospirillum brabrasilense, A. lipferum, A. halopraeferens, A. irakense, Acetobacter diazotrophicus, Herbaspirillum seropedicae, Bacillus subtilis, Pseudomonas stutzeri, fluorescens, P. putida, P. cepacian, P. vesicularis, P. paucimobilis, Bacillus cereus, B. thuringiensis, B. sphaericus, Shewanella oneidensis, Geobacter bemidjiensis, G. metallireducens, G. sulfurreducens, G. uraniireducens, G. lovleyi, Serratia marcescens, Desulfovibrio vulgaris, D. desulfuricans, Dechloromonas aromatic, Deinococcus radiodurans, Methylibium petroleiphilum, Alcanivorax borkumensis, Archaeglobus fulgidus, Haloferax sp., Halobacterium sp.,*] and combination(s) [combinations] thereof.

* * * * *

UNITED STATES PATENT AND TRADEMARK OFFICE
CERTIFICATE OF CORRECTION

PATENT NO. : 11,497,780 B2
APPLICATION NO. : 16/820463
DATED : November 15, 2022
INVENTOR(S) : Steven D. Goodman et al.

It is certified that error appears in the above-identified patent and that said Letters Patent is hereby corrected as shown below:

In the Claims

At Column 96, Line 17 – "subject having a" should be added after "A method of treating a".

At Column 96, Line 26 – "[a biofilm-generating probiotic bacterium]" should be deleted.

At Column 96, Line 29 – "[biofilm-generating probiotic bacterium is selected from the group consisting of:]" should be deleted.

At Column 96, Line 33 – "[*L. acidophilus, L. crispatus, L. gasseri, L. delbrueckii, L. salivarius, L. casei, L. paracasei, L. plantarum, L. rhamnosus, L. reuteri, L. brevis, L. buchneri, L. fermentum, L. rhamnosus, B. adolescentis, B. angulation, B. bifidum, B. breve, B. catenulatum, B. infantis, B. lactis, B. longum, B. pseudocatenulatum, S. thermophiles, Pseudomonas fluorescens, P. protegens, P. brassicacearum, P. aeruginosa, Azospirillum. brabrasilense, A. lipferum, A. halopraeferens, A. irakense, Acetobacter diazotrophicus, Herbaspirillum seropedicae, Bacillus subtilis, Pseudomonas stutzeri, fluorescens, P. putida, P. cepacian, P. vesicularis, P. paucimobilis, Bacillus cereus, B. thuringiensis, B. sphaericus, Shewanella oneidensis, Geobacter bemidjiensis, G. metallireducens, G. sulfurreducens, G. uraniireducens, G. lovleyi, Serratia marcescens, Desulfovibrio vulgaris, D. desulfuricans, Dechloromonas aromatic, Deinococcus radiodurans, Methylibium petroleiphilum, Alcanivorax borkumensis, Archaeglobus fulgidus, Haloferax sp., Halobacterium sp.,*]" should be deleted.

At Column 96, Line 52 – "[combinations]" should be deleted.

Signed and Sealed this
Seventeenth Day of January, 2023

Katherine Kelly Vidal
*Director of the United States Patent and Trademark Office*